US008475804B2

(12) United States Patent
Johansen et al.

(10) Patent No.: US 8,475,804 B2
(45) Date of Patent: Jul. 2, 2013

(54) COMPOSITIONS AND METHODS FOR TREATMENT OF FILOVIRUS-MEDIATED DISEASES

(75) Inventors: Lisa M. Johansen, Belmont, MA (US); Joseph Lehár, Lexington, MA (US); Benjamin G. Hoffstrom, Cambridge, MA (US); Gene G. Olinger, Frederick, MD (US); Andrea R. Stossel, Thurmont, MD (US)

(73) Assignees: U.S. Army Medical Research and Material Command, Fort Detrick, MD (US); Zalicus, Inc., Cambridge, MA (US)

( * ) Notice: Subject to any disclaimer, the term of this patent is extended or adjusted under 35 U.S.C. 154(b) by 71 days.

(21) Appl. No.: 12/710,203

(22) Filed: Feb. 22, 2010

(65) Prior Publication Data

US 2011/0028564 A1    Feb. 3, 2011

Related U.S. Application Data

(60) Provisional application No. 61/154,279, filed on Feb. 20, 2009.

(51) Int. Cl.
*A61P 31/12*   (2006.01)
*A61K 31/138*  (2006.01)
*A61K 31/135*  (2006.01)

(52) U.S. Cl.
USPC ........ 424/204.1; 514/651; 514/648; 514/646; 514/657; 514/659; 564/428; 564/308

(58) Field of Classification Search
USPC ............... 424/204.1; 514/651, 648, 646, 657, 514/649; 564/428, 308
See application file for complete search history.

(56) References Cited

U.S. PATENT DOCUMENTS

2006/0039890 A1*   2/2006   Renshaw et al. ........... 424/78.16
2008/0161324 A1*   7/2008   Johansen et al. ......... 514/255.03

* cited by examiner

*Primary Examiner* — Savitha Rao
(74) *Attorney, Agent, or Firm* — Clark & Elbing LLP

(57) ABSTRACT

The invention features compositions, methods, and kits useful for the treatment of filovirus-mediated diseases, e.g., hemorrhagic fever caused by Ebola virus, in an animal.

4 Claims, No Drawings

COMPOSITIONS AND METHODS FOR TREATMENT OF FILOVIRUS-MEDIATED DISEASES

BACKGROUND OF THE INVENTION

The invention relates to the treatment of diseases caused by a filovirus.

Diseases caused by viruses are major health problems worldwide. Filoviruses are particularly deadly viruses that cause severe hemorrhagic fever in humans and non-human primates. Filoviruses are sporadically transmitted to humans from a natural reservoir species thought to be fruit bats, after which the virus can easily spread from the human having the infection to a caregiver through bodily fluids. Infection with a filovirus of the Ebola or Marburg genus causes death in 25% to 90% of human victims, often within 10 days from the first appearance of symptoms.

No known anti-viral therapies are effective for treating filovirus-mediated diseases. Filoviruses thus pose serious unmet health and bioterrorism concerns. Given the lack of safe and efficacious therapies for filovirus-mediated diseases, there is a need for such therapies.

SUMMARY OF THE INVENTION

Based on the results of our screen identifying compounds and combinations of compounds having inhibitory activity against a model filovirus, the present invention features compositions, methods, and kits for the treatment of filovirus-mediated disease, e.g., one caused by an Ebola virus or Marburg virus.

Accordingly, in a first aspect, the invention features a method for treating a patient with a filovirus-mediated disease, e.g., a disease caused by an Ebola virus or Marburg virus. The method includes administering to the patient a first agent selected from the agents of Table 2, or an analog thereof, in an amount that is effective to treat the patient. Preferably, the first agent is selected from the agents of Table 1. More preferably, the first agent is clomiphene, toremifene, astemizole, bepridil, clomopramine, lomerizine, sertraline, or an analog thereof. In another embodiment, the method further includes administering a second agent selected from the agents of Table 1. Preferably, the first and second agents are both selected from Table 1. More preferably, the first and second agents are selected from the agent pairs of Table 3.

TABLE 1

| | | |
|---|---|---|
| Azacitidine | Thioridazine | Piperacetazine |
| Clomiphene | Prochlorperazine | Fluphenazine |
| Toremifene | Sertraline | Aripiprazole |
| Lomerizine | Paroxetine | Maprotiline |
| Bepridil | Clomipramine | Dasatinib |
| Strophanthin | Pimozide | Vinorelbine |
| Atovaquone | Flupentixol | Teicoplanin |
| Mycophenolate Mofetil | Clemastine | Hycanthone |
| Terconazole | Astemizole | Quinacrine |
| Simvastatin | Benztropine | Efavirenz |

TABLE 2

| | | |
|---|---|---|
| Cetrimide | Bafilomycin A1 | Homochlorcyclizine |
| Pentamidine | 2-Methoxy-antimycin A3 | Desloratadine |
| Hexachlorophene | Oligomycin | Flunarizine |
| Emetine | Antimycin A | Loratadine |
| Puromycin | Rotenone | Doxylamine |
| Thiostrepton | FR122047 | Propoxyphene |
| Gramicidin | Fenoprofen Calcium | Benztropine |
| Chlorhexidine | Perhexiline Maleate | Dicyclomine |
| Teicoplanin | PDMP | Piperacetazine |
| Cephapirin | Licochalcone-A | Vanoxerine |
| Pyrithione Zinc | Tiatricol | Pergolide |
| Haloprogin | CAPE | Acetophenazine |
| Ciclopirox | Amlodipine | Bromocriptine |
| hycanthone | Diphenyleneiodonium | Fluphenazine |
| Niclosamide | Terconazole | N-(4-Aminobenzoyl)-L-glutamic acid |
| Efavirenz | Sulconazole | Aripiprazole |
| Ritonavir | Tioconazole | Drotaverine |
| Chromomycin A3 | Oxiconazole | Maprotiline |
| Azacitidine | Simvastatin | CKI7 |
| (−)-Arctigenin | Cerivastatin | Triptolide |
| Danazol | Metergoline | NSC 625987 |
| Bicalutamide | Thioridazine | Bay 41-2272 |
| Hydroxyprogesterone | Thiethylperazine | Alverine |
| Equilin | Cyproheptadine | Tannic Acid |
| Clomiphene | Prochlorperazine | IMD-0354 |
| Quinestrol | Triflupromazine | Arbidol |
| Tamoxifen | Paroxetine | Andrographis |
| Raloxifene | Sertraline | Pyrvinium |
| Tamoxifen | Clomipramine | Deguelin |
| Toremifene | Fenretinide | Dasatinib |
| PGG | Ciclesonide | 5-Iodotubercidin |
| Diethylstilbestrol | Brefeldin A | SP 600125 |
| Tibolone | PGG (1,2,3,4,6-b-O-Pentagalloyl glucose) | Carbobenzoxy-valinyl-phenylalaninal |
| Lomerizine | BML-248 | Cepharanthine |
| Maduramicin | Leupeptin | Sangivamycin |
| Bepridil | Tunicamycin | PKR inhibitor |
| Loperamide | MG115 | Okadaic Acid |
| 6-Azauridine | MG-132 | Sorafenib |
| Strophanthin | Epoxomicin | Sodium Vanadate |
| Beta Escin | Anisomycin | Nocodazole |
| Auranofin | CGS 15943 | Mebendazole |
| Calcimycin A23187 | Pimozide | TN-16 |

TABLE 2-continued

| | | |
|---|---|---|
| Edetate | Guanethidine | Fenbendazole |
| Octyl Gallate | Flupentixol | Podofilox |
| Magnesium Sulfate | Perphenazine | Triclabendazole |
| Rescinnamine | Trifluoperazine | Oxibendazole |
| Cilastatin | EGFR Inhibitor | Vinorelbine |
| Bromelain | Sunitinib | Thapsigargin |
| Quinacrine | Chlorcyclizine | 2,6-Divanillylidenecyclohexanone |
| Methdilazine | Astemizole | 1,5'-Bis(2-Nitrophenoxy)pentane |
| L-Asparagine | Clemastine | Desmethyl Sertraline |
| Chondroitin | Terfenadine | Podophyllum |
| Atovaquone | Chlorphenoxamine | Saponin |
| Mycophenolate Mofetil | Oxatomide | Nonoxynol-9 |
| Mycophenolic Acid | Azelastine | Domiphen Bromide |
| Flucytosine | Clemastine | Sodium Bicarbonate |
| Carbonyl cyanide 4-(trifluoromethoxy)phenylhydrazone | Cycloheximide | Latrunculin B |

TABLE 3

| | |
|---|---|
| Lomerizine and Vinolrelbine | Dasatinib and Lomerizine |
| Pimozide and Vinolrelbine | Aripiprazole and and Piperacetazine |
| Aripiprazole and Vinolrelbine | Pimozide and Thioridazine |
| Aripiprazole and Dasatinib | Aripiprazole and Astemizole |
| Clemastine and Sertraline | Bepridil and Clomiphene |
| Bepridil and Toremifene | Clomiphene and Sertraline |
| Toremifene and Sertraline | Sertraline and Vinorelbine |
| Aripiprazole and Paroxetine | |

The invention also features a method for treating a patient having a filovirus-mediated disease, e.g., a disease caused by Ebola virus or Marburg virus, the method including administering to the patient: a first agent that is an inhibitor of estrogen receptor a and a second agent that is an inhibitor of histamine receptor 1 in amounts that together are effective to treat the patient. The first agent is preferably clomiphene, tamoxifen, raloxifene, toremifene, diethylstilbestrol, or an analog thereof. More preferably, the first agent is clomiphene, tamoxifen, toremifene, or an analog thereof. The second agent is preferably chlorcyclizine, astemizole, clemastine, terfenadine, chlorphenoxamine, oxatomide, azelastine, methdilazine, homochlorcyclizine, desloratadine, flunarizine, loratadine, doxylamine, or an analog thereof. More preferably, the second agent is astemizole or an analog thereof.

The invention also features a method for treating a patient having a filovirus-mediated disease, e.g., a disease caused by Ebola virus or Marburg virus, the method including administering to the patient: a first agent that is an inhibitor of estrogen receptor a and a second agent that is sertraline or an analog thereof in amounts that together are effective to treat the patient. The first agent is preferably clomiphene, tamoxifen, raloxifene, toremifene, diethylstilbestrol, or an analog thereof. More preferably, the first agent is clomiphene, tamoxifen, toremifene, or an analog thereof. The second agent is preferably sertraline, paroxetine, or UK-416244.

When the methods includes administering to the patient a pair of active agents, the agents may be administered within within 28, 21, 14, 10, 7, 5, 4, 3, 2, or 1 days; within 24, 12, 6, 3, 2, or 1 hours; or substantially simultaneously. The methods of the invention may include administering one or more agents to the patient by oral, systemic, parenteral, topical (e.g., ophthalmic, dermatologic), intravenous, inhalational, or intramuscular administration.

In certain embodiments of any of the above methods (e.g., a method including administration of an inhibitor of estrogen receptor a), the patient being treated has not been diagnosed with or does not suffer from breast cancer, osteoporosis, prostate hyperplasia, metabolic syndrome X, male infertility, testosterone deficiency, hypogonadism, non-insulin-dependent diabetes, infertility due to an ovulatory disorder, infertility due to polycystic ovary syndrome, gynaecomastia, or hormone deficiency. In certain other embodiments of any of the above methods (e.g., a method including administration of an inhibitor of histamine receptor 1), the patient has not been diagnosed with or does not suffer from urticaria, seasonal allergic rhinitis, allergy or excessive itching, or cancer (e.g., cancer of the lung, pancreatic, ovary, breast, prostate, colon, brain, or skin). In other certain embodiments of any of the methods (e.g., a method including administration of a selective serotonin reuptake inhibitor or a phenothiazine), the patient being treated has not been diagnosed with or does not suffer from a major depressive disorder, an obsessive-compulsive disorder, an anxiety disorder, or a psychotic disorder (e.g., schizophrenia). In yet other certain embodiments of any of the above methods, the patient being treated has not been diagnosed with or does not suffer from migraine, cardiac arrhythmia, hypertension, pneumocystis pneumonia, toxoplasmosis, malaria, organ transplant rejection, fungal infection, hypolipidemia, hypercholesterolemia, chronic myelogenous leukemia, cancer (e.g., cancer of the lung, pancreatic, ovary, breast, prostate, colon, brain, or skin), bacterial infection, schistosomal infection, malaria, HIV, osteoporosis, gynaecomastia.

In another aspect, the invention features a composition including two or more agents selected from the agents of Table 1. Preferably, the two or more agents are present in amounts that, when administered together to a patient with a filovirus-mediated disease (e.g., a disease caused by Ebola virus or Marburg virus), are effective to treat the patient. More preferably, the first and second agents are selected from the agent pairs of Table 3. In another embodiment, the composition consists of active ingredients and excipients, and the active ingredients consist of said two agents selected from the agents of Table 1.

The invention also features a composition that includes a first agent that is an inhibitor of estrogen receptor α and a second agent that is an inhibitor of histamine receptor 1. Preferably, the first and second agents are present in amounts that, when administered together to a patient with a filovirus-mediated disease (e.g., a disease caused by Ebola virus or Marburg virus), are effective to treat the patient. The first agent is preferably clomiphene, tamoxifen, raloxifene, toremifene, diethylstilbestrol, or an analog thereof. More preferably, the first agent is clomiphene, tamoxifen, toremifene, or an analog thereof. The second agent is preferably chlorcyclizine, astemizole, clemastine, terfenadine, chlorphenoxamine, oxatomide, azelastine, methdilazine, homochlorcyclizine, desloratadine, flunarizine, loratadine, doxylamine, or an analog thereof. More preferably, the second agent is astemizole or an analog thereof. In another embodiment, the composition consists of active ingredients and excipients, and the active ingredients consist of the first and second agents The invention also features a composition that includes a first agent that is an inhibitor of estrogen receptor a and a second agent that is sertraline or an analog thereof. Preferably, the first and second agents are present in amounts that, when administered together to a patient with a filovirus-mediated disease (e.g., a disease caused by Ebola virus or Marburg virus), are effective to treat the patient. The first agent is preferably clomiphene, tamoxifen, raloxifene, toremifene, diethylstilbestrol, or an analog thereof. More preferably, the first agent is clomiphene, tamoxifen, toremifene, or an analog thereof. The second agent is preferably sertraline, paroxetine, or UK-416244. In another embodiment, the composition consists of active ingredients and excipients, and the active ingredients consist of the first and second agents Any of the compositions of the invention may be formulated, for example, for oral, systemic, parenteral, topical (e.g., ophthalmic, dermatologic), intravenous, inhalational, or intramuscular administration.

In another aspect, the invention features a kit including an active agent selected from the agents of Table 2 and instructions for administering the agent to a patient having a filovirus-mediated disease, e.g., a disease caused by an Ebola or a Marburg virus. Preferably, the active agent is selected from the agents of Table 1. More preferably, the active agent is clomiphene, toremifene, astemizole, bepridil, clomopramine, lomerizine, sertraline, or an analog thereof.

The invention also features a kit including two or more agents selected from the agents of Table 1 and instructions for administering the agents to a patient having a filovirus-mediated disease, e.g., a disease causes by an Ebola or a Marburg virus. Preferably, the two agents are selected from the agent pairs of Table 3. The two agents may be included together in a composition or may be formulated separately.

Related embodiments of the invention are kits including a first agent and selected from Table 1 and instructions for administering the first agent with a second agent selected from Table 1 to a patient having a filovirus-mediated disease, e.g., one caused by an Ebola virus or Marburg virus. Preferably, the first and second agents are each clomiphene, toremifene, astemizole, bepridil, clomopramine, lomerizine, sertraline, or an analog thereof.

The invention also features kits that include an agent that is an inhibitor of estrogen receptor a, an agent that is an inhibitor of histamine receptor 1, and instructions for administering the agents to a patient with a filovirus-mediated disease, e.g., one caused by an Ebola virus or Marburg virus. Related embodiments of the invention feature a kit in which one of the estrogen receptor a and histamine receptor 1 inhibitory agents is included with instructions for administering the other agent of the combination to a patient with a filovirus-mediated disease, e.g., one caused by an Ebola virus or Marburg virus. In any of these embodiments, the inhibitor of estrogen receptor $\alpha$ is preferably selected from clomiphene, tamoxifen, toremifene, and analogs thereof and more preferably from clomiphene, tamoxifen, raloxifene, toremifene, and diethylstilbestrol, and analogs thereof. In these embodiments, the inhibitor of histamine receptor 1 is preferably selected from the group consisting of chlorcyclizine, astemizole, clemastine, terfenadine, chlorphenoxamine, oxatomide, azelastine, methdilazine, homochlorcyclizine, desloratadine, flunarizine, loratadine, doxylamine, and analogs thereof, and more preferably from astemizole or an analog thereof. When the kit includes the inhibitor of estrogen receptor a and the inhibitor of histamine receptor, the two agents may be included together in a composition or they may be formulated separately.

The invention also features kits that include an agent that is an inhibitor of estrogen receptor $\alpha$, an agent that is sertraline or an analog thereof, and instructions for administering the agents to a patient with a filovirus-mediated disease, e.g., one caused by an Ebola virus or Marburg virus. Related embodiments of the invention feature a kit in which one of the estrogen receptor a inhibitors and sertraline or analog thereof is included with instructions for administering the other agent of the combination to a patient with a filovirus-mediated disease, e.g., one caused by an Ebola virus or Marburg virus. In any of these embodiments, the inhibitor of estrogen receptor $\alpha$ is preferably selected from clomiphene, tamoxifen, toremifene, and analogs thereof and more preferably from clomiphene, tamoxifen, raloxifene, toremifene, and diethylstilbestrol, and analogs thereof. In these embodiments, the sertraline or analog thereof is preferably sertraline, paroxetine, or UK-416244. When the kit includes the inhibitor of estrogen receptor a and the sertraline or analog thereof, the two agents may be included together in a composition or they may be formulated separately.

In any of the compositions, methods, or kits that include an inhibitor of estrogen receptor a and an inhibitor of histamine receptor 1, these agents are preferably clomiphene and chlorcyclizine, clomiphene and astemizole, clomiphene and clemastine, clomiphene and terfenadine, clomiphene and chlorphenoxamine, clomiphene and oxatomide, clomiphene and azelastine, clomiphene and methdilazine, clomiphene and homochlorcyclizine, clomiphene and desloratadine, clomiphene and flunarizine, clomiphene and loratadine, clomiphene and doxylamine, tamoxifen and chlorcyclizine, tamoxifen and astemizole, tamoxifen and clemastine, tamoxifen and terfenadine, tamoxifen and chlorphenoxamine, tamoxifen and oxatomide, tamoxifen and azelastine, tamoxifen and methdilazine, tamoxifen and homochlorcyclizine, tamoxifen and desloratadine, tamoxifen and flunarizine, tamoxifen and loratadine, tamoxifen and doxylamine, toremifene and chlorcyclizine, toremifene and astemizole, toremifene and clemastine, toremifene and terfenadine, toremifene and chlorphenoxamine, toremifene and oxatomide, toremifene and azelastine, toremifene and methdilazine, toremifene and homochlorcyclizine, toremifene and desloratadine, toremifene and flunarizine, toremifene and loratadine, toremifene and doxylamine, raloxifene and chlorcyclizine, raloxifene and astemizole, raloxifene and clemastine, raloxifene and terfenadine, raloxifene and chlorphenoxamine, raloxifene and oxatomide, raloxifene and azelastine, raloxifene and methdilazine, raloxifene and homochlorcyclizine, raloxifene and desloratadine, raloxifene and flunarizine, raloxifene and loratadine, raloxifene and doxylamine, diethylstilbestrol and chlorcyclizine, diethylstilbestrol and astemizole, diethylstilbestrol and clemastine, diethylstilbestrol and terfenadine, diethylstilbestrol and chlorphenoxamine, diethylstilbestrol and oxatomide, diethylstilbestrol and azelastine, diethylstilbestrol and methdilazine, diethylstilbestrol and homochlorcyclizine, diethylstilbestrol and desloratadine, diethylstilbestrol and flunarizine, diethylstilbestrol and loratadine, or diethylstilbestrol and doxylamine.

In any of the kits of the invention, one or more active agents may be formulated, e.g., for oral, parenteral, systemic, topical, or inhalational administration.

Analogs of any of the compounds listed in Tables 1 and 2 may be used in any of the compositions, methods, and kits of the invention.

Compounds useful in the invention include those described herein in any of their pharmaceutically acceptable forms, including isomers such as diastereomers and enantiomers, salts, solvates, and polymorphs thereof, as well as racemic mixtures. Compounds useful in the invention may also be isotopically labeled compounds. Useful isotopes include hydrogen, carbon, nitrogen, oxygen, phosphorous, fluorine, and chlorine, (e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$). Isotopically-labeled compounds can be prepared by synthesizing a compound using a readily available isotopically-labeled reagent in place of a non-isotopically-labeled reagent.

By "agent" is meant a compound, e.g., toremifene, or mixture of compounds, e.g., teicoplanin, having a pharmacological activity. The terms "agent," "compound," and "drug" are used interchangeably herein.

"Histamine receptor 1" refers to the histamine receptor also known as $H_1$ receptor and HRH1.

By an "inhibitor of histamine receptor 1," is meant an agent that antagonizes the signaling of histamine receptor 1 by at least 5%, 10%, 25%, 50%, 60%, 70%, 80%, 90%, or 95%. Inhibition of histamine receptor 1 signaling by an agent can be measured, for example, by reporter assays known in the art.

As used herein, the term "estrogen receptor $\alpha$" (ER$\alpha$) refers to estrogen hormone receptors containing the estrogen receptor polypeptide encoded by the estrogen receptor 1 (ESR1) gene. An estrogen receptor a protein can include a homodimer of polypeptides encoded by ESR1 or a heterodimer of polypeptides encoded by the ESR1 and estrogen receptor 2 (ESR2) genes.

By an "estrogen receptor a inhibitor" is meant an agent that binds to and antagonizes the activity of estrogen receptor a by at least 5%, 10%, 25%, 50%, 60%, 70%, 80%, 90%, or 95% in at least one cell type of an animal. Certain estrogen receptor a inhibitors, e.g., agents known in the art as "selective estrogen receptor modulators," may inhibit estrogen receptors in one organ, e.g., the breast, while activating estrogen receptors in another organ, e.g., the liver, bone, or uterus. Such compounds are included in the term "estrogen receptor a inhibitors." The % inhibition of estrogen receptor a activity by an agent can be measured, for example, by a reporter assay known in the art.

By a "filovirus" is meant a virus belonging to the family Filoviridae. Exemplary filoviruses are Ebola virus and Marburg virus.

By "patient" is meant any animal, e.g., a primate, e.g., a human. Any animal can be treated using the methods, compositions, and kits of the invention.

To "treat" is meant to administer one or more agents to measurably slow or stop the replication of a virus in vitro or in vivo, to measurably decrease the load of a virus (e.g., any virus described herein including a filovirus virus such as an Ebola virus or Marburg virus) in a cell in vitro or in vivo, or to reduce at least one symptom (e.g., those described herein) associated with having a filovirus-mediated disease in a patient. Desirably, the slowing in replication or the decrease in viral load is at least 10%, 20%, 30%, 40%, 50%, 60%, 70%, 80%, 90%, 95%, or 99%, as determined using a suitable assay (e.g., a replication assay described herein). Alternatively, in certain embodiments, treatment is observed by a trained physician as an appreciable or substantial relief of symptoms in a patient with a filovirus-mediated disease. Typically, a decrease in viral replication is accomplished by reducing the rate of RNA polymerization, RNA translation, protein processing or modification, or by reducing the activity of a molecule involved in any step of viral replication (e.g., proteins or coded by the genome of the virus or host important for viral replication).

By "an effective amount" is meant the amount of a compound, alone or in combination with another therapeutic regimen, required to treat a patient with a viral disease (e.g., any virus described herein including an Ebola virus or Marburg virus) in a clinically relevant manner. A sufficient amount of an active compound used to practice the present invention for therapeutic treatment of conditions caused by a virus varies depending upon the manner of administration, the age, body weight, and general health of the patient. Ultimately, the prescribers will decide the appropriate amount and dosage regimen. In a combination therapy of the invention, the effective amount of an agent may less be than the effective amount if the agent were administered in a non-combinatorial (single-agent) therapy. Additionally, an effective amount may be an amount of an agent in a combination therapy of the invention that is safe and efficacious in the treatment of a patient having a viral disease over each agent alone as determined and approved by a regulatory authority (such as the U.S. Food and Drug Administration).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

By a "low dosage" is meant at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that inhibits viral replication and that is formulated for administration by intravenous injection will differ from a low dosage of the same agent formulated for oral administration.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 12 ring carbon atoms, inclusive. Exemplary cyclic groups include cyclopropyl, cyclobutyl, cyclopentyl, and cyclohexyl groups.

By "$C_{1-4}$ alkyl" is meant a branched or unbranched hydrocarbon group having from 1 to 4 carbon atoms. A $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls include, without limitation, methyl, ethyl, n-propyl, isopropyl, cyclopropyl, cyclopropylmethyl, n-butyl, iso-butyl, sec-butyl, tert-butyl, and cyclobutyl.

By "C$_{2-4}$ alkenyl" is meant a branched or unbranched hydrocarbon group containing one or more double bonds and having from 2 to 4 carbon atoms. A C$_{2-4}$ alkenyl may optionally include monocyclic or polycyclic rings, in which each ring desirably has from three to six members. The C$_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. C$_{2-4}$ alkenyls include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

By "C$_{2-4}$ alkynyl" is meant a branched or unbranched hydrocarbon group containing one or more triple bonds and having from 2 to 4 carbon atoms. A C$_{2-4}$ alkynyl may optionally include monocyclic, bicyclic, or tricyclic rings, in which each ring desirably has five or six members. The C$_{2-4}$ alkynyl group may be substituted or unsubstituted. Exemplary substituents include alkoxy, aryloxy, sulfhydryl, alkylthio, arylthio, halide, hydroxy, fluoroalkyl, perfluoroalkyl, amino, aminoalkyl, disubstituted amino, quaternary amino, hydroxyalkyl, carboxyalkyl, and carboxyl groups. C$_{2-4}$ alkynyls include, without limitation, ethynyl, 1-propynyl, 2-propynyl, 1-butynyl, 2-butynyl, and 3-butynyl.

By "C$_{2-6}$ heterocyclyl" is meant a stable 5- to 7-membered monocyclic or 7- to 14-membered bicyclic heterocyclic ring which is saturated, partially unsaturated, or unsaturated (aromatic), and which consists of 2 to 6 carbon atoms and 1, 2, 3, or 4 heteroatoms independently selected from N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoroalkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "C$_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "C$_{7-14}$ alkaryl" is meant an alkyl substituted by an aryl group (e.g., benzyl, phenethyl, or 3,4-dichlorophenethyl) having from 7 to 14 carbon atoms.

By "C$_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

By "C$_{1-7}$ heteroalkyl" is meant a branched or unbranched alkyl, alkenyl, or alkynyl group having from 1 to 7 carbon atoms in addition to 1, 2, 3, or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups. Examples of C$_{1-7}$ heteroalkyls include, without limitation, methoxymethyl and ethoxyethyl.

By "halide" or "halogen" is meant bromine, chlorine, iodine, or fluorine.

By "fluoroalkyl" is meant an alkyl group that is substituted with a fluorine atom.

By "perfluoroalkyl" is meant an alkyl group consisting of only carbon and fluorine atoms.

By "carboxyalkyl" is meant a chemical moiety with the formula —(R)—COOH, wherein R is selected from C$_{1-7}$ alkyl, C$_{2-7}$ alkenyl, C$_{2-7}$ alkynyl, C$_{2-6}$ heterocyclyl, C$_{6-12}$ aryl, C$_{7-14}$ alkaryl, C$_{3-10}$ alkheterocyclyl, or C$_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula $N(R)(R')(R'')(R''')^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl, heteroalkyl, heteroaryl, and/or aryl groups, resulting in a positive charge at the nitrogen atom.

Other features and advantages of the invention will be apparent from the following Detailed Description and the claims.

DETAILED DESCRIPTION OF THE INVENTION

We have identified compounds that decrease replication of an infectious filovirus engineered with a green fluorescent protein (GFP) in mammalian cells. Accordingly, the present invention provides compositions, methods, and kits useful in the treatment of viral diseases caused by a filovirus. In certain embodiments, the viral disease is caused by an Ebola virus or Marburg virus. Compositions of the invention can include a combination pair of any two agents selected from Table 2 or the particular pairs of agents of Table 3. Treatment methods of the invention include administration of a single agent from Table 1 or Table 2 or a pair of agents selected from the agents of Table 1 or from the agent pairs listed in Table 3. Optionally, functional or structural analogs (e.g., those described herein) of these agents may be employed in the compositions, methods, and kits of the invention. The composition may function by decreasing RNA polymerization, RNA translation, RNA transcription, a decrease in posttranslational protein processing, or a decrease in activity of a protein involved in viral replication (e.g., a protein coded for by the viral genome or a host protein required for viral replication).

In one particular example, the patient being treated is administered a combination of two agents listed in Table 1 within 7 days of each other in amounts that together are sufficient to treat the patient having a filovirus-mediated disease. An effective amount of one or both of the agents may be a low dosage relative the effective amount of the agent when administered singly.

Filovirus-Mediated Diseases

The invention relates to the treatment of diseases caused by viruses of the family Filoviridae (filoviruses). Filoviruses are negative strand RNA viruses that can infect humans and primates. Filoviruses include viruses of the genera *Ebolavirus* and *Marburgvirus*. In particular, Ebola hemorrhagic fever is a severe, often-fatal disease in humans and has appeared sporadically since its initial recognition in 1976. The disease is caused by infection with an Ebola virus. Five identified subtypes of Ebola virus are Ebola-Zaire, Ebola-Sudan, Ebola-Ivory Coast, and Ebola-Bundibugyo, each of which have caused disease in humans, and Ebola-Reston, which has caused disease in nonhuman primates, but not in humans. Other undiscovered subtypes may exist and are intended to be included in the scope of Ebola virus.

Infection with an Ebola or Marburg virus usually causes life-threatening hemorrhagic fever. Symptoms include fever, severe headache, joint and muscle aches, chills, sore throat, weakness, nausea and vomiting, diarrhea, red eyes, raised rash, chest pain and cough, hiccups (Ebola virus), stomach pain, bleeding (from any bodily orifice), and psychological symptoms (confusion, irribility, aggression, or depression). As the illness progresses, jaundice, dilirium, seizures, severe bleeding, organ failure, coma, shock, and death can occur.

Agents of the Invention

Certain agents that may be employed in the methods, compositions, and kits of the present invention are discussed in greater detail below. It is understood that an analog of any compound of Table 1 and Table 2 can be used instead of the compound of Table 1 or Table 2 in the methods, compositions, and kits of the present invention.

Estrogen Receptor Inhibitors

In certain embodiments, an estrogen receptor α inhibitor can be used in the compositions, methods, and kits of the invention. By an "estrogen receptor α inhibitor" is meant a compound that inhibits the activity of an estrogen receptor a by at least 5%, e.g., greater than 10%, 20%, 40%, 60%, 80%, 90%, or 95%. ERα inhibitors include clomiphene, tamoxifen, tomerifene, and raloxifene. ERα inhibitors that may be particularly efficacious are described in more detail below.

Clomiphene

Clomiphene is described in U.S. Pat. No. 2,914,563 and has the following structure:

Structural analogs of clomiphene include olefinic isomers. Structural analogs of clomiphene are also described by the following formula:

wherein X is any halogen (e.g., F, Cl, Br, or I), $R_1$, $R_2$, and $R_3$ may be located at any position of the phenyl group and are selected, independently, from H, halogen, $C_{1-6}$ alkyl, $C_{1-6}$ alkoxy, —$OC_nH_{2n}A$, and at least one of $R_1$, $R_2$, and $R_3$ is —OC$_n$H$_{2n}$A, wherein n is 2, 4, 5, or 6; A=NR$_4$R$_5$, wherein each R$_4$ and R$_5$ is, independently, an optionally substituted C$_{1-6}$ alkyl, or R$_4$ and R$_5$ combined to form an optionally substituted cyclic structure.

Desirably, when R$_1$, R$_2$, or R$_3$ is —OC$_n$H$_{2n}$A, the substituents is located para to the olefin substituents. Examples of C$_{1-6}$ alkyls include, but are not limited to: methyl, ethyl, propyl, isopropyl, n-butyl, iso-butyl, sec-butyl, tert-butyl, n-pentyl, isoamyl, and n-hexyl. Examples of C$_{1-6}$ alkoxy groups include, but are not limited to: methoxy, ethoxy, propoxy, isopropoxy, n-butyloxy, iso-butyloxy, sec-butyloxy, tert-butyloxy, n-pentoxy, O-isoamyl, and O-hexyl. Examples of rings formed by the combination R$_4$ and R$_5$ include, but are not limited to pyrrolidine and piperidine.

Other clomiphene analogs are described in U.S. Pat. Nos. 2,914,563 and 5,189,212 and by the general formula of U.S. Pat. No. 5,410,080.

Tamoxifen

Tamoxifen is described in U.S. Pat. No. 4,536,516 and has the following structure:

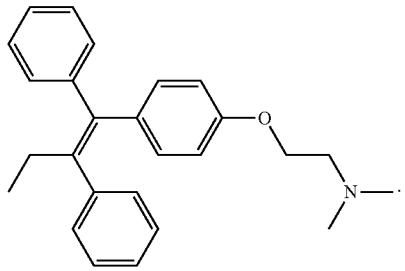 [SMILES: CC/C(=C(\c1ccccc1)c1ccc(OCCN(C)C)cc1)c1ccccc1]

Tamoxifen analogs are described by general formula (I) in U.S. Pat. No. 4,806,685, e.g., threo-1-[4-(2,3-epoxypropoxy)-phenyl]-1,2-diphenyl-3,3,3-trifluoro-propane, (E)-1,2-diphenyl-3,3,3-trifluoro-1-[4-(2-[4-methylpiperazino]-ethoxy)-phenyl]-propene, 1-[4-(2-dimethylaminoethoxy)-phenyl]-2-phenyl-3,3,3-trifluoro-1-(4-hydroxy phenyl) propene, (E)1,2-diphenyl-3,3,3-trifluoro-1-[4-(2-[2-hydroxyethylamino]-ethoxy)-phenyl]-propene, (E)-1-[4-(2-azidoethoxy)-phenyl]-1,2-diphenyl-3,3,3-trifluoro-propene, and 1-[4-(2-dimethylamino-ethoxy)-phenyl]-3,3,3-trifluoro-1,2-bis-(4-hydroxyphenyl)-propene.

Other tamoxifen analogs are described by general formula (I) in U.S. Pat. No. 5,047,431, e.g., (E)-1-[4'-(2-dimethylaminoethoxy)phenyl]-1-(3'-hydroxyphenyl)-2-phenylbut-1-ene, (E)-1-[4'(2-diethylaminoethoxy)phenyl]-1-(3'-hydroxyphenyl)-2-phenylbut-1-ene, (E)-1-(3'-hydroxyphenyl)-1-[4'-(2-methylaminoethoxy)phenyl]-2-phenylbut-1-ene, and (E)-1-[4'-ethylaminoethoxy)phenyl]-1-(3'-hydroxyphenyl)-2-phenylbut-1-ene.

Yet other tamoxifen analogs are described by formula (I) in U.S. Pat. No. 5,681,835, e.g., 3-[4-(1,2-diphenyl-but-1-enyl)-phenyl]-N,N-diethyl acrylamide, 3-[4-(1,2-diphenyl-but-1-enyl)-phenyl]-N,N-diethyl propionamide, 2-[4-(1,2-diphenyl-but-1-enyl)-phenyl]cyclopropanecarboxylic acid diethylamide, 3-[4-(1,2-diphenyl-but-1-enyl)-phenyl]-N,N-diethyl-2-methyl-acrylamide, 3-[4-(1,2-diphenyl-but-1-enyl)-phenyl]-but-2-enoic acid diethylamide, 3-[4-(1,2-diphenyl-but-1-enyl)-phenyl]-acrylic acid methyl ester, 3-[4-(1,2-diphenyl-but-1-enyl)-phenyl]-acrylonitrile, 3-[4-(1,2-diphenyl-but-1-enyl)-phenyl]-acrylic acid tert-butyl ester, 3-[4-(1,2-diphenyl-but-1-enyl)-phenyl]-acrylic acid, 3-[4-(1,2-diphenyl-but-1-enyl)-phenyl]-1-morpholin-4-yl-prop-2-en-1-one, 3-[4-(1,2-diphenyl-but-1-enyl)-phenyl]-N-(3-methoxy-propyl)-acrylamide, and N,N-dicyclohexyl-3-[4-(1,2-diphenyl-but-1-enyl)-phenyl]acrylamide.

Additional tamoxifen analogs are droloxifene, 4-iodotamoxifen, idoxifene, described in U.S. Pat. No. 6,096,874, in U.S. Pat. No. 6,576,645, in U.S. Pat. No. 6,875,775, and by general formula (I) of U.S. Pat. No. 5,807,899.

Toremifene

Toremifene is described in U.S. Pat. No. 4,696,949 and has the following structure:

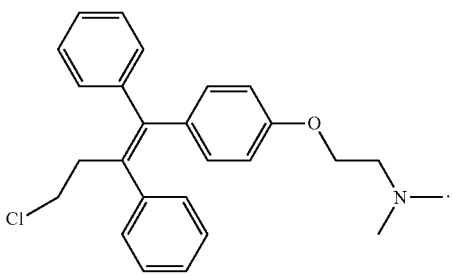 [SMILES: CN(C)CCOc1ccc(/C(=C(/CCCl)c2ccccc2)c2ccccc2)cc1]

Analogs of toremifene analogs are described by several structural formulae described in U.S. Pat. No. 4,696,949, U.S. Pat. No. 4,996,225, and U.S. Pat. No. 5,491,173. Examples are 1-phenyl-1,2-bis(4-hydroxyphenyl)-1-buten-4-ol, 4-bromo-1-phenyl-1,2-bis(4-hydroxyphenyl)-1-butene, 2-phenyl-2,3-bis(4-hydroxyphenyl)tetrahydrofuran, 1,2-diphenyl-1-(4-hydroxyphenyl)-1-penten-5-ol, 2,3-diphenyl-2-(4-hydroxyphenyl)tetrahydropyran, 1,2-diphenyl-1-(4-hydroxyphenyl)-1-penten-5-al, 1,2-diphenyl-1-(4-hydroxyphenyl)-1-buten-4-ol, 2,3-diphenyl-2-(4-hydroxyphenyl)tetrahydrofuran, 1,2-diphenyl-1-[4-[2-(N,N-dimethylamino)ethoxy]phenyl]-1-buten-4-ol, 4-chloro-1,2-diphenyl-1-[4-[2-(N,N-dimethylamino)ethoxy]phenyl]-1-butene, 4-chloro-1,2-diphenyl-1-[4-[2-(1-aziridinyl)ethoxy]phenyl]-1-butene, 4-bromo-1,2-diphenyl-1-[4-[2-(1-pyrrolidinyl)ethoxy]phenyl]-1-butene, 2,3-diphenyl-2-[4-[2-(N,N-diethylamino)ethoxy]phenyl]tetrahydrofuran, 1-phenyl-1,2-bis(4-hydroxyphenyl)butan-4-ol, 4-bromo-1-phenyl-1,2-bis(4-hydroxyphenyl)butane, 1,2-diphenyl-1-(4-hydroxyphenyl)butan-4-ol, 4-chloro-1,2-diphenyl-1-[4-(2-piperidinoethoxy)phenyl]butane, 1,2-diphenyl-1-(4-hydroxyphenyl)butane-1,4-diol, 1-phenyl-1,2-bis(4-hydroxyphenyl)butane-1,4-diol, 1,2-diphenyl-1-(4-methoxyphenyl)-1-buten-4-ol, 4-bromo-1,2-diphenyl-1-[4-[2-(N,N-dimethylamino)ethoxy]phenyl]-1-butene, 4-chloro-1,2-diphenyl-1-(4-hydroxyphenyl)butane, 4-chloro-1,2-diphenyl-1-(4-hydroxyphenyl)-1-butene, and 1,2-diphenyl-1-[4-[2-(N,N-dimethylamino)ethoxy]phenyl]butane-1,4-diol.

Additional examples of toremifene analogs are given by formula (I) of U.S. Pat. No. 5,491,173.

Inhibitors of Histamine Receptor 1

In certain embodiments, the methods, compositions, and kits of the invention employ an inhibitor of histamine receptor 1. The inhibitor may inhibit the activity of histamine receptor 1 by at least 5%, e.g., greater than 10%, 20%, 40%, 60%, 80%, 90%, or 95%. Either non-sedating or sedating inhibitors may be employed. Exemplary histamine receptor 1 inhibitors include acrivastine, alcaftadine, antazoline, azatadine, AZD-1744, azelastine, bepotastine, bepotastine besilate, betotastine besilate, bilastine, BM-113, carebastine, cetirizine, chlorpheniramine, chlorphenoxamine, clemastine, cyclizine, desloratadine, doxepin, E-4716, ebastine, efletirizine, epinastine, epinastine, fexofenadine, FK-613, GSK-1004723, HSR- 609, IOT-101, KA-398, KAA-276, KC-11404, KC-11425, ketotifen, levocetirizine, loratadine, MDL-28163, mianserin, mizolastine, NBI-75043, NIP-530, noberastine, olopatadine, oxatomide, periciazine, pheniramine, promethazine, ReN-1869, rupatadine, selenotifen, SUN-1334H, tagorizine, tecastemizole, terfenadine, tranilast, tranilast, triprolidine, UCB-35440, vapitadine, VUF-K-9015, WY-49051, YM-344484, ZCR-2060. Structural analogs of any of the above histamine receptor 1 inhibitors or other inhibitors of histamine receptor 1 may also be employed instead of these.

Inhibitors of histamine receptor 1 that may be particularly efficacious is described in more detail below.

Astemizole

Astemizole is described in U.S. Pat. No. 4,219,559 and has the following structure:

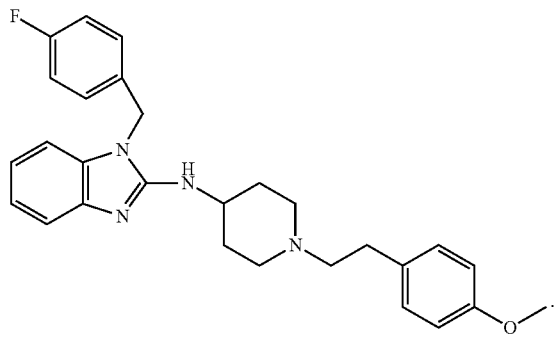 [SMILES: COc1ccc(CCN2CCC(Nc3nc4ccccc4n3Cc3ccc(F)cc3)CC2)cc1]

Analogs of astemizole include, e.g., 1-(4-fluorophenylmethyl)-N-{1-[2-(4-methoxyphenyl)ethyl]-4-piperidinyl}-1H-benzimidazol-2-amine, 4-[2-{4-[1-(4-fluorophenylmethyl)-1H-benzimidazol-2-ylamino]-1-piperidinyl}ethyl]phenol, {4-[2-{4-[1-(4-fluorophenylmethyl)-1H-benzimidazol-2-ylamino]-1-piperidinyl}ethyl]phenyl}benzeneacetate, {4-[2-{4-[1-(4-fluorophenylmethyl)-1H-benzimidazol-2-ylamino]-1-piperidinyl}ethyl]phenoxy}acetonitrile, and compounds described by the formula of claim 1 in U.S. Pat. No. 4,219,559. Additional analogs are described by formula I in U.S. Pat. No. 4,556,660, e.g., [(4-fluorophenyl)methyl]-N-[1-[2-[(2-pyridinyl)amino]ethyl]-4-piperidinyl]-3H-imidazo[4,5-b]pyridin-2-amine, 2-[[2-[4-[[3-[(4-fluorophenyl)methyl]-3H-imidazo[4,5-b]pyridin-2-yl]amino]-1-piperidinyl]ethyl]amino]-3-pyridinecarboxamide, 1-[(4-fluorophenypmethyl]-N-[1-[2-[(2-pyrimidinyl)amino]ethyl]-4-piperidinyl]-1H-imidazo[4,5-b]pyridin-2-amine, 1[(4-fluorophenyl)methyl]-N-[1-[2-(2-pyrimidinylamino)ethyl]-4-piperidinyl]1H-imidazo[4,5-c]pyridin-2-amine, 3-(2-pyridinylmethyl)-N-[1-[2-(2-pyrimidinylamino)ethyl]-4-piperidinyl]3H-imidazo[4,5-b]pyridin-2-amine(E)-2-butenedioate, 3-(2-furanylmethyl)-N-[1-[2-(2-pyrimidinylamino)ethyl]-4-piperidinyl]-3H-imidazo[4,5-b]pyridin-2-amine, 3-[(4-fluorophenyl)methyl]-N-[1-[2-[(2-pyrimidinyl)amino]ethyl]-4-piperidinyl]-3H-imidazo[4,5-c]pyridin-2-amine(E)-2-butenedioate, N-[1-[3-[(5-chloro-2-pyridinyl)amino]propyl]-4-piperidinyl]-1-[(4-fluorophenyl)methyl]-1H-benzimidazol-2-amine trihydrochloride monohydrate, 6-chloro-N.sup.4-[2-[4-[[1-[(4-fluorophenyl)methyl]-1H-benzimidazol-2-yl]amino]-1-piperidinyl]ethyl]-4,5-pyrimidinediamine, 8-chloro-N-[2-[4-[[1-[(4-fluorophenyl)methyl]-1H-benzimidazol-2-yl]amino]-1-piperidinyl]ethyl]-3-phthalazinamine 2-propanolate, 1-(phenylmethyl)-N-[1-[2-[(2-pyridinyl)amino]ethyl]-4-piperidinyl]-1H-benzimidazol-2-amine, 1-methyl-N-[1-[2-[(2-pyrimidinyl)amino]ethyl]-4-piperidinyl]-1H-benzimidazol-2-amine hemihydrate, 1-[(4-methylphenyl)methyl]-N-[1-[2-[(2-pyrimidinyl)amino]ethyl]-4-piperidinyl]-1H-benzimidazol-2-amine, 1-[(4-chlorophenyl)methyl]-N-[1-[2-(2-pyrimidinylamino)ethyl]-4-piperidinyl]-1H-benzimidazol-2-amine, 1-[(4-methoxyphenyl)methyl]-N-[1-[2-(2-pyrimidinylamino)ethyl]-4-piperidinyl]-1H-benzimidazol-2-amine, N-[1-[2-(2-pyrimidinylamino)ethyl]-4-piperidinyl]-1H-benzimidazol-2-amine, 1-[(4-fluorophenyl)methyl]-5-methoxy-N-[1-[2-(2-pyrimidinylamino)ethyl]-4-piperidinyl]-1H-benzimidazol-2-amine, N-[1-[2-(2-pyrimidinylamino)ethyl]-4-piperidinyl]-1-(4-thiazolylmethyl)-1H-benzimidazol-2-amine (E)-2-butenedioate, 4-[[2-[[1-[2-(2-pyrimidinylamino)ethyl]-4-piperidinyl]amino]-1H-benzimidazol-1-yl]methyl]phenol, 1-[(4-fluorophenyl)methyl]-6-methoxy-N-[1-[2-(2-pyrimidinylamino)ethyl]-4-piperidinyl]-1H-benzimidazol-2-amine, 1-[(4-fluorophenyl)methyl]-N-methyl-N-[1-[2-pyrimidinylamino)ethyl]-4-piperidinyl]-1H-benzimidazol-2-amine, N-(phenylmethyl)-N-[1-[2-(2-pyrimidinylamino)ethyl]-4-piperidinyl]-1H-benzimidazol-2-amine, N-[1-[2-[(5-bromo-2-pyridinyl)oxy]ethyl]-4-piperidinyl]-1-(2-furanylmethyl)-1H-benzimidazol-2-amine, 1-[(4-fluorophenyl)methyl]-N-[1-[2-[[2-(methylthio)-4-pyrimidinyl]oxy]ethyl]-4-piperidinyl]-1H-benzimidazol-2-amine, 1-[(4-fluorophenyl)methyl]-N-[1-[2-[(3-methyl-2-quinoxalinyl)oxy]ethyl]-4-piperidinyl]-1H-benzimidazol-2-amine, 1-[(4-fluorophenyl)methyl]-N-[1-[2-(2-pyrimidinyloxy)ethyl]-4-piperidinyl]-1H-benzimidazol-2-amine, N-[1-[2-[(5-bromo-2-pyridinyl)oxy]ethyl]-4-piperidinyl]-1-[(4-fluorophenyl)methyl]-1H-benzimidazol-2-amine, 1-(2-furanylmethyl)-N-[1-[2-(2-pyrimidinyloxy)ethyl]-4-piperidinyl]-1H-benzimidazol-2-amine(E)-2-butenedioate, 1-[(4-fluorophenyl)methyl]-N-[1-[2-(2-pyridinylmethoxy)ethyl]-4-piperidinyl]-1H-benzimidazol-2-amine(E)-2-butenedioate, 2-[[2-[4-[[1-[(4-fluorophenyl)methyl]-1H-benzimidazol-2-yl]amino]-1-piperidinyl]ethyl]amino]-6-propyl-4-pyrimidinol, 2-[[2-[[4-[[1-[(4-fluorophenyl)methyl]-1H-benzimidazol-2-yl]amino]-1-piperidinyl]ethyl]amino]-4-(1H)-pyrimidinone, 2-[[2-[4-[[1-[(4-fluorophenyl)methyl]-1H-benzimidazol-2-yl]amino]1-piperidinyl]ethyl]amino]-4(1H)-quinazolinone, 2-[[2-[4-[[1-[(4-fluorophenyl)methyl]-1H-benzimidazol-2-yl]amino]-1-piperidinyl]ethyl]amino]-6-(phenylmethyl)-4-(1H)-pyrimidinone, 2-[[2-[4-8 [1-[(4-fluorophenyl)methyl]-1H-benzimidazol-2-yl]amino]-1-piperidinyl]ethyl]amino]-6-methyl-4(1H)-pyrimidinone, N-[2-[4-[[1-[(4-fluorophenyl)methyl]-1H-benzimidazol-2-yl]amino]-1-piperidinyl]ethyl]-1-phthalazinamine, $N^4$-[2-[4-[[1-[(4-fluorophenyl)methyl]-1H-benzimidazol-2-yl]amino]-1-piperidinyl]ethyl]-4,5-pyrimidinediamine, N-[1-[(4-fluorophenyl)methyl]-1H-benzimidazol-2-yl]-1'-(2-pyridinyl)-[1,4'-bipiperidin]-4-amine(E)-2-butenedioate (2:3) monohydrate, N-[2-[4-[[1-[(4-fluorophenyl)methyl]-1H-benzimidazol-2-yl]amino]-1-piperidinyl]ethyl]-N'-(2-pyridinylmethyl)thiourea, N-[2-[4-[[1-[(4-fluorophenyl)methyl]-1H-benzimidazol-2-yl]amino]-1-piperidinyl]ethyl]-N'-(3-pyridinyl)thiourea, N-[2-[4-[[1-[(4-fluorophenyl)methyl]-1H-benzimidazol-2-yl]amino]-1-piperidinyl]ethyl]-N'-(2-pyridinyl)thiourea, N-(4-amino-3-pyridinyl)-N'-[2-[4-[[1-[(4-fluorophenyl)methyl]-1H-benzimidazol-2-yl]amino]-1-piperidinyl]ethyl]thiourea, N-(3-amino-2-pyridinyl)-N'-[2-[4-[[1-[(4-fluorophenyl)methyl]-1H-benzimidazol-2-yl]amino]-1-piperidinyl]ethyl]thiourea, N-(4-amino-3-pyridinyl)-N'-[2-[4-[[1-(2-furanylmethyl)-1H-benzimidazol-2-yl]amino]-1-piperidinyl]ethyl]thiourea, N-(4-amino-3-pyridinyl)-N'-[2-[4-[[1-[(4-fluorophenyl)methyl]-1H-imidazo[4,5-b]pyridin-2-yl]amino]-1-piperidinyl]ethyl]thiourea, N-(4-amino-3-pyridinyl)-N'-[2-[4-[[3-(2-pyridinylmethyl)-3H-imidazo[4,5-b]pyridin-2-yl]amino]-1-piperidinyl]ethyl]thiourea, N-(4-amino-3-pyridinyl)-N'-[2-

[4-[[3-[(4-fluorophenyl)methyl]-3H-imidazo[4,5-b]pyridin-2-yl]amino]-1-piperidinyl]ethyl]thiourea, N-[2-[4-[[1-[(4-fluorophenyl)methyl]-1H-benzimidazol-2-yl]amino]-1-piperidinyl]ethyl]-2-quinolinecarboxamide(E)-2-butenedioate, 2-chloro-N-[2-[4-[[1-[(4-fluorophenyl)methyl]-1H-benzimidazol-2-yl]amino]-1-piperidinyl]ethyl]-3-pyridinecarboxamide(E)-2-butenedioate (1:2) hemihydrate, and 6-chloro-N-[2-[4-[[1-[(4-fluorophenyl)methyl]-1H-benzimidazol-2-yl]amino]-1-piperidinyl]ethyl]-3-pyridinecarboxamide(E)-2-butenedioate; by formula I of U.S. Pat. No. 4,588,722, e.g., 1-[(4-fluorophenyl)methyl]-N-[1-[2-(4-methoxyphenyl)ethyl]-4-piperidinyl]-1H-imidazo[4,5-b]pyridin-2-amine, 1-[(4-fluorophenyl)methyl]-N-[1-[2-(4-methoxyphenyl)ethyl]-4-piperidinyl]-1H-imidazo[4,5-c]pyridin-2-amine, 3-[(4-fluorophenyl)methyl]-N-[1-[2-(4-methoxyphenyl)ethyl]-4-piperidinyl]-3H-imidazo[4,5-c]pyridin-2-amine(E)-2-butenedioate, 3-[2-[4-[[1-[(4-fluorophenyl)methyl]-1H-benzimidazol-2-yl]amino]-1-piperidinyl]ethyl]-2,4-(1H,3H)-pyrimidinedione, 3-[2-[4-[[1-(4-thiazolylmethyl)-1H-benzimidazol-2-yl]amino]-1-piperidinyl]ethyl]-2H-1-benzopyran-2-one dihydrochloride sesquihydrate, 3-[2-[4-[[3-(2-pyridinylmethyl)-3H-imidazo[4,5-b]pyridin-2-yl]amino]-1-piperidinyl]ethyl]-2H-1-benzopyran-2-one trihydrochloride dehydrate, 3-[2-[4-[[1-(2-thienylmethyl)-1H-benzimidazol-2-yl]amino]-1-piperidinyl]ethyl]-2H-1-benzopyran-2-one, 3-[2-[4-[[1-(2-pyridinylmethyl)-1H-benzimidazol-2-yl]amino]-1-piperidinyl]ethyl]-2H-1-benzopyran-2-one dihydrochloride dehydrate, 3-[2-[4-[[1-(3-pyridinylmethyl)-1H-benzimidazol-2-yl]amino]-1-piperidinyl]ethyl]-2H-1-benzopyran-2-one monohydrate, 3-[2-[4-[[1-(2-thienylmethyl)-1H-benzimidazol-2-yl]amino]-1-piperidinyl]ethyl]-2H-1-benzopyran-2-one, N-[1-[2:(4-methoxyphenyl)ethyl]-4-piperidinyl]-1-[(2-pyrazinyl)methyl]-1H-benzimidazol-2-amine, 3-[2-[4-[[1-(2-furanylmethyl)-1H-benzimidazol-2-yl]amino]-1-piperidinyl]ethyl]-2H-1-benzopyran-2-one monohydrate, 3-[2-[4-[[3-(2-furanylmethyl)-3H-imidazo[4,5-b]pyridin-2-yl]amino]-1-piperidinyl]ethyl]-2H-1-benzopyran-2-one, 3-[2-[4-[[3-[(4-fluorophenyl)methyl]-3H-imidazo[4,5-b]pyridin-2-yl]-amino]-1-piperidinyl]ethyl]-2H-1-benzopyran-2-one monohydrate, N-[1-[2:(4-methoxyphenyl)ethyl]-4-piperidinyl]-1-[(2-pyrazinyl)methyl]-1H-benzimidazol-2-amine, 3-[2-[4-[[1-(2-furanylmethyl)-1H-benzimidazol-2-yl]amino]-1-piperidinyl]ethyl]-2H-1-benzopyran-2-one monohydrate, 3-[2-[4-[[3-(2-furanylmethyl)-3H-imidazo[4,5-b]pyridin-2-yl]amino]-1-piperidinyl]ethyl]-2H-1-benzopyran-2-one, 3-[2-[4-[[3-[(4-fluorophenyl)methyl]-3H-imidazo[4,5-b]pyridin-2-yl]-amino]-1-piperidinyl]ethyl]-2H-1-benzopyran-2-one monohydrate, N,N-diethyl-4-[1-(4-fluorophenylmethyl)-1H-benzimidazol-2-ylamino]-[1,4']-bi piperidine]-1'-carboxamide, N'''-cyano-N-[2-[4-[[1-[(4-fluorophenyl)methyl]-1H-benzimidazol-2-yl]-amino]-1-piperidinyl]ethyl-N,N'-dimethylguanidine, N'''-cyano-N-[2-[4-[[1-[(4-fluorophenyl)methyl]-1H-benzimidazol-2-yl]-amino]-1-piperidinyl]ethyl]-N'-[2-(4-morpholinyl)ethyl]guanidine monohydrate, N-[2-[4-[[1-[(4-fluorophenyl)methyl]-1H-benzimidazol-2-yl]amino]-1-piperidinyl]ethyl]-4-morpholinecarbothioamide, N-[2-[4-[[1-(4-fluorophenyl)methyl]-1H-benzimidazol-2-yl]amino]-1-piperidinyl]ethyl]-N',N'-dimethylthiourea, N,N-diethyl-N'-[2-[4-[[1-[(4-fluorophenyl)methyl]-1H-benzimidazol-2-yl]-amino]-1-piperidinyl]ethyl]thiourea, N-[2-[4-[[1-[(4-fluorophenyl)methyl]-1H-benzimidazol-2-yl]amino]-1-piperidinyl]ethyl]-N'(2-phenylethyl)thiourea (E)-2-butenedioate, N-[2-[4-[[1-[(4-fluorophenyl)methyl]-1H-benzimidazol-2-yl]amino]-1-piperidinyl]ethyl]hydrazinecarbothioamide monohydrate, 4-[[1-[(4-fluorophenyl)methyl]-1H-benzimidazol-2-yl]amino]-N-methyl-[1',4'-bipiperidine]-1'-carboxamide, N-cyclohexyl-N'-[2-[4-[[1-[(4-fluorophenyl)methyl]-1H-benzimidazol-2-yl]amino]-1-piperidinyl]ethyl]thiourea, N-[2-[4-[[1-[(4-fluorophenyl)methyl]-1H-benzimidazol-2-yl]amino]-1-piperidinyl]ethyl]-N'phenylthiourea, N-[2-[4-[1-(4-fluorophenylmethyl)-1H-benzimidazol-2-ylamino]-1-piperidinyl]ethyl]-N'(4-methoxyphenyl)thiourea, N-[4-[2-[4-[[1-[(4-fluorophenyl)methyl]-1H-benzimidazol-2-yl]amino]-1 piperidinyl]ethyl]phenyl]benzenamide monohydrochloride, and N-[4-[2-[4-[[1-[(4-fluorophenypmethyl]-1H-benzimidazol-2-yl]amino]-1-piperidinyl]ethyl]phenyl]acetamide.

Yet other analogs of astemizole are compounds according to formula I of U.S. Pat. No. 4,634,704, formula I of U.S. Pat. No. 4,689,330, formula I of U.S. Pat. No. 4,695,569, formula I of U.S. Pat. No. 4,695,575, formula XVIII of U.S. Pat. No. 4,760,074, formula III-a of U.S. Pat. No. 4,820,822, formula I of U.S. Pat. No. 4,835,161, formula I of U.S. Pat. No. 4,861,785, formula III-a of U.S. Pat. No. 4,888,426, formula I in U.S. Pat. No. 4,897,401, formula I of U.S. Pat. No. 4,908,372, formula I of U.S. Pat. No. 4,943,580, formula I of U.S. Pat. No. 4,988,689, formula I of U.S. Pat. No. 5,006,527, formula I of U.S. Pat. No. 5,008,268, formula I of U.S. Pat. No. 5,025,014, formula I of U.S. Pat. No. 5,041,448, formula I of claim 1 of U.S. Pat. No. 5,071,846, formula III-a of U.S. Reissue Pat. No. 33,833, formula I of U.S. Pat. No. 5,106,857, formula I of U.S. Pat. No. 5,126,339, formula I of U.S. Pat. No. 5,151,424, formula I of U.S. Pat. No. 5,217,980, the formula of claim 1 of U.S. Pat. No. 5,258,380, formula I of U.S. Pat. No. 5,272,150, and exemplary compounds described therein. Yet other analogs of astemizole are described in U.S. Pat. No. 5,278,165, U.S. Pat. No. 5,360,807, U.S. Pat. No. 5,380,731, U.S. Pat. No. 6,130,233 (norastemizole), and U.S. Pat. No. 7,355,051, each of which is incorporated by reference.

Clemastine

Clemastine is a sedating anti-histamine agent often provided as clemastine fumarate. Analogs of clemastine include, e.g., dephenhydramine, meclizine, clobenztropine, nchembio873-comp44 ((1S,5S)-3-[(4-chlorophenyl)-phenyl-methoxy]-8-methyl-8-azabicyclo[3.2.1]octane), AHR 209 (3-[(4-chlorophenyl)-phenylmethoxy]-1-propan-2-ylpyrrolidine hydrochloride), chlortropbenzyl, pyroxamine, AHR225 (1-butyl-3-[(4-chlorophenyl)-phenylmethoxy]pyrrolidine), AHR226 (1-tert-butyl-3-[(4-chlorophenyl)-phenylmethoxy]pyrrolidine hydrochloride), AHR211 (3-[(4-chlorophenyl)-phenylmethoxy]-1-ethylpyrrolidine hydrochloride), AHR 179 (3-[(4-chlorophenyl)-phenylmethoxy]-1-(2-methylpropyl)pyrrolidine hydrochloride), substanz NR (1-[2-[(4-chlorophenyl)-phenylmethoxy]ethyl]pyrrolidine), and NSC63285 (3-[(4-chlorophenyl)-phenylmethoxy]-N,N-diethylpropan-1-amine bromide).

Phenothiazines

By a "phenothiazine" is meant a polycyclic heterocycle including two optionally substituted benzene rings fused to one of thiazine and described by the formula:

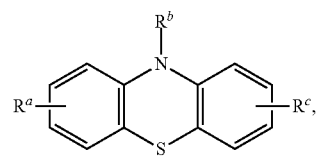

wherein each of $R^a$ and $R^e$ is, independently, selected from of H, F, Cl, Br, $CF_3$, cyano, S—$R^d$, $S(O)_2$—$R^d$, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; each $R^d$ is, independently, selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; and $R^b$ is selected from $C_{3-10}$ alkheterocyclyl and $C_{1-7}$ heteroalkyl.

Thioridazine, Prochlorperazine, Piperacetazine, and Fluphenazine

In certain embodiments, the compositions, methods, or kits of the invention employ thioridazine, prochlorperazine, piperacetazine, or fluphenazine. A related phenothiazine such as one described below may also be employed.

Thioridazine, prochlorperazine (U.S. Pat. No. 2,902,484), piperacetazine (GB Pat. No. 861,807), and fluphenazine (U.S. Pat. No. 3,058,979) have the following structures:

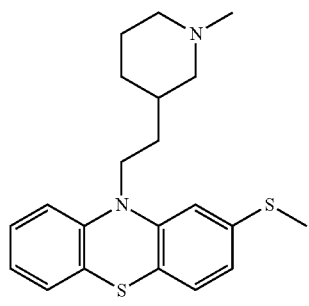

Thioridazine

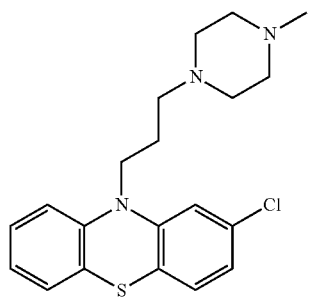

Prochlorperazine

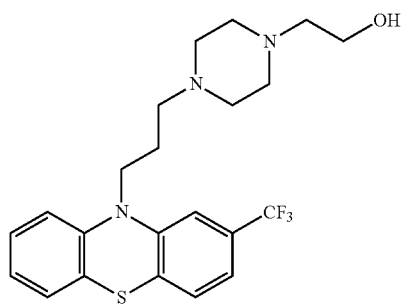

Fluphenazine

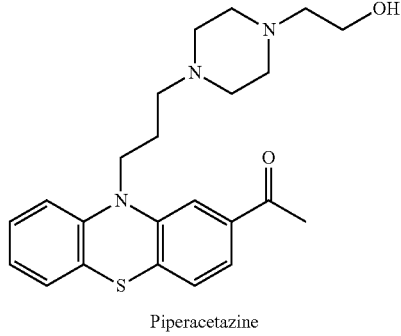

Piperacetazine

Analogs of these compounds that may be useful in the present invention include phenothiazines, which include, without limitation, acepromazine, cyamemazine, fluphenazine, mepazine, methotrimeprazine, methoxypromazine, perazine, pericyazine, perimethazine, perphenazine, pipamazine, pipazethate, piperacetazine, pipotiazine, promethazine, propionylpromazine, propiomazine, sulforidazine, thiazinaminiumsalt, thiethylperazine, thiopropazate, thioridazine, trifluoperazine, trimeprazine, thioproperazine, trifluomeprazine, triflupromazine, chlorpromazine, chlorproethazine, those compounds in PCT application WO02/057244, and those compounds in U.S. Pat. Nos. 2,415,363; 2,519,886; 2,530,451; 2,607,773; 2,645640; 2,766,235; 2,769,002; 2,784,185; 2,785,160; 2,837,518; 2,860,138; 2,877,224; 2,921,069; 2,957,870; 2,989,529; 3,058,979; 3,075,976; 3,194,733; 3,350,268; 3,875,156; 3,879,551; 3,959,268; 3,966,930; 3,998,820; 4,785,095; 4,514,395; 4,985,559; 5,034,019; 5,157,118; 5,178,784; 5,550,143; 5,595,989; 5,654,323; 5,688,788; 5,693,649; 5,712,292; 5,721,254; 5,795,888; 5,597,819; 6,043,239; and 6,569,849, each of which is incorporated herein by reference. Other structurally related phenothiazines having similar antiviral properties are also intended to be encompassed by this group.

The structures of several of the above-mentioned phenothiazines are provided below.

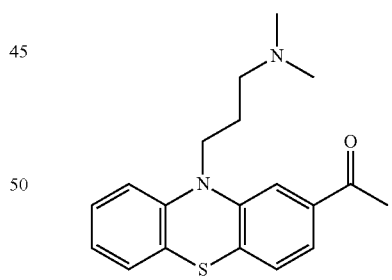

acepromazine

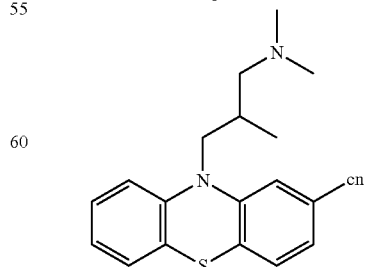

cyamemazine

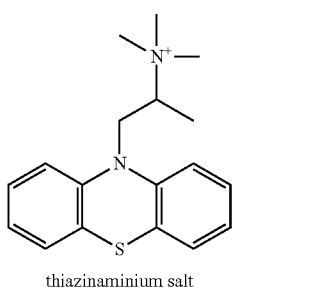
thiazinaminium salt
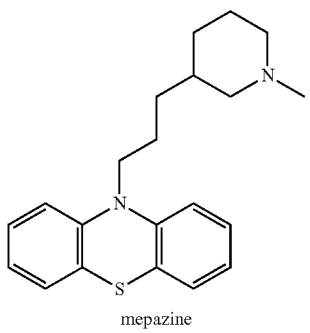
mepazine
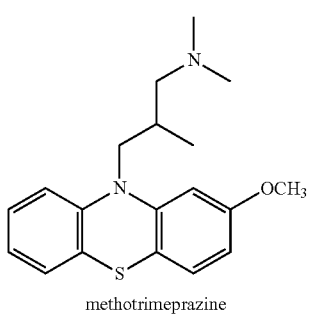
methotrimeprazine
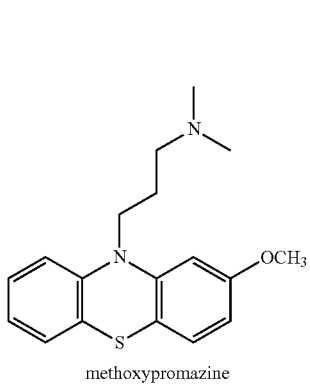
methoxypromazine
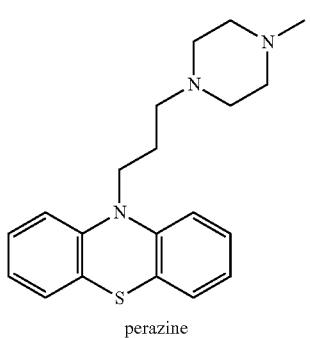
perazine
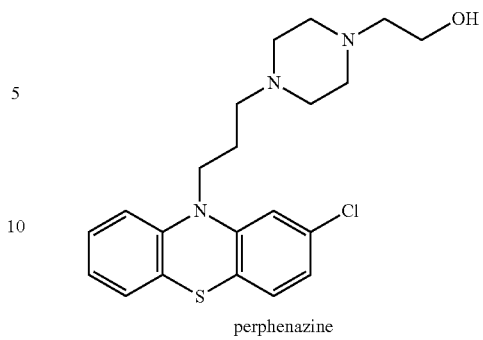
perphenazine
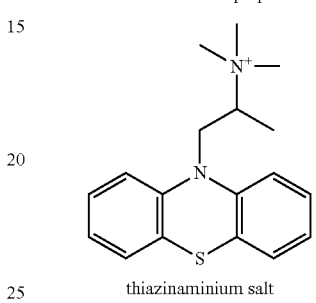
thiazinaminium salt
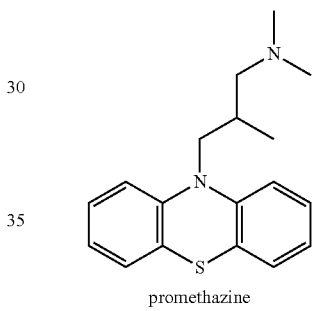
promethazine
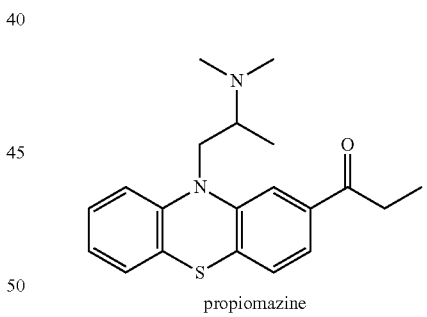
propiomazine
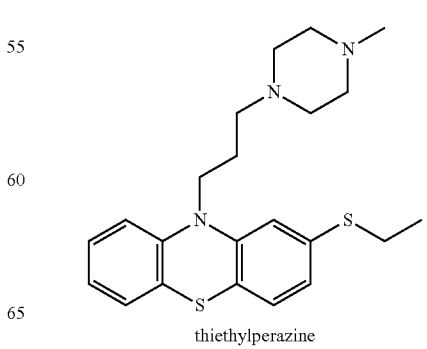
thiethylperazine -continued
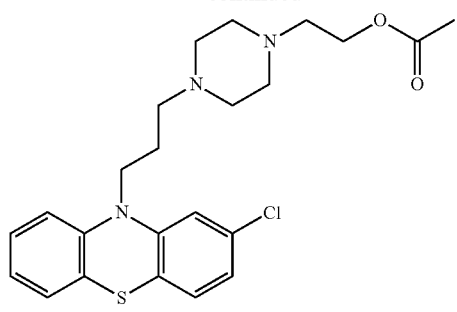
thiopropazate
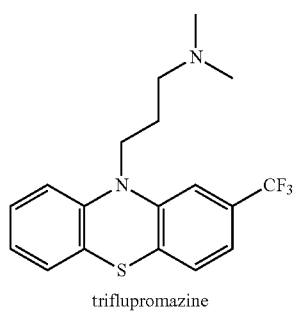
triflupromazine
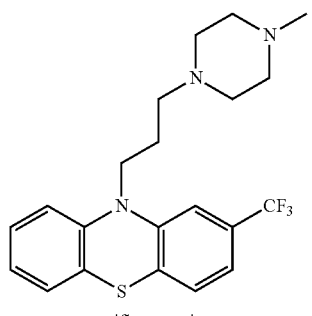
trifluoperazine
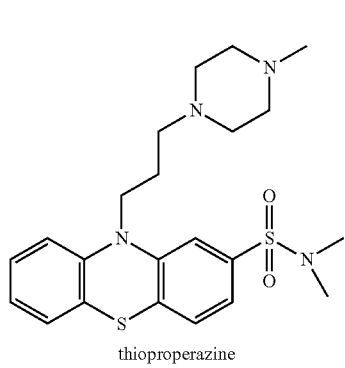
thioproperazine
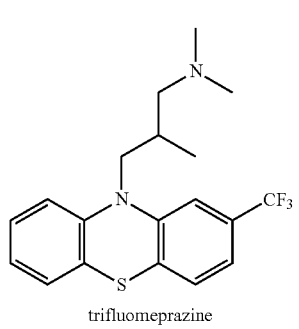
trifluomeprazine
-continued
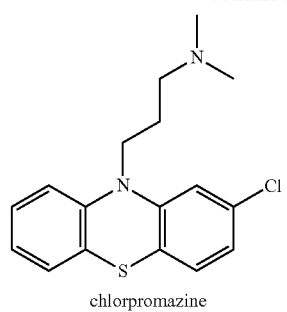
chlorpromazine
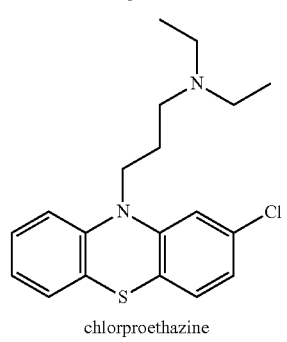
chlorproethazine
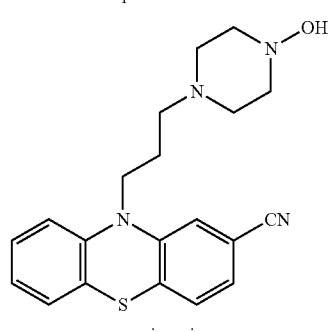
pericyazine
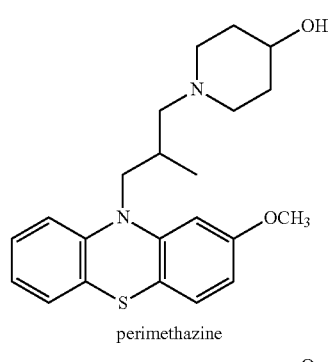
perimethazine
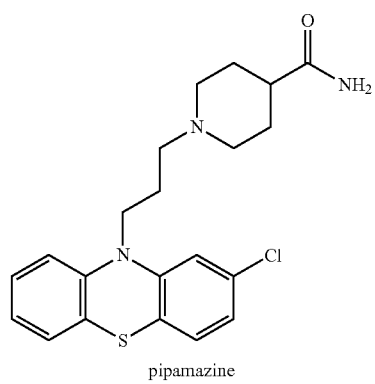
pipamazine

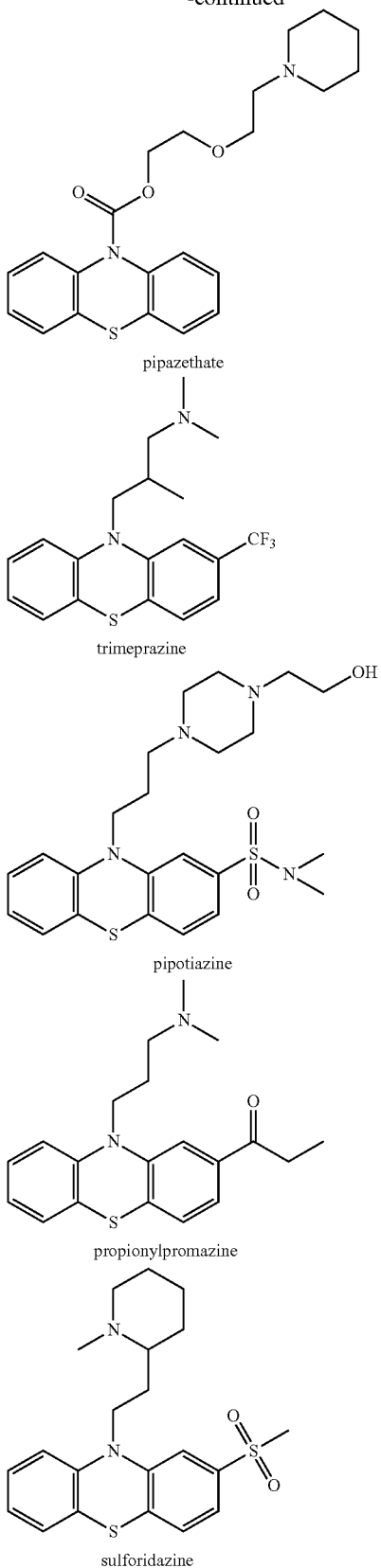

2,415,363; 2,519,886; 2,530,451; 2,607,773; 2,645640; 2,766,235; 2,769,002; 2,784,185; 2,785,160; 2,837,518; 2,860,138; 2,877,224; 2,921,069; 2,957,870; 2,989,529; 3,058,979; 3,075,976; 3,194,733; 3,350,268; 3,875,156; 3,879,551; 3,959,268; 3,966,930; 3,998,820; 4,785,095; 4,514,395; 4,985,559; 5,034,019; 5,157,118; 5,178,784; 5,550,143; 5,595,989; 5,654,323; 5,688,788; 5,693,649; 5,712,292; 5,721,254; 5,795,888; 5,597,819; 6,043,239; and 6,569,849, each of which is incorporated herein by reference.

Calcium Channel Blockers

In certain embodiments, the compositions, methods, or kits of the invention employ a calcium channel-blocking agent, e.g., lomerizine or bepridil.

Lomerizine

Lomerizine and analogs of lomerizine, e.g., 1-(2,4-dimethoxybenzyl)-4-(4-fluorobenzhydryl)-piperazine, 1-(2,4-dimethoxybenzyl)-4-[bis(4-fluorophenyl)-methyl]piperazine], and 1-(2,3,4-trimethoxybenzyl)-4-(4-fluorobenzhydryl)piperazine, are described by general formula (I) in U.S. Pat. No. 4,663,325. Other analogs include cinnamylpiperazine derivatives described by formula (I) in U.S. Pat. No. 4,703,048, such as 1-[bis(4-fluorophenyl)methyl]-4-(2,3,4-trimethoxycinnamyl)piperazine, 1-benzhydryl-4-(2,3,4-trimethoxycinnamyl)piperazine, 1-[bis(4-fluorophenyl)methyl]-4-(2,4-dimethoxycinnamyl)piperazine, and 1-benzhydryl-4-(2,4-dimethoxycinnamyl)piperazine, diene derivatives of general formula (I) described in U.S. Pat. No. 4,792,553, e.g., 1-benzhydryl-4-(5-phenyl-2,4-pentadienyl)piperazine, 1-(4,4'-difluorobenzhydryl)-4-(5-phenyl-2,4-pentadienyl)piperazine, 1-benzhydryl-4-(5-(3,4,5-trimethoxyphenyl)-2,4-pentadienyl)piperazine, 1-(4,4'-dichloro(or dibromo)benzhydryl)-4-(5-phenyl-2,4-pentadienyl)piperazine, 1-(4,4'-difluoro (or dichloro or dibromo)-benzhydryl)-4-(5-phenyl-2,4-pentadienyl)piperazine, 1-benzhydryl-4-(5-(3,4,5-triethoxyphenyl)-2,4-pentadienyl)piperazine, 1-benzhydryl-4-(5-(3,5-dimethoxy-4-hydroxy-phenyl)-2,4-pentadienyl)piperazine, 1-(4,4'-difluoro (or dichloro or dibromo)-benzhydryl)-4-(5-(3,5-dimethoxy-4-hydroxyphenyl)-2,4-pentadienyl) piperazine, 1-(4,4'-difluorobenzhydryl)-4-(5-(2,4-dimethoxyphenyl)-2,4-pentadienyl)piperazine, 1-benzhydryl-4-(5-(2,3,4-trimethoxyphenyl)-2,4-pentadienyl)piperazine, and 1-(4,4'-difluorobenzhydryl)-4-(5-(2,3,4-trimethoxyphenyl)-2,4-pentadienyl)piperazine, and indazole replacement bioisosteres of lomerizene described in U.S. Pat. No. 6,391,872.

Bepridil

Bepridil and analogs of bepridil are described by general formula (I) of U.S. Pat. No. 3,962,238. Other analogs are described by the general formula of claim 1 in U.S. Pat. No. 4,645,778, e.g., 2-(N-pyrrolidino)-3-isobutoxy-N-(3,4-methylenedioxyphenyl)-N-benzyl-propyl amine, 2-(N-pyrrolidino)-3-isobutoxy-N(2,6-dimethylphenyl)-N-benzyl-propylamine, and 2-(N-pyrrolidino)-3-isobutoxy-N-(3,4-dichlorophenyl)-N-benzyl propylamine; by formula (I) of U.S. Pat. No. 4,727,072, e.g., N-(2,6-dichlorophenyl)-beta-[[(1-methylcyclohexypmethoxy]methyl]-N-(phenyl methyl)-1-pyrrolidineethanamine, beta-[(2,2-dimethylpropoxy)methyl]-N-(3-methoxyphenyl)-N-(phenylmethyl)-1-pyrrolidineethanamine, N-(2-chlorophenyl)-beta-[(2,2-dimethylpropoxy)methyl]-N-(phenylmethyl)-1-pyrrolidineethanamine, N-(2,6-dichlorophenyl)-N-[[4-(dimethylamino)phenyl]methyl]-beta-[(2,2-dimethylpropoxy)methyl]-1-pyrrolidineethanamine, N-(2,6-dichlorophenyl)-N-[(3,4-dimethoxyphenyl)methyl]-beta-[(2,2-dimethylpropoxy)methyl]-1-pyrrolidineethanamine, N-(2,6-dichlorophenyl)-beta-[(2,2-dimethylpropoxy)methyl]-N-(phenylmethyl)-1-pyrrolidineethanamine, N-(2,6-dichlorophenyl)-beta-[(2,2-dimethylpropoxy)methyl]-N-(4-pyridinylmethyl)-1-pyrrolidineethanamine, N-(2,6-

Phenothiazine compounds can be prepared using, for example, the synthetic techniques described in U.S. Pat. Nos.

dimethylphenyl)-beta-[(2,2-dimethylpropoxy)methyl]-N-(phenylmethyl)-1-pyrrolidineethanamine, beta-[(2,2-dimethylpropoxy)methyl]-N-(phenylmethyl)-N-[3-(trifluoromethyl)phenyl]-1-pyrrolidineethanamine, beta-[(2,2-dimethylpropoxy)methyl]-N-phenyl-N-(phenylmethyl)-1-pyrrolidinee thanamine, N-(cyclohexylmethyl)-N-(2,6-dichlorophenyl)-beta-[(2,2-dimethylpropoxy)methyl]-1-pyrrolidineethanamine, and N-(2,6-dichlorophenyl)-beta-[(1,1-dimethylethoxy)methyl]-N-(phenylmethyl)-1-pyrrolidineethanamine; by the formula of claim 1 or the compound 2-diethylamino-3-isobutoxy-N-phenyl-N-2-furanyl-methyl-propylamine described in U.S. Pat. No. 4,923,889, e.g., 2-(N-pyrrolidino)-3-isobutoxy-N-phenyl-N-(4-methoxy-benzyl)propylamine, 2-diethylamino-3-isobutoxy-N-phenyl-N-2-furanyl-methyl-propylamine, and 2-(N-pyrrolidino)-3-isoamyloxy-N-phenyl-N-(4-methoxy-benzyl)propylamine; by the formula of claim 1 in U.S. Pat. No. 4,927,834, e.g., 2-(N-pyrrolidino)-3-methallyloxy-N-benzyl-N-(3,4-dioxymethylenephenyl)-propylamine, 2-(N-pyrrolidino)-3-methallyloxy-N-phenyl-N-(4-methoxy-benzyl)propylamine, 2-(N-pyrrolidino)-3-methallyloxy-N-(3-methoxy-phenyl)-N-(4-methoxy-benzyl)-propylamine, 2-(N-pyrrolidino)-3-methallyloxy-N-(4-methoxy-phenyl)-N-(4-methoxy-benzyl)-propylamine, and 2-(N-pyrrolidino)-3-isopentenyloxy-N-phenyl-N-benzyl-propylamine; by the general formula of claim 1 in U.S. Pat. No. 4,999,361, e.g., ethyl 2,2-bis-(4-methoxyphenyl)-4-(1-pyrrolidino)-5-isobutoxyvalerate, 2-phenyl-2-(2-pyridyl)-4-(1-pyrrolidino)-5-isobutoxyvaleronitrile, ethyl 2,2-diphenyl-4-(N,N-diethylamino)-5-isobutoxyvalerate, ethyl 2,2-diphenyl-4-(1-pyrrolidino)-5-benzyloxyvalerate, and ethyl 2,2-diphenyl-4-(1-pyrrolidino)-5-(2-picolyloxy)valerate.

Analogs of lomerizine and bepridil with calcium-channel blocking activity include clentiazem (U.S. Pat. No. 4,567,175), gallopamil (U.S. Pat. No. 3,261,859), mibefradil (U.S. Pat. No. 4,808,605), prenylamine (U.S. Pat. No. 3,152,173), semotiadil (U.S. Pat. No. 4,786,635), terodiline (U.S. Pat. No. 3,371,014), aranipine (U.S. Pat. No. 4,572,909), bamidipine (U.S. Pat. No. 4,220,649), benidipine (EP Patent Application Publication No. 106,275), cilnidipine (U.S. Pat. No. 4,672,068), efonidipine (U.S. Pat. No. 4,885,284), elgodipine (U.S. Pat. No. 4,962,592), lacidipine (U.S. Pat. No. 4,801,599), manidipine (U.S. Pat. No. 4,892,875), nifendipine (U.S. Pat. No. 3,485,847), nilvadipine (U.S. Pat. No. 4,338,322), flunarizine (U.S. Pat. No. 3,773,939) lidoflazine (U.S. Pat. No. 3,267,104), bencyclane (Hungarian Pat. No. 151,865), etafenone (German Pat. No. 1,265,758), and perhexyline (British Pat. No. 1,025,578).

Analogs of lomerizine with vasodilating activity may also be employed in certain embodiments of the inventions. Examples are cinnarizine, citicoline (which may be isolated from natural sources as disclosed in Kennedy et al. (*J. Am. Chem. Soc.,* 77:250 (1955)) or synthesized as disclosed in Kennedy (*J. Biol. Chem.,* 222:185 (1956)), cyclandelate (see U.S. Pat. No. 3,663,597), ciclonicate (see German Pat. No. 1,910,481), diisopropylamine dichloroacetate (see GB Pat. No. 862,248), eburnamonine (see Hermann et al., *J. Am. Chem. Soc.,* 101:1540 (1979)), fenoxedil (see U.S. Pat. No. 3,818,021), flunarizine (see U.S. Pat. No. 3,773,939), nafronyl (see U.S. Pat. No. 3,334,096), nicametate (Blicke et al., *J. Am. Chem. Soc.* 64:1722 (1942)), nimodipine (see U.S. Pat. No. 3,799,934), papaverine (see Goldberg, *Chem. Prod. Chem. News* 17:371 (1954)); tinofedrine (see U.S. Pat. No. 3,563,997), and viquidil (see U.S. Pat. No. 2,500,444).

Selective Serotonin Reuptake Inhibitors

Selective serotonin reuptake inhibitors may be employed in certain embodiments of the invention. By "selective serotonin reuptake inhibitor" or "SSRI" is meant any member of the class of compounds that (i) inhibit the uptake of serotonin by neurons of the central nervous system, (ii) have an inhibition constant (Ki) of 10 nM or less, and (iii) a selectivity for serotonin over norepinephrine (i.e., the ratio of $K_i$ (norepinephrine) over $K_i$ (serotonin)) of greater than 100. SSRIs that may be particularly useful are paroxetine, sertraline, and UK-416244.

Paroxetine

Paroxetine is an SSRI described in U.S. Pat. No. 3,912,743. Non-limiting examples of paroxetine analogs are compounds described by formula IV of U.S. Pat. No. 4,485,109, e.g., 4-phenyl-a,a,1-trimethyl-4-piperidinemethanol; (−)-trans-4-(4-fluorophenyl)-3-(4-methoxyphenoxy)methylpiperidine and (−)-trans-4-(4-fluorophenyl)-3-[(4-methoxyphenoxy)methyl]-1-methylpiperidine, described in U.S. Pat. No. 4,585,777 and U.S. Pat. No. 4,593,036, respectively; compounds described by formula I of U.S. Pat. No. 4,985,446, e.g., (−)-trans-4-(−4-fluorophenyl)-3-(3,4-methylenedioxyphenoxymethyl)-1-(2-methoxymethyl)-piperidine hydrochloride, (−)-trans-1-ethyl-4-(4-fluorophenyl)-3-(4-methoxyphenoxy-methyl)-piperidine hydrochloride, trans-1-ethyl-4-(4-fluorophenyl)-3-(4-t-butylphenoxymethyl)-piperidine hydrochloride, and trans 3-(4-benzyloxyphenoxymethyl)-4-(4-fluorophenyl)-1-methylpiperidine; compounds of formula I in U.S. Pat. No. 5,019,582, e.g., (−)-trans-4-(−4-fluorocyclopentyl)-3-(3,4-methylenedioxyphenoxymethyl)-1-p entylpiperidine hydrochloride, (+)-trans-4-phenyl-3-(3,4-methylenedioxyphenoxymethyl)-1-pentylpiperidine hydrochloride, (−)-trans-4-(−4-fluorophenyl)-3-(4-methoxyphenoxymethyl)-1-pentylpiperidine hydrochloride, (−)-trans-4-(−4-fluorophenyl)-3-(5,6,7,8-tetrahydro-2-naphthoxymethyl)-1-pentylpiperidine hydrochloride, (−)-trans-4-(4-fluorophenyl)-3-(3,4-methylenedioxyphenoxymethyl)-1-pentylpiperidine, and (−)-trans-4-(4-fluorophenyl)-3-(3,4-methylenedioxyphenoxymethyl)-1-pentylpiperidinee hydrochloride; compounds of formula I of U.S. Pat. No. 5,158,961, e.g., (−)-trans-4-(4-methoxyphenyl)-3-(3,4-methylenedioxyphenoxymethyl)-1-pentyl piperidine oxalate, (+)-trans-4-(4-methoxyphenyl)-3-(3,4-methylenedioxyphenoxymethyl)-1-pentyl-piperidine oxalate, (+/−)-trans-3-(3,4-methylenedioxyphenoxymethyl)-1-pentyl-4-(3-trifluoromethylphenyl)piperidine hydrochloride, (+)-trans-3-(2-bromo-4,5-methylenedioxyphenoxymethyl)-4-(4-fluorophenyl)-1-pentylpiperidine hydrochloride, and (+/−)-trans-3-(3,4-methylenedioxyphenoxymethyl)-1-pentyl-4-(4-pentyloxyphenyl)piperidine hydrochloride; and compounds of formula I of U.S. Pat. No. 5,328,917, e.g., 1-butyl-3-(4-methoxybenzylaminomethyl)-4-phenylpiperidine, 1-butyl-3-(4-trifluoromethylphenylaminomethyl)-4-phenylpiperidine, and (−) trans-1-butyl-3-(2-phenylethylaminomethyl)-4-phenylpiperidine.

Sertraline

In certain embodiments, sertraline or an analog thereof can be used in the compositions, methods, and kits of the invention. Sertraline has the structure:

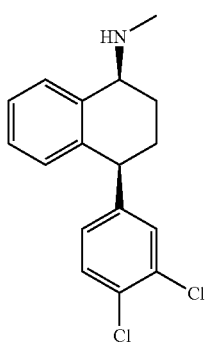 [SMILES: CN[C@H]1CC[C@@H](c2ccc(Cl)c(Cl)c2)c2ccccc21]

Structural analogs of sertraline include those having the formula:

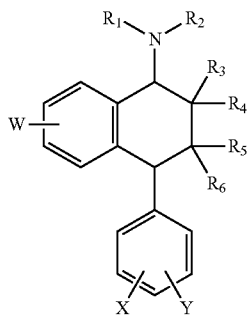

where $R_1$ and $R_2$ are independently selected from the group consisting of H, optionally substituted $C_{1-6}$ alkyl (e.g., $CH_3$, $(CH_2)_xOH$, cyclopropyl, $(CH_2)_xCOOH$, or $CH_2CHOH(CH_2)_x$, $(CH_2)_xN(CfH_3)_2$, where x is 1, 2, 3, 4, or 5), and optionally substituted $C_{1-7}$ heteroalkyl (e.g., $CH_2CH_2N(CH_3)_2$) or $R_1$ and $R_2$ together form a $C_{3-8}$ cycloalkyl optionally heterocyclic, optionally substituted (e.g., forming a morpholine ring), $R_3$, $R_4$, $R_5$, and $R_6$ are independently H, Cl, F, Br, OH, or optionally substituted $C_{1-6}$ alkyl; X and Y are each selected from the group consisting of H, F, Cl, Br, $CF_3$, $C_{1-6}$ alkoxy (e.g., OPh and $OCH_3$), and cyano; and W is selected from the group consisting of H, F, Cl, Br, $CF_3$, $C_{1-3}$ alkoxy, COOH, $CH_2CH_2OH$, NHCOH, $NHCOCH_3$, $CH_2S(O)_nCH_3$, $CH_2NH_2$, $CONH_2$, $CH_2OH$, NHCOPh, $CH_2NHS(O)_nCH_3$, $NHS(O)_nPh$, $N(CH_3)_2$, $S(O)_nNH_2$, NHCOBu, $NHS(O)_nCH_3$, NHCOcyclopentyl, CN, $NHS(O)_n$cyclopropyl, $NH_2$, $NO_2$, I, $SO_2N(CH_3)_2$, $SO_2NHMe$, $SO_2NHCH_2CH_2OH$, $CO_2Me$, $NHSO_2Bu$, $CONHCH_3$, $CH_2NHCOCH_3$, CONHPh,

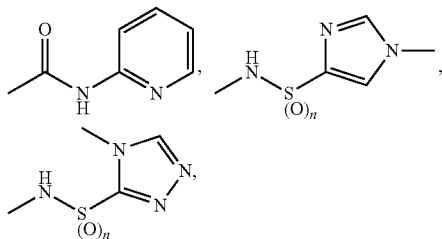

CONHcylopropyl, $C(S)NH_2$, $NHC(S)CH_3$, $CONHCH_2COOCH_3$, $CONHCH_2COOH$, $CONHCH_2$cyclopropyl, CONHcyclobutyl, NHCOcyclopropyl, $NH(CH_3)COCH_3$, and $CH_2S(O)_nR_{11}$, where n is 0, 1, or 2 and $R_{11}$ is phenyl, $C_{2-6}$ heterocyclyl, optionally substituted $C_{1-8}$ alkyl (e.g., $C_{4-8}$ unsubstituted alkyl such as Bu or $C_{3-8}$ substituted alkyl). In certain embodiments, $R_1$ is $CH_3$ and $R_2$ is $CH_3$, $CH_2CH_2OH$, cyclopropyl, $CH_2COOH$, $CH_2CH_2NH_2$, $CH_2CH(OH)R_8$, or $CH_2CH(R_8)NR_9R_{10}$, where n is 0, 1, or 2 and $R_8$, $R_9$, and $R_{10}$ are independently H or $C_{1-6}$ alkyl. In certain embodiments, X is H and Y is p-OPh, p-$OCF_3$, o-$OCH_3$ m-$OCH_3$, or p-$OCH_3$. In certain embodiments of the above structure, the sertraline analog has the formula:

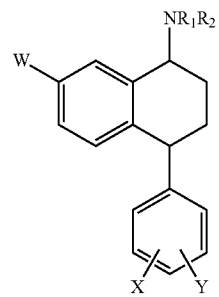

Other sertraline analogs have the formula:

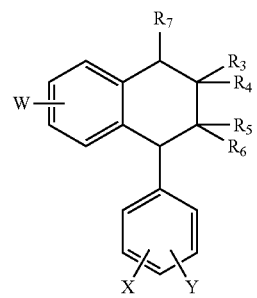

where $R_3$, $R_4$, $R_5$, $R_6$, W, X, and Y are as defined above, and $R_7$ is independently H, $NH(CH_2)_mCH_3$, $O(CH_2)_mCH_3$, OH, $O(CH_2)_mCH_3$, =O, $C_{1-6}$ alkyl (e.g., isopropyl), or $C_{1-6}$ alkyoxy, where in is 0, 1, 2, 3, 4, 5, or 6. In certain embodiments, $R_3$, $R_4$, $R_5$, and $R_6$ are H; X and Y are each Cl at the 3 and 4 positions of the benzyl ring. Exemplary analogs include:

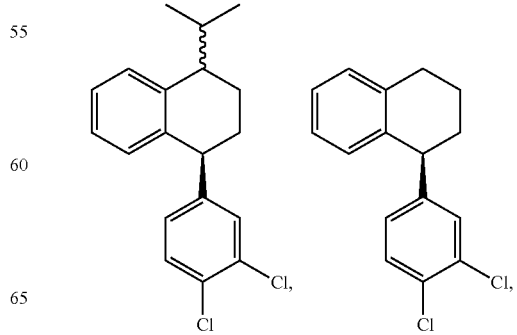

-continued

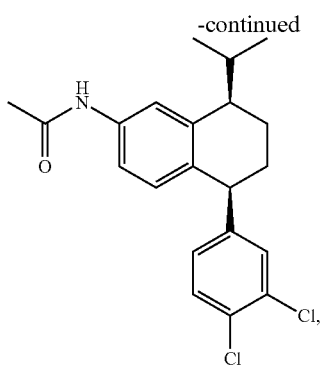

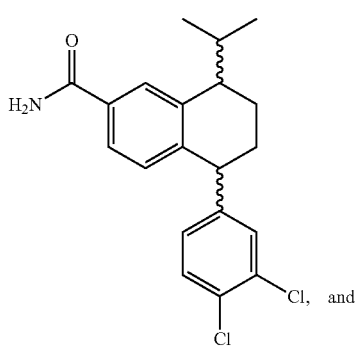

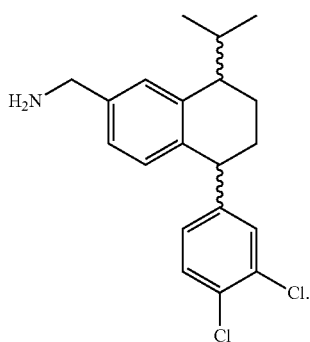

Other sertraline analogs have the formula:

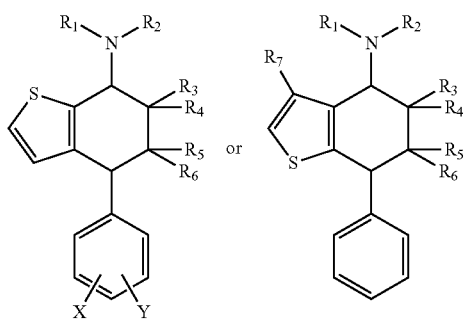

where $R_1$, $R_2$, $R_3$, $R_4$, $R_5$, $R_6$, X and Y are as defined above, and $R_7$ is H or $C_{1-6}$ optionally substituted alkyl. Other sertraline analogs are described by the formula:

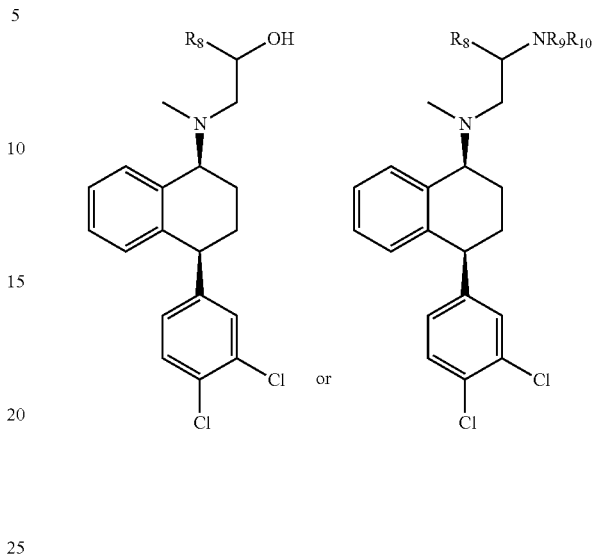

wherein $R_8$, $R_9$, and $R_{10}$ are independently H, optionally substituted $C_{1-6}$ alkyl (e.g., $CH_3$, $(CH_2)_xOH$, cyclopropyl, $(CH_2)_xCOOH$, or $CH_2CHOH(CH_2)_x$, $(CH_2)_xN(CH_3)_2$, where x is 1, 2, 3, 4, or 5), and optionally substituted $C_{1-7}$ heteroalkyl (e.g., $CH_2CH_2N(CH_3)_2$).

In certain embodiments, sertraline analogs are in the cis-isomeric configuration. The term "cis-isomeric" refers to the relative orientation of the $NR_1R_2$ and phenyl moieties on the cyclohexene ring (i.e., they are both oriented on the same side of the ring). Because both the 1- and 4-carbons are asymmetrically substituted, each cis-compound has two optically active enantiomeric forms denoted (with reference to the 1-carbon) as the cis-(1R) and cis-(1S) enantiomers. Sertraline analogs are also described in U.S. Pat. No. 4,536,518. Other related compounds include (S,S)-N-desmethylsertraline, rac-cis-N-desmethylsertraline, (1S,4S)-desmethyl sertraline, 1-des(methylamine)-1-oxo-2-(R,S)-hydroxy sertraline, (1R, 4R)-desmethyl sertraline, sertraline sulfonamide, sertraline (reverse) methanesulfonamide, 1R,4R sertraline enantiomer, N,N-dimethyl sertraline, nitro sertraline, sertraline aniline, sertraline iodide, sertraline sulfonamide $NH_2$, sertraline sulfonamide ethanol, sertraline nitrile, sertraline-CME, dimethyl sertraline reverse sulfonamide, sertraline reverse sulfonamide ($CH_2$ linker), sertraline B-ring ortho methoxy, sertraline A-ring methyl ester, sertraline A-ring ethanol, sertraline N,N-dimethylsulfonamide, sertraline A-ring carboxylic acid, sertraline B-ring para-phenoxy, sertraline B-ring para-trifluoromethane, N,N-dimethyl sertraline B-Ring para-trifluoromethane, sertraline A-ring methyl sulfoxide ($CH_2$ linker), sertraline A-ring carboxamide, sertraline A-ring reverse carboxamide, Sertraline A-ring methanamine, sertraline A-ring sulfonylmethane ($CH_2$ linker), sertraline (reverse) methanesulfonamide, sertraline A-ring thiophene, reduced sulfur sertraline A-ring methyl sulfoxide ($CH_2$ linker), and heterocyclic substituted stertraline (reverse) methanesulfonamide. Structures of these analogs are shown in Table 4.

TABLE 4
Sertraline analogs.
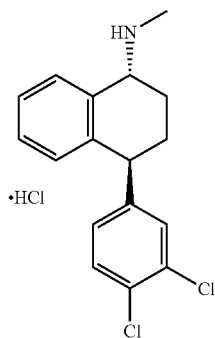
(1R,4S) Sertraline Hydrochloride
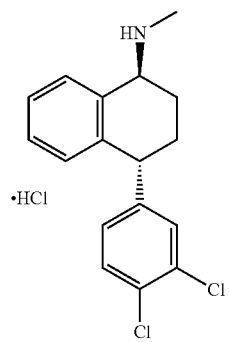
(1S,4R) Sertraline Hydrochloride
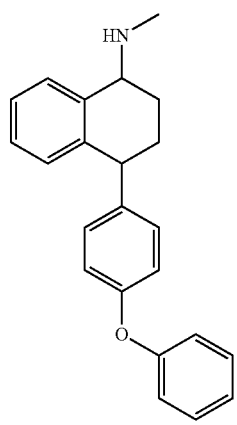
Sertraline B-Ring Para-Phenoxy
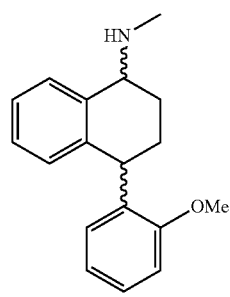
Sertraline B-Ring Ortho-Methoxy
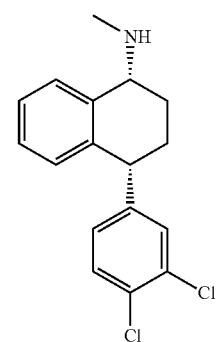
1R,4R Sertraline Enantiomer
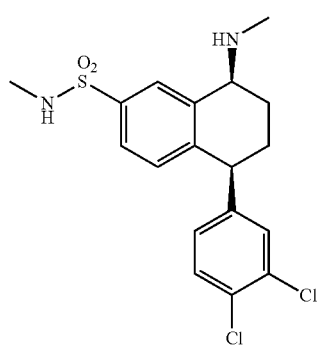
Sertraline Sulfonamide
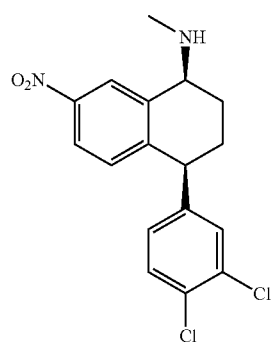
Nitro Sertraline
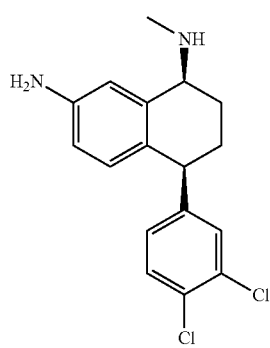
Sertraline Aniline TABLE 4-continued
Sertraline analogs.
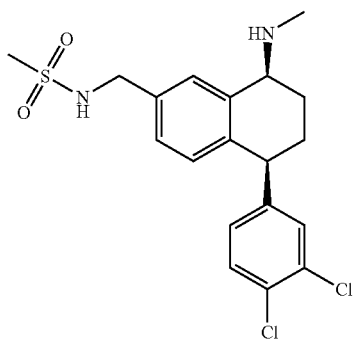
Sertraline Reverse Sulfonamide (CH2 linker)
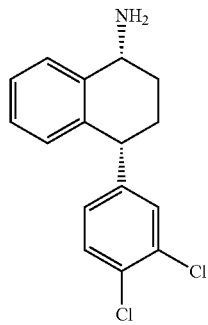
(1R,4R)-Desmethyl Sertraline
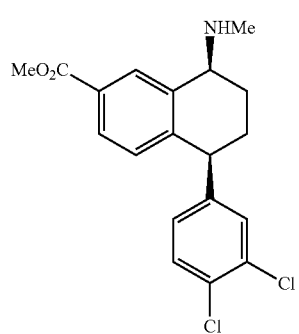
Sertraline A-Ring Methyl Ester
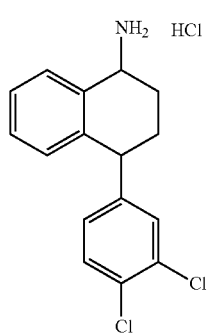
rac-cis-N-Desmethyl Sertraline, Hydrochloride
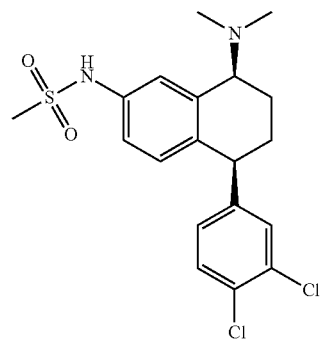
Dimethyl Sertraline Reverse Sulfonamide
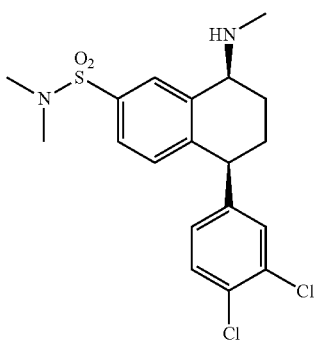
Sertraline N,N-Dimethylsulfonamide
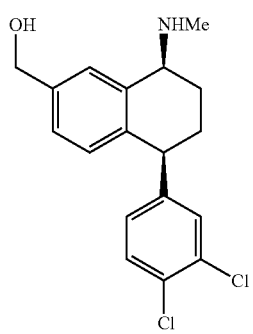
Sertraline A-ring Ethanol
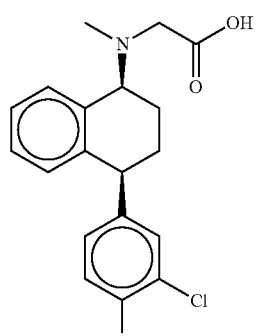
Sertraline-CME TABLE 4-continued
Sertraline analogs.
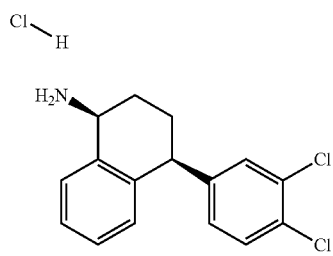
(1S,4S)-Desmethyl Sertraline, Hydrochloride
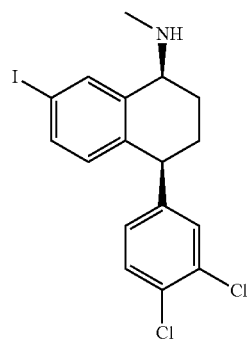
Sertraline Iodide
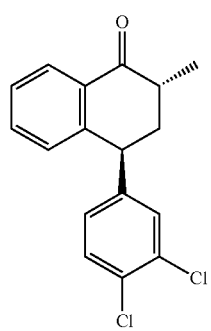
1-Des(methylamine)-1-oxo-2-(R,S)-hydroxy Sertraline
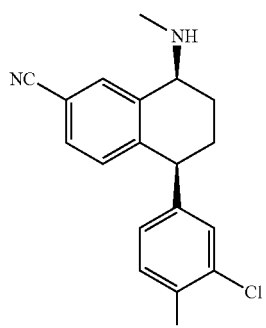
Sertraline Nitrile
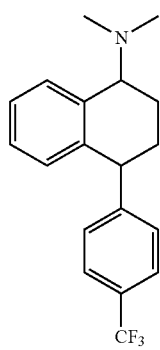
N,N-Dimethyl Sertraline B-Ring Para-Trifluoromethane
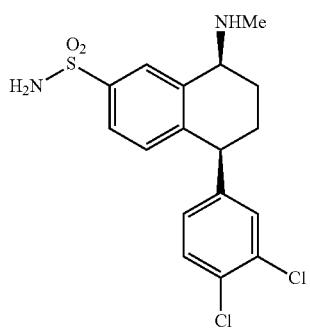
Sertraline Sulfonamide NH$_2$
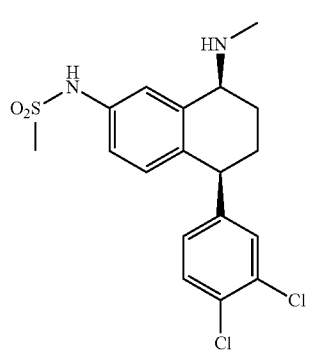
Sertraline (Reverse) Methanesulfonamide
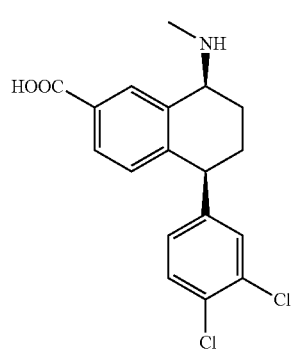
Sertraline A-Ring Carboxylic Acid TABLE 4-continued
Sertraline analogs.
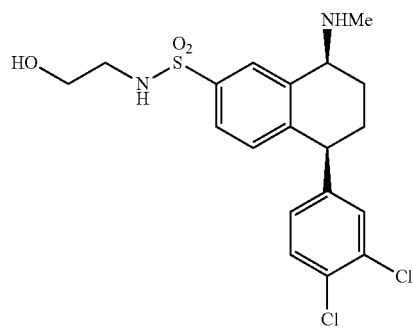
Sertraline Sulfonamide Ethanol
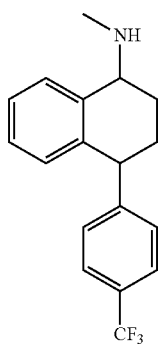
Sertraline B-Ring Para-Trifluoromethane
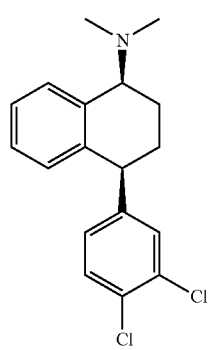
N,N-Dimethyl Sertraline
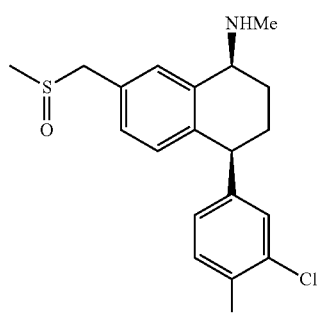
Sertraline A-ring Methyl Sulfoxide
(CH$_2$ Linker)
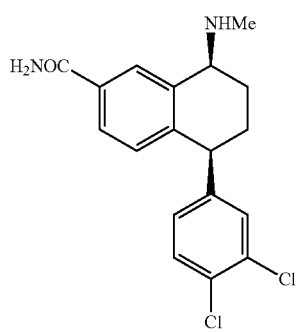
Sertraline A-ring carboxamide
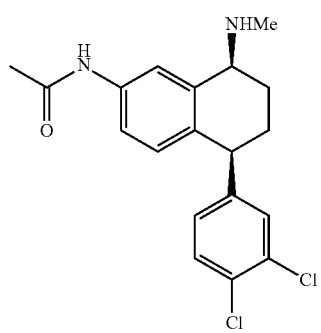
Sertraline A-ring reverse carboxamide
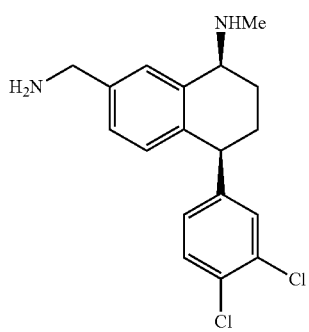
Sertraline A-Ring methanamine
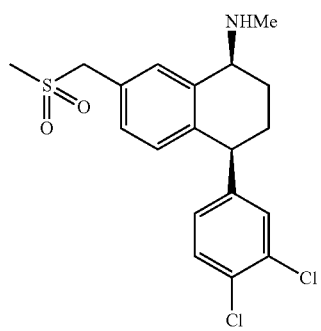
Sertraline A-ring Sulfonylmethane
(CH$_2$-Linker)

TABLE 4-continued
Sertraline analogs.
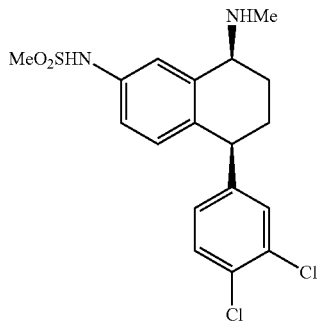
Sertraline (Reverse) Methanesulfonamide
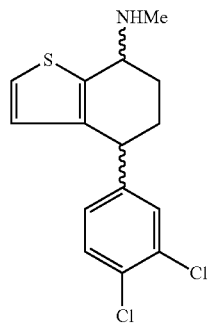
Sertraline A-ring Thiophene
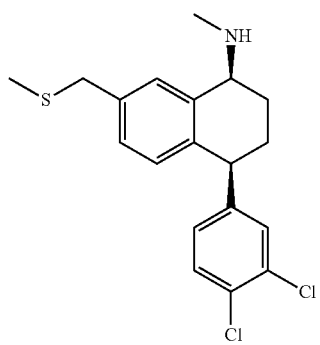
Sertraline A-ring Methylsulfide
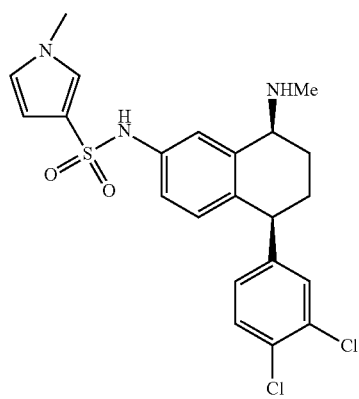
Sertraline A-ring Methylimidazole Reverse Sulfonamide
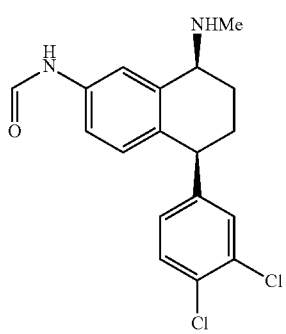
Sertraline A-ring reverse formamide
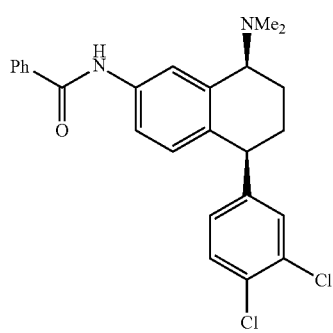
N,N-Dimethyl Sertraline A-ring Reverse benzamide TABLE 4-continued
Sertraline analogs.
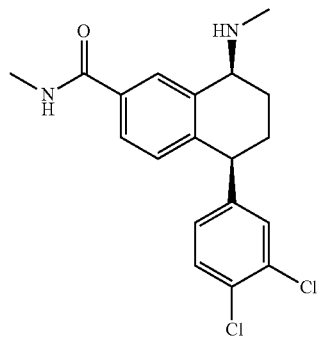
Sertraline A-ring Methylcarboxamide
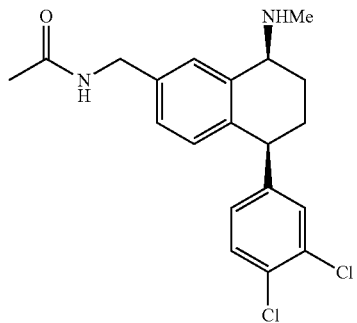
Sertraline A-ring Reverse Carobxamide
(CH₂ linker)
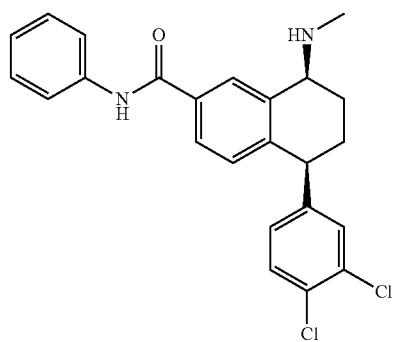
Sertraline A-ring Benzamide
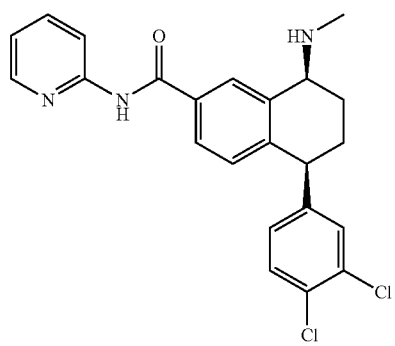
Sertraline A-ring Pyridine Carboxamide
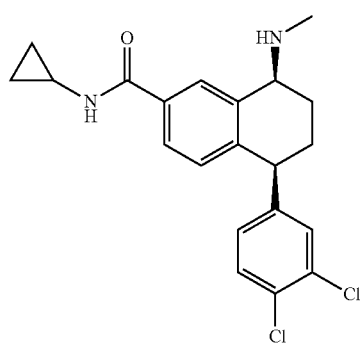
Sertraline cyclopropyl carboxamide
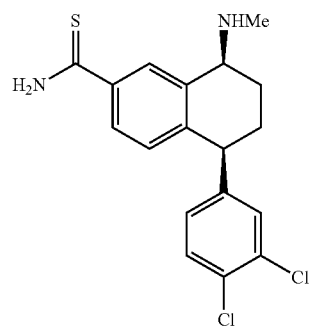
Sertraline A-Ring Thiocarboxamide TABLE 4-continued
Sertraline analogs.
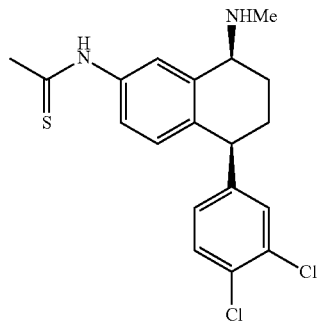
Sertraline A-ring Reverse Thiocarboxamide
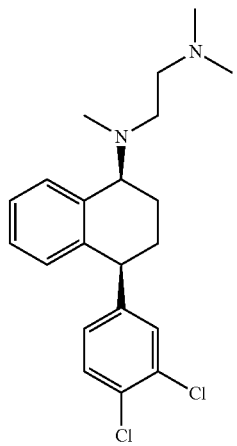
N-methyl,N-CH$_2$CH$_2$N(CH$_3$)$_2$ Sertraline
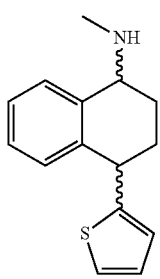
Sertraline B-ring 2-thiophene
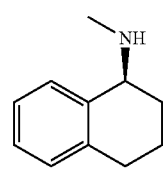
Sertraline without B-ring
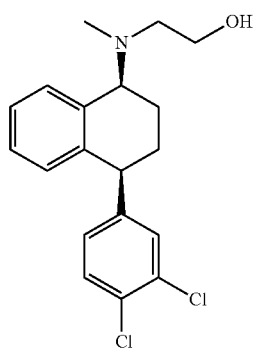
N-ethanol Sertraline
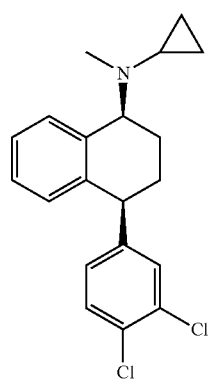
N-cyclopropyl Sertraline TABLE 4-continued
Sertraline analogs.
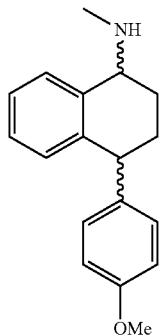
Sertraline B-ring p-methoxy
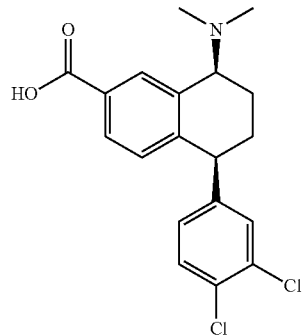
N,N-dimethyl Sertraline A-ring Carboxylic Acid
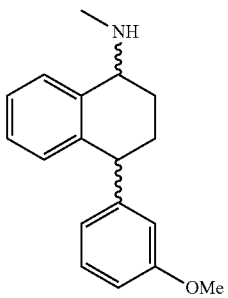
Sertraline B-ring m-Methoxy
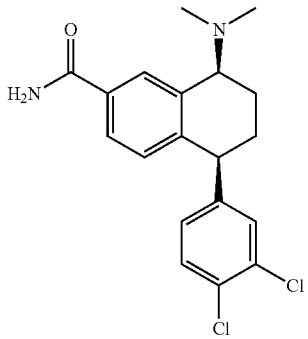
N,N-Dimethyl Sertraline A-ring Carboxamide
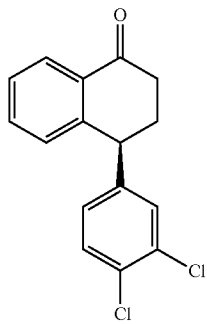
4S-Sertraline Ketone
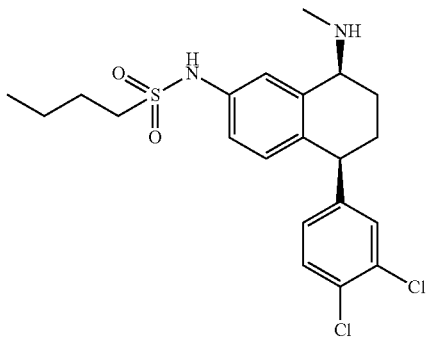
Sertraline A-Ring Butane Reverse Sulfonamide
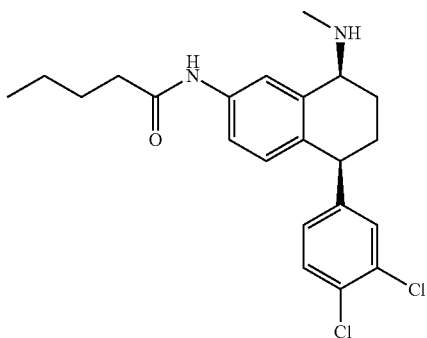
Sertraline A-Ring Reverse Pentanamide
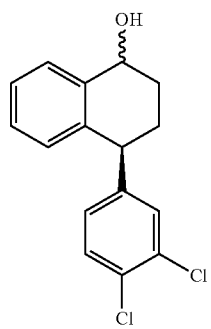
Alcohol Sertraline TABLE 4-continued Sertraline analogs.

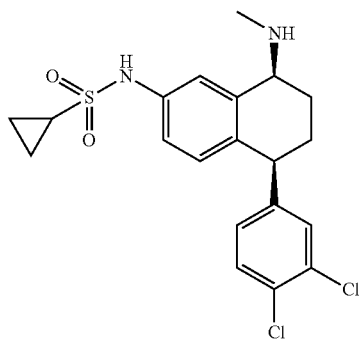

Sertraline A-ring Cyclopropane Reverse Sulfonamide

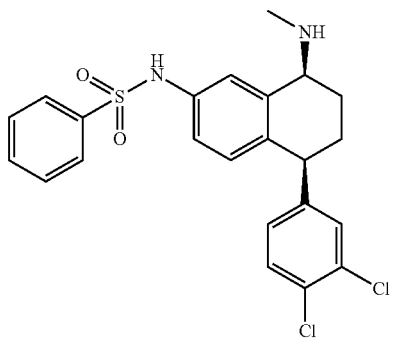

Sertraline A-ring Benzene Reverse Sulfonamide

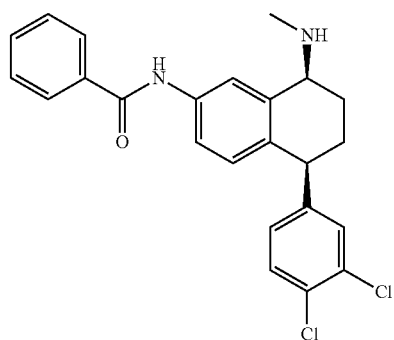

Sertraline A-Ring Reverse Benzamide

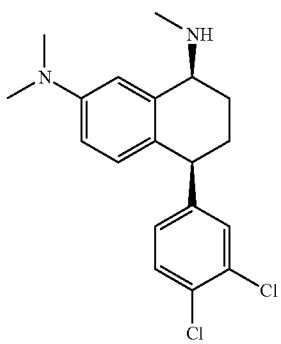

Sertraline A-Ring N,N-Dimethylamine

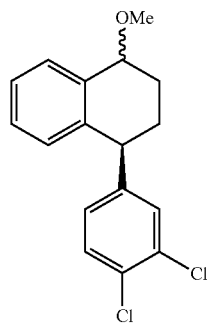

Methoxy 4S-Sertraline

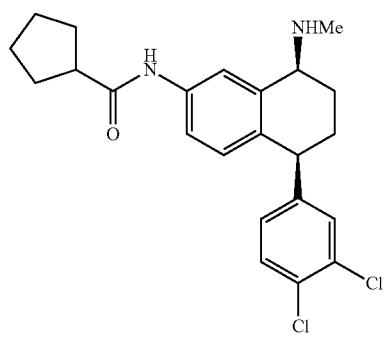

Sertraline A-Ring Reverse cyclopentanecarboxamide

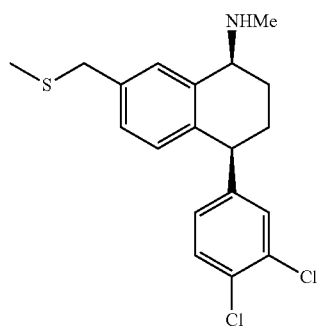

Sertraline A-Ring Methyl sulfide

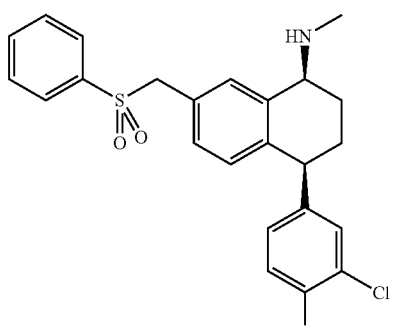

Sertraline A-Ring Phenylsulfone (CH$_2$ linker)

TABLE 4-continued

Sertraline analogs.

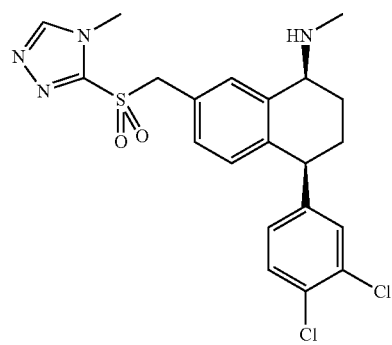

Sertraline A-Ring Methyltriazolesulfone
(CH₂ linker)

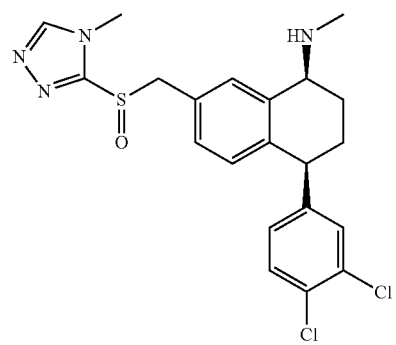

Sertraline A_Ring Methyltriazolesulfoxide
(CH₂ linker)

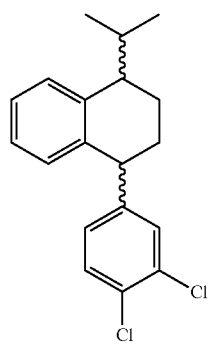

Isopropyl Sertraline

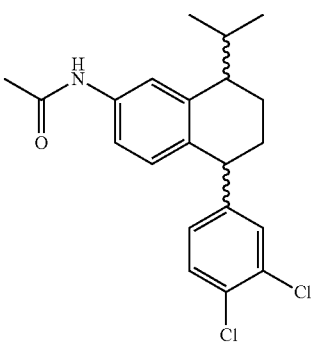

Isopropyl Sertraline reverse carboxamide

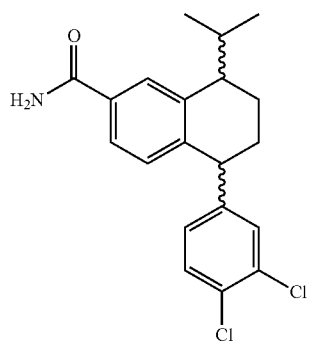

Isopropyl Sertraline carboxamide

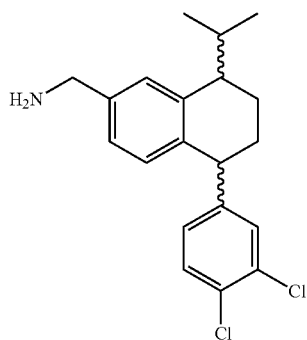

Isopropyl Sertraline methanamine

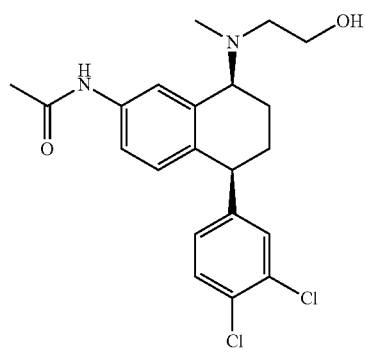

N-ethanol Sertraline A-ring reverse
carboxamide

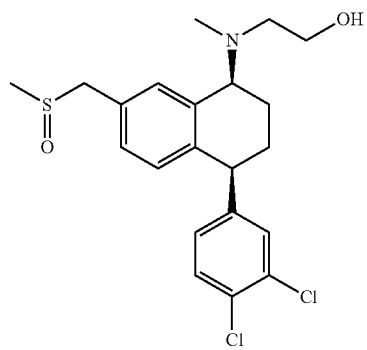

N-ethanol Sertraline A-ring sulfoxide
(CH₂ linker)

TABLE 4-continued
Sertraline analogs.
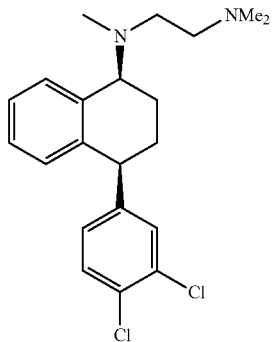
N-(N,N-dimethyl)ethyl Sertraline
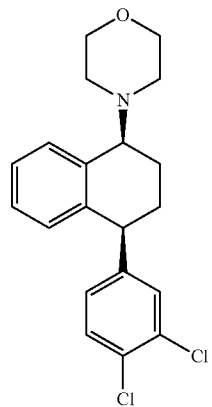
N-morpholine Sertraline
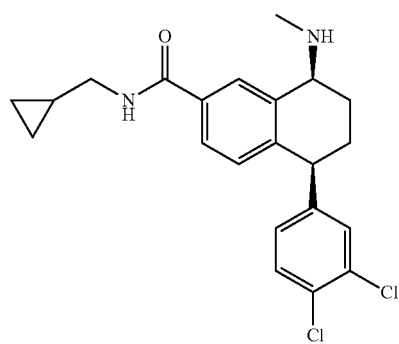
Sertraline cyclopropyl (CH2 linker) carboxamide
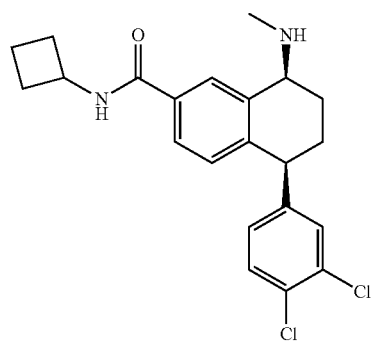
Sertraline cyclobutyl carboxamide
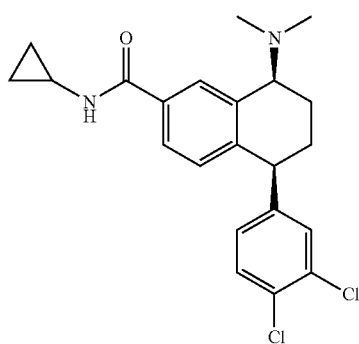
N,N-dimethyl Sertraline cyclopropyl carboxamide
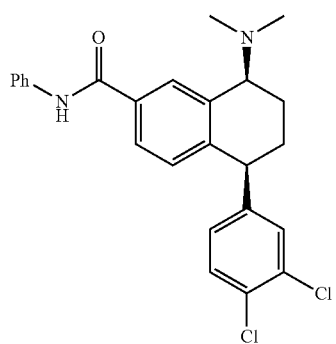
N,N-dimethyl Sertraline phenylcarboxamide TABLE 4-continued Sertraline analogs.

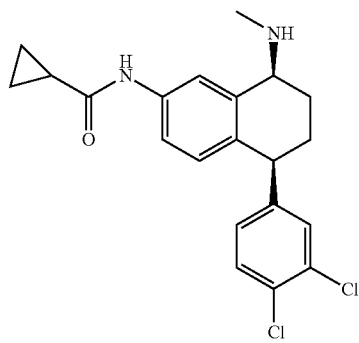
Sertraline reverse cyclopropyl carboxamide

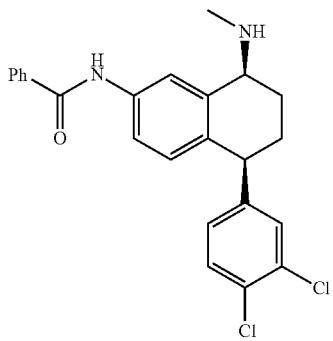
Sertraline reverse phenylcarboxamide

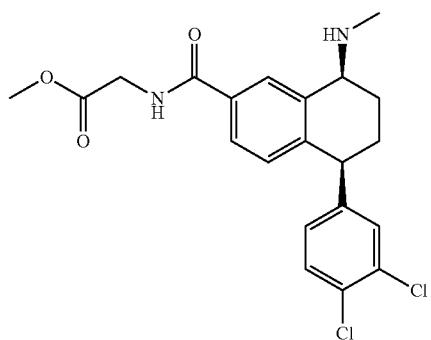
Sertraline A-Ring Methyl Acetate Carboxamide

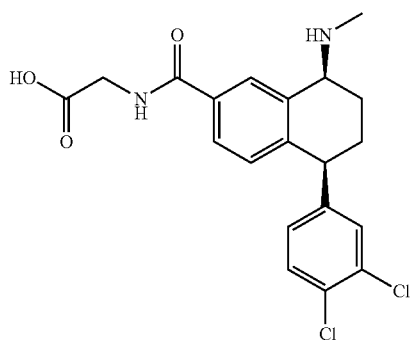
Sertraline A-Ring Acetic Acid Carboxamide

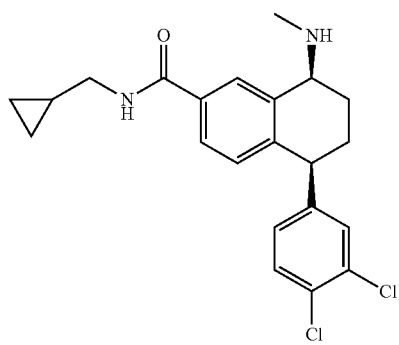
Sertraline A-Ring Cyclopropyl Carboxamide (CH$_2$ linker)

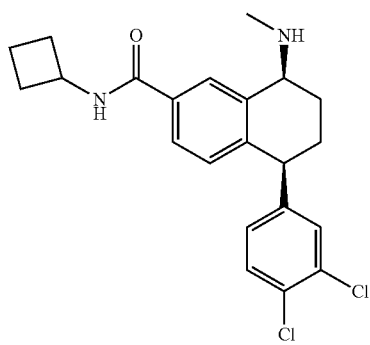
Sertraline A-Ring Cyclobutyl Carboxamide

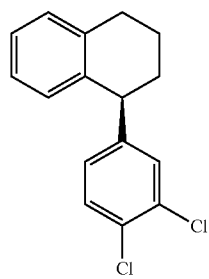
No-N Sertraline

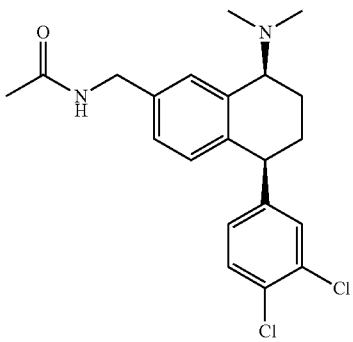
N,N Dimethyl Sertraline A-Ring Reverse Carboxamide (CH$_2$ linker)

TABLE 4-continued

Sertraline analogs.

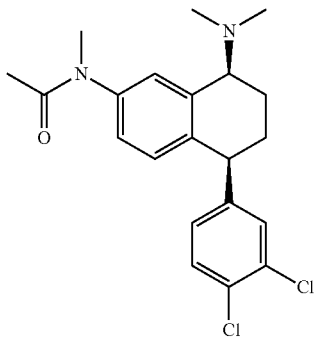

Sertraline A-ring N-methyl reverse carboxamide

Particularly useful are the following compounds, in either the (1S)-enantiomeric or (1S)(1R) racemic forms, and their pharmaceutically acceptable salts: cis-N-methyl-4-(3,4-dichlorophenyl)-1,2,3,4-tetrahydro-1-naphthalenamine; cis-N-methyl-4-(4-bromophenyl)-1,2,3,4-tetrahydro-1-naphthalenamine; cis-N-methyl-4-(4-chlorophenyl)-1,2,3,4-tetrahydro-1-naphthalenamine; cis-N-methyl-4-(3-trifluoromethyl-phenyl)-1,2,3,4-tetrahydro-1-naphthalenamine; cis-N-methyl-4-(3-trifluoromethyl-4-chlorophenyl)-1,2,3,4-tetrahydro-1-naphthalenamine; cis-N,N-dimethyl-4-(4-chlorophenyl)-1,2,3,4-tetrahydro-1-naphthalenamine; cis-N,N-dimethyl-4-(3-trifluoromethyl-phenyl)-1,2,3,4-tetrahydro-1-naphthalenamine; and cis-N-methyl-4-(4-chlorophenyl)-7-chloro-1,2,3,4-tetrahydro-1-naphthalenamine. Of interest also is the (1R)-enantiomer of cis-N-methyl-4-(3,4-dichlorophenyl)-1,2,3,4-tetrahydro-1-naphthalenamine.

UK-416244

UK-416244 is an SSRI that is phenoxybenzylamine derivative. UK-416244 has the structure:

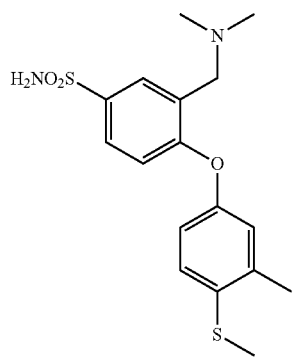 [SMILES: CSc1ccc(Oc2ccc(S(N)(=O)=O)cc2CN(C)C)cc1C]

Structural analogs of UK-416244 are compounds having the formula:

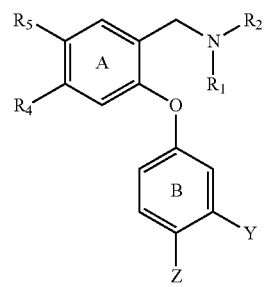

where $R_1$ and $R_2$, independently, are H, $C_{1-6}$ alkyl (e.g., $CH_3$) or substituted heteroalkyl, or $(CH_2)_d(C_{3-6}$ cycloalkyl) where d is 0, 1, 2, or 3; or $R_1$ and $R_2$ together with the nitrogen to which they are attached form an azetidine ring; Z or Y is —S(O)$_n$R$_3$ and the other Z or Y is halogen or —R$_3$; where R$_3$ is independently $C_{1-4}$ alkyl optionally substituted with fluorine (e.g., where R$_3$ is or is not CF$_3$) and n is 0, 1, or 2; or Z and Y are linked so that, together with the interconnecting atoms, Z and Y form a fused 5 to 7-membered carbocyclic or heterocyclic ring which may be saturated, unsaturated, or aromatic, and where when Z and Y form a heterocyclic ring, in addition to carbon atoms, the linkage contains one or two heteroatoms independently selected from O, S, and N; (e.g., with the proviso that when $R_5$ is F and $R_2$ is methyl then the fused ring is not 1,3-dioxolane and Z and Y together do not form a fused phenyl ring); $R_4$ and $R_5$ are, independently, A-X, where A is —CH=CH— or —(CH$_2$)$_p$— where p is 0, 1, or 2; X is H, F, Cl, Br, I, NH$_2$, OH, CONR$_6$R$_7$, SO$_2$NR$_6$R$_7$, SO$_2$NHC(=O)R$_6$, $C_{1-4}$ alkoxy, NR$_8$SO$_2$R$_9$, NO$_2$, NR$_6$R$_{11}$ (e.g., N(CH$_3$)$_2$, CN, CO$_2$R$_{10}$ (e.g., COOH), CHO, SR$_{10}$, S(O)R$_9$ or SO$_2$R$_{10}$; $R_6$, $R_7$, $R_8$ and $R_{10}$ independently are H, $C_{1-6}$ alkyl (e.g., CH$_3$, (CH$_2$)$_3$CH$_3$ or cyclopropyl), $C_{6-12}$ aryl (e.g., phenyl) optionally substituted independently by one or more $R_{12}$, or $C_{1-6}$ alkyl-aryl optionally substituted (e.g., CH$_2$Ph); $R_9$ is $C_{1-6}$ alkyl optionally substituted independently by one or more $R_{12}$, $R_{11}$ is H, $C_{1-6}$ alkyl optionally substituted independently by one or more $R_{12}$, C(O)R$_6$, CO$_2$R$_9$, C(O)NHR$_6$, or SO$_2$NR$_6$R$_7$; $R_{12}$ is F (preferably up to 3), OH, CO$_2$H, $C_{3-6}$ cycloalkyl, NH$_2$, CONH$_2$, $C_{1-6}$ alkoxy, $C_{1-6}$ alkoxycarbonyl, or a 5- or 6-membered heterocyclic ring containing 1, 2, or 3 heteroatoms selected from N, S, and O optionally substituted independently by one or more $R_{13}$; or $R_6$ and $R_7$, together with the nitrogen to which they are attached, form a 4-, 5-, or 6-membered heterocyclic ring optionally substituted independently by one or more $R_{13}$; or a 5- or 6-membered heterocyclic ring containing 1, 2, or 3 heteroatoms selected from N, S, and O optionally substituted independently by one or more $R_{13}$; where $R_{13}$ is hydroxy, $C_{1-4}$ alkoxy, F, $C_{1-6}$ alkyl, haloalkyl, haloalkoxy, —$NH_2$, —$NH(C_{1-6}$ alkyl), or —$N(C_{1-6}$ alkyl)$_2$-;

or compounds having the formula:

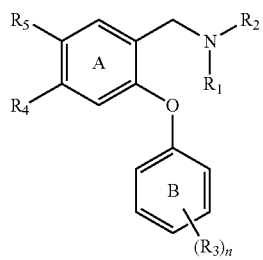

where $R_1$ and $R_2$ are independently H, $C_{1-6}$ alkyl (e.g., $CH_3$) or substituted heteroalkyl, $(CH_2)_m(C_{3-6}$ cycloalkyl) where m is 0, 1, 2, or 3, or $R_1$ and $R_2$ together with the nitrogen to which they are attached form an azetidine ring; each $R_3$ is independently H, I, Br, F, Cl, $C_{1-6}$ alkyl (e.g., $CH_3$), $CF_3$, CN, $OCF_3$, $C_{1-4}$ alkylthio (e.g., $SCH_3$), $C_{1-4}$ alkoxy (e.g., $OCH_3$), aryloxy (e.g., OPh), or $CONR_6R_7$; n is 1, 2, or 3; and $R_4$ and $R_5$ are independently A-X, where A is —CH=CH— or —$(CH_2)_p$— where p is 0, 1, or 2; X is H, F, Cl, Br, I, $CONR_6R_7$, $SO_2NR_6R_7$, $SO_2NHC(=O)\&$, OH, $C_{1-4}$ alkoxy, $NR_8SO_2R_9$, $NO_2$, $NR_6R_{11}$, CN, $CO_2R_{10}$ (e.g., COOH), CHO, $SR_{10}$, $S(O)R_9$, or $SO_2R_{10}$; $R_6$, $R_7$, $R_8$, and $R_{10}$ are independently H or $C_{1-6}$ alkyl (e.g., $(CH_2)_3CH_3$ or cyclopropyl), $C_{6-12}$ aryl (e.g., phenyl) optionally substituted independently by one or more $R_{12}$, or $C_{1-6}$ alkyl-aryl optionally substituted; $R_9$ is $C_{1-6}$ alkyl optionally substituted independently by one or more $R_{12}$; $R_{11}$ is H, $C_{1-6}$ alkyl optionally substituted independently by one or more $R_{12}$, $C(O)R_6$, $CO_2R_9$, $C(O)NHR_6$, or $SO_2NR_6R_7$; $R_{12}$ is F (preferably up to 3), OH, $CO_2H$, $C_{3-6}$ cycloalkyl, $NH_2$, $CONH_2$, $C_{1-6}$ alkoxy, $C_{1-6}$ alkoxycarbonyl or a 5- or 6-membered heterocyclic ring containing 1, 2, or 3 heteroatoms selected from N, S, and O optionally substituted independently by one or more $R_{13}$; or $R_6$ and $R_7$, together with the nitrogen to which they are attached, form a 4-, 5-, or 6-membered heterocyclic ring optionally substituted independently by one or more $R_{13}$; or a 5- or 6-membered heterocyclic ring containing 1, 2, or 3 heteroatoms selected from N, S, and O optionally substituted independently by one or more $R_{13}$; where $R_{13}$ is hydroxy, $C_{1-4}$ alkoxy, F, $C_{1-6}$ alkyl, haloalkyl, haloalkoxy, —$NH_2$, —$NH(C_{1-6}$ alkyl) or —$N(C_{1-6}$ alkyl)$_2$ (e.g., where when $R_1$ and $R_2$ are methyl, $R_4$ and $R_5$ are hydrogen and n is 1, $R_3$ is not a —SMe group para to the ether linkage linking rings A and B). In certain embodiments, n is 1 or 2, and the $R_3$ group(s) is/are at positions 3 and/or 4 of the B ring, for example, are $CH_3$, $SCH_3$, $OCH_3$, Br, or $CF_3$. For either of the above structures, $R_4$ or $R_5$ can be $SO_2NHPh$, $SO_2NHCH_3$, CN, H, Br, $CONH_2$, COOH, $SO_2NHCH_2Ph$, $SO_2NHCOCH_3$, $CH_2NHSO_2CH_3$ $NH_2$, OR $NO_2$, benzyl amide, acylsulfonamide, reverse sulfonamide, $NHCH_3$, $N(CH_3)_2$, $SO_2NH_2$, $CH_2OH$, $NHSO_2CH_3$, $SO_2NHCH_2CCH_2$, $CH_2NH_2$, $SO_2NHBu$, and $SO_2NHcyclopropyl$. UK-416244 structural analogs are described in U.S. Pat. Nos. 6,448,293 and 6,610,747. UK-416244 analogs are described below.

Other analogs of UK-416244 can be described by the formula:

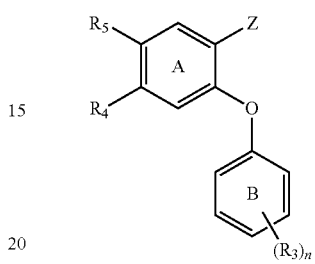

where are $R_3$, $R_4$, and $R_5$ are as defined above and Z is $CH_2NR_1R_2$ where $R_1$ and $R_2$ are as defined above, $C_{1-6}$ alkyl, optionally substituted (e.g., with hydroxyl, $NH_2$, $NHC_{1-6}$ alkyl). In certain embodiments, Z is $CH_2CH(CH_3)_2$, $CH_2OCH_3$, $CH_2N(CH_3)CH_2CH_2OH$, $N(CH_3)_2$, $CH_2N(CH_3)_2$, COOH, $CH_2NHCH_3$, $CH_2OH$, $CH_2NHCOCH_3$, or $CONHCH_3$.

Other UK-416244 analogs are described by the formula.

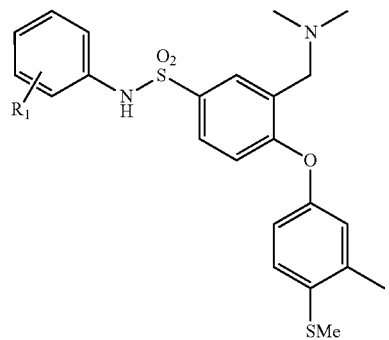

where $R_1$ is H, I, Br, F, Cl, $C_{1-6}$ alkyl (e.g., $CH_3$), $CF_3$, CN, $OCF_3$, $C_{1-4}$ alkylthio (e.g., $SCH_3$), $C_{1-4}$ alkoxy (e.g., $OCH_3$), aryloxy, or $CONR_2R_3$; n is 1, 2, or 3; $R_2$ and $R_3$ are independently H or $C_{1-6}$ alkyl (e.g., $(CH_2)_3CH_3$ or cyclopropyl), $C_{6-12}$ aryl (e.g., phenyl) optionally substituted independently by one or more $R_4$, or $C_{1-6}$ alkyl-aryl optionally substituted; $R_4$ is F (preferably up to 3), OH, $CO_2H$, $C_{3-6}$ cycloalkyl, $NH_2$, $CONH_2$, $C_{1-6}$ alkoxy, $C_{1-6}$ alkoxycarbonyl or a 5- or 6-membered heterocyclic ring containing 1, 2, or 3 heteroatoms selected from N, S, and O optionally substituted independently by one or more $R_5$; or $R_2$ and $R_3$, together with the nitrogen to which they are attached, form a 4-, 5-, or 6-membered heterocyclic ring optionally substituted independently by one or more $R_5$; or a 5- or 6-membered heterocyclic ring containing 1, 2, or 3 heteroatoms selected from N, S, and O optionally substituted independently by one or more $R_5$; where $R_5$ is hydroxy, $C_{1-4}$ alkoxy, F, $C_{1-6}$ alkyl, haloalkyl, haloalkoxy, —$NH_2$, —$NH(C_{1-6}$ alkyl) or —$N(C_{1-6}$ alkyl)$_2$. In certain embodiments, where $R_1$ is Br, OMe, $NO_2$, $CO_2Me$, or CN. $R_1$ may be at the ortho, meta, or para position)

Still other UK-416244 analogs are described by the formula:

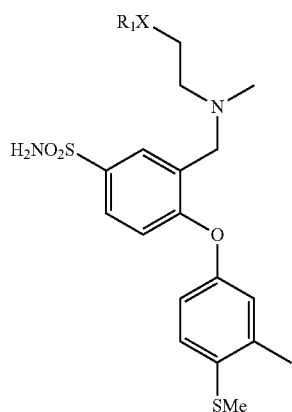

where X is N, O, or S, and $R_1$ is H, $C_{1-6}$ alkyl or substituted heteroalkyl, $(CH_2)_m(C_{3-6}$ cycloalkyl) where m is 0, 1, 2, or 3.

Additional analogs have the structure:

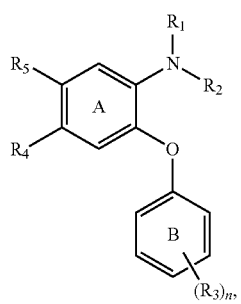

where $R_1$ is H or $C_{1-6}$ alkyl (e.g., $CH_3$, $CH_2CH_3$) and $R_2$ is $C_{1-6}$ alkyl substituted with OH, such as $CH_2OH$, $CH_2CH_2OH$, $CH(OH)CH_3$, $CH_2CH_2CH_2OH$, $CH(CH_2)CH_2OH$, and $CH_2CH_2CH_2CH_2OH$, $CH(OH)CH_2CH_2CH_3$, $CH_2CH(OH)CH_2CH_3$, and $CH_2CH_2CH(OH)CH_3$) or is $CH_2XR_{14}$ or $CH_2CH_2XR_{14}$, where X is N, O, or S, and $R_{14}$ is H, $C_{1-6}$ alkyl or substituted heteroalkyl, $(CH_2)_q(C_{3-6}$ cycloalkyl) where q is 0, 1, 2, or 3, and where $R_3$, $R_4$, and $R_5$ are as defined above.

In certain embodiments, the analog has the structure:

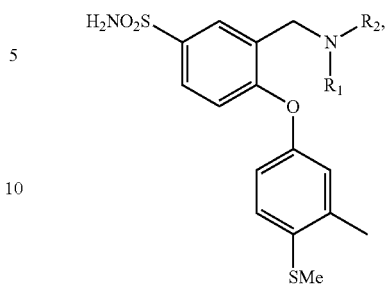

where $R_1$ is H or $C_{1-6}$ alkyl (e.g., $CH_3$, $CH_2CH_3$) and $R_2$ is $C_{1-6}$ alkyl substituted with OH, e.g., $CH_2OH$, $CH_2CH_2OH$, $CH(OH)CH_3$, $CH_2CH_2CH_2OH$, $CH(CH_2)CH_2OH$, and $CH_2CH_2CH_2CH_2OH$, $CH(OH)CH_2CH_2CH_3$, $CH_2CH(OH)CH_2CH_3$, and $CH_2CH_2CH(OH)CH_3$). In particular embodiments, the compound is:

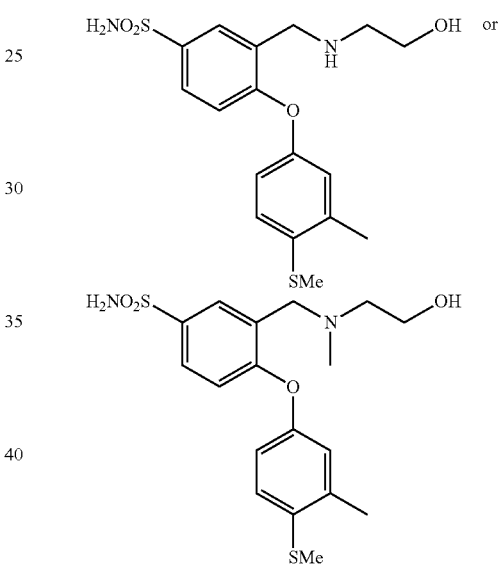

UK-416244 analogs include those of Table 5:

TABLE 5

UK-416244 analogs

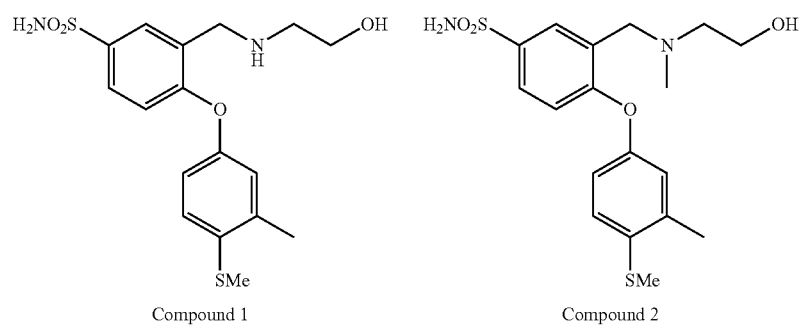

Compound 1    Compound 2

TABLE 5-continued
UK-416244 analogs
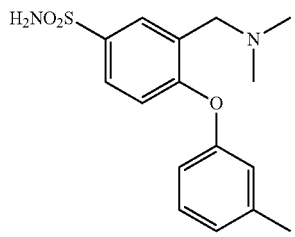
Compound 3
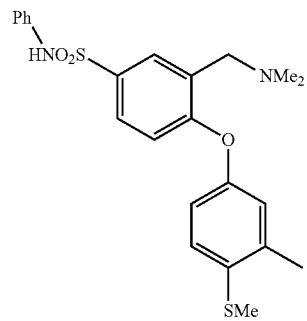
Compound 4
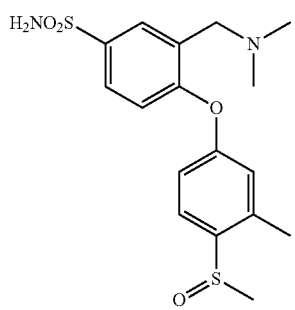
Compound 5
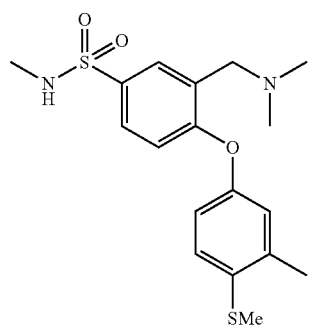
Compound 6
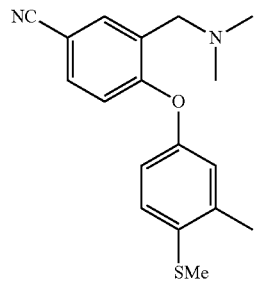
Compound 7
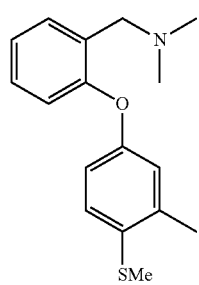
Compound 8
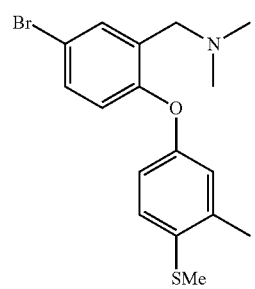
Compound 9

TABLE 5-continued
UK-416244 analogs
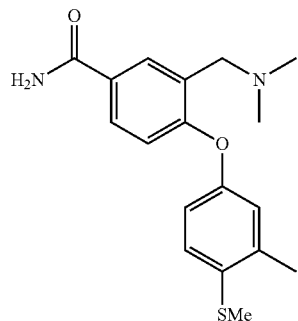
Compound 10
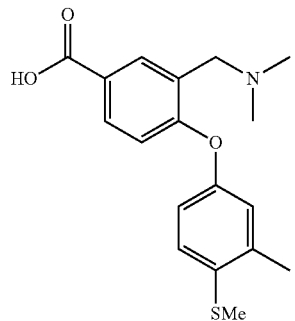
Compound 11
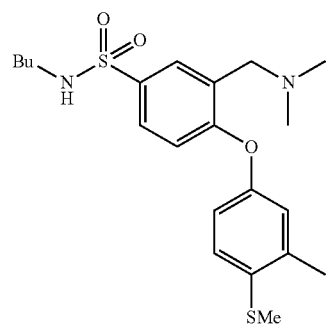
Compound 12
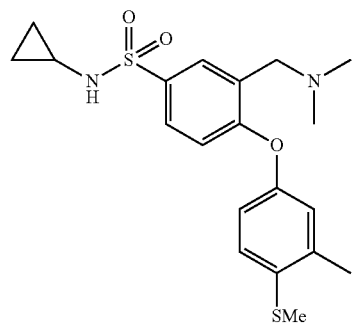
Compound 13
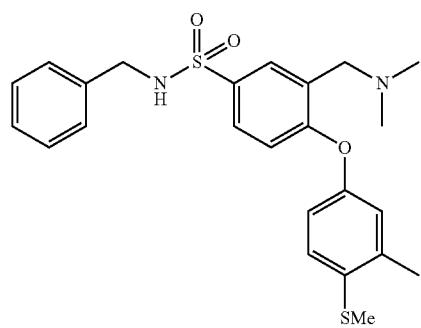
Compound 14
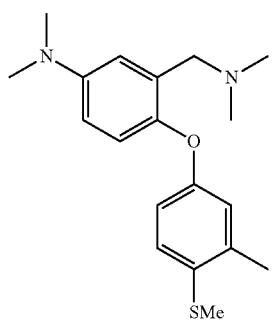
Compound 15
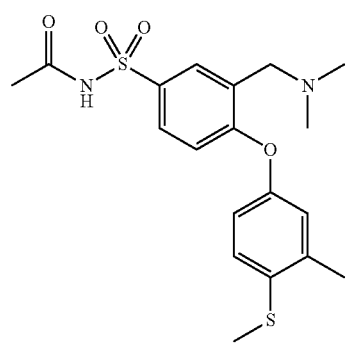
Compound 16
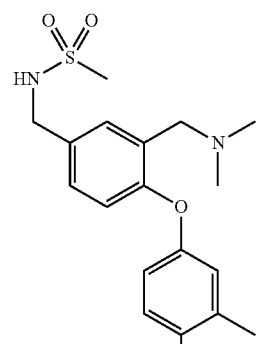
Compound 17

TABLE 5-continued
UK-416244 analogs
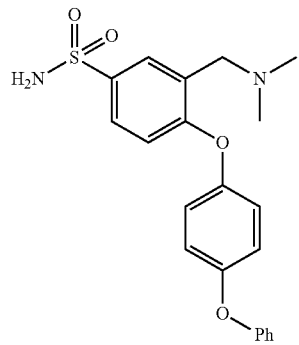
Compound 18
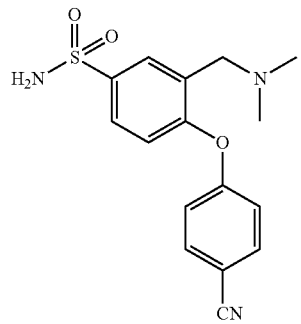
Compound 19
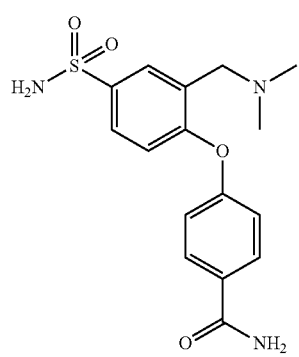
Compound 20
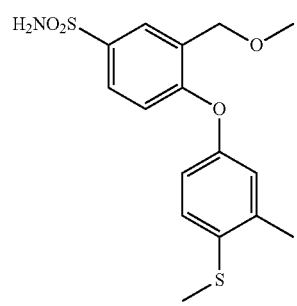
Compound 21
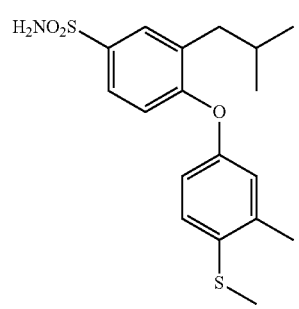
Compound 22
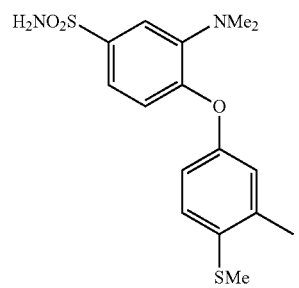
Compound 23
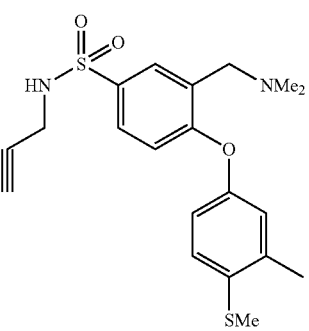
Compound 24

TABLE 5-continued
UK-416244 analogs
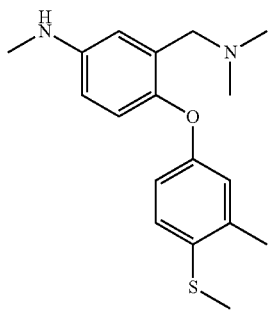
Compound 25
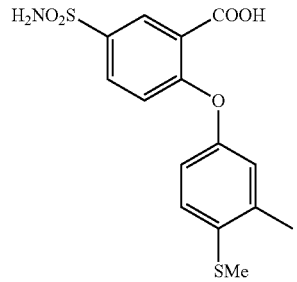
Compound 26
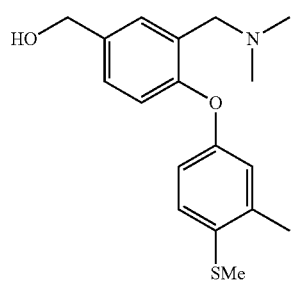
Compound 27
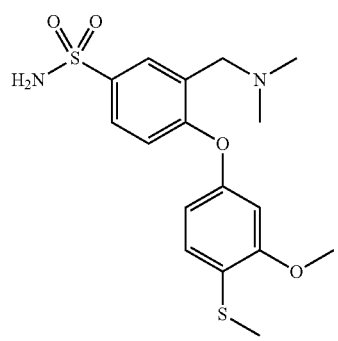
Compound 28
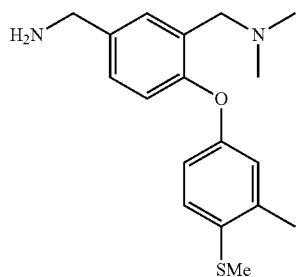
Compound 29
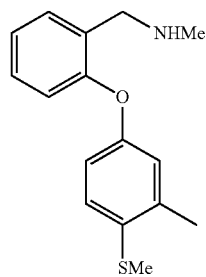
Compound 30
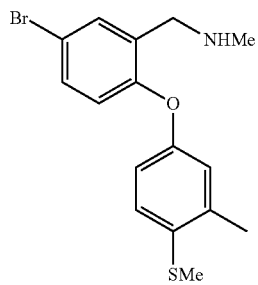
Compound 31
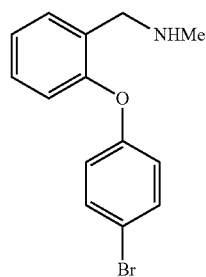
Compound 32

TABLE 5-continued
UK-416244 analogs
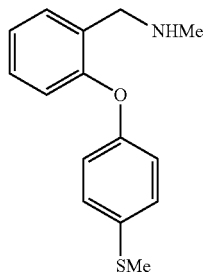
Compound 33
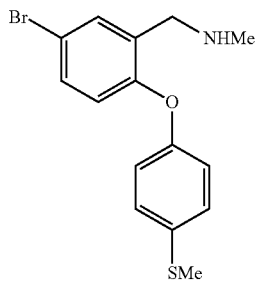
Compound 34
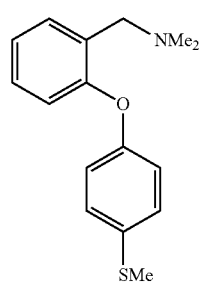
Compound 35
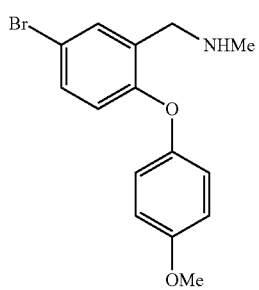
Compound 36
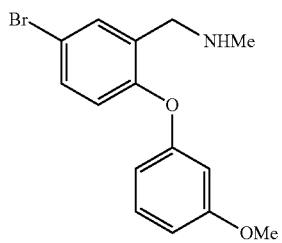
Compound 37
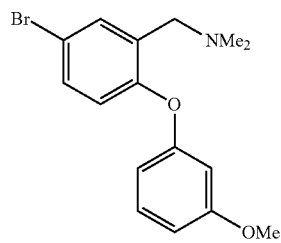
Compound 38
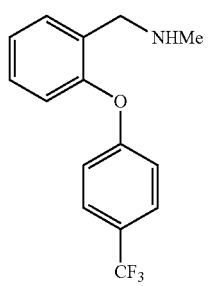
Compound 39
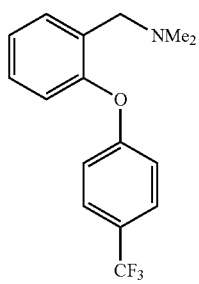
Compound 40
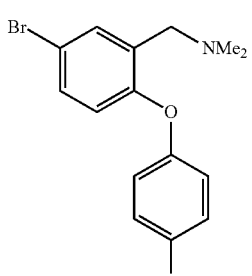
Compound 41
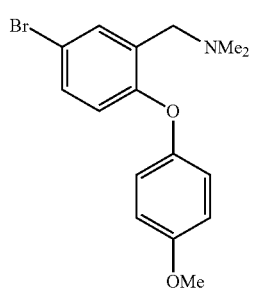
Compound 42

TABLE 5-continued
UK-416244 analogs
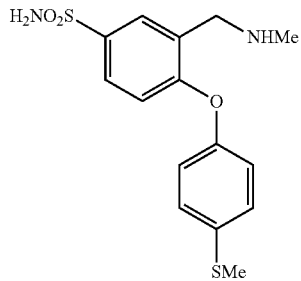
Compound 43
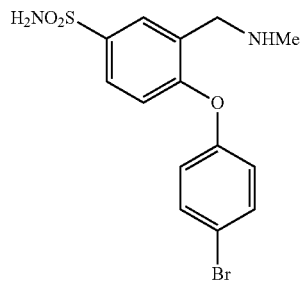
Compound 44
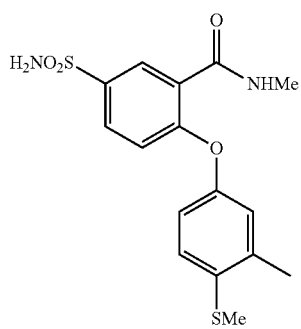
Compound 45
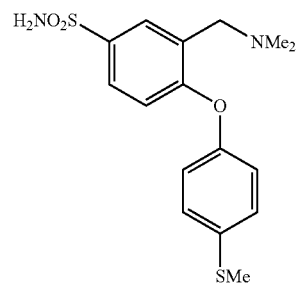
Compound 46
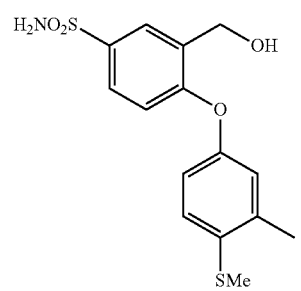
Compound 47
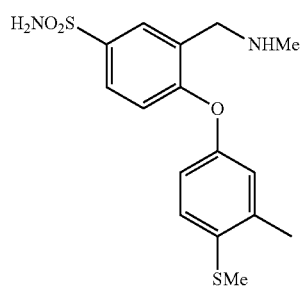
Compound 48
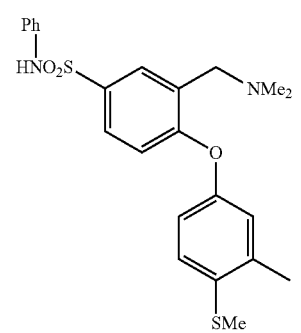
Compound 49
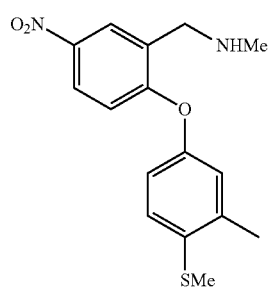
Compound 50

TABLE 5-continued

UK-416244 analogs

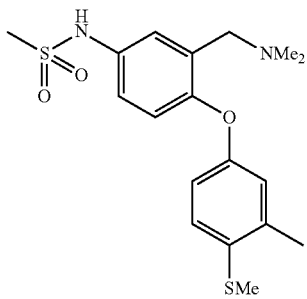

Compound 51

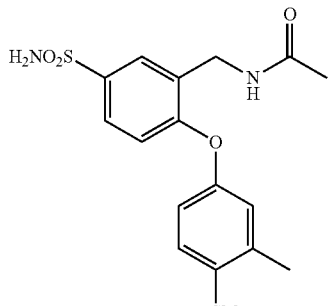

Compound 52

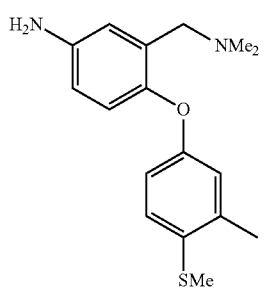

Compound 53

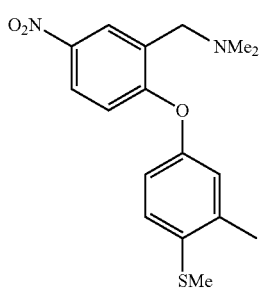

Compound 54

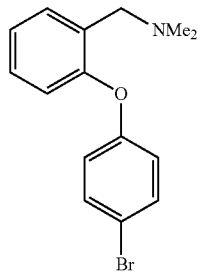

Compound 55

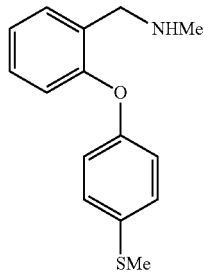

Compound 56

Sertraline, UK-416244, and analogs thereof are considered herein to be equivalents in the methods, compositions, and kits of the invention.

SSRIs are considered herein to be analogs of paroxetine, sertraline, and UK-416244 and, thus, may be used in connection with the invention. SSRIs include cericlamine (e.g., cericlamine hydrochloride); citalopram (e.g., citalopram hydrobromide); clovoxamine; cyanodothiepin; dapoxetine; escitalopram (escitalopram oxalate); femoxetine (e.g., femoxetine hydrochloride); fluoxetine (e.g., fluoxetine hydrochloride); fluvoxamine (e.g., fluvoxamine maleate); ifoxetine; indalpine (e.g., indalpine hydrochloride); indeloxazine (e.g., indeloxazine hydrochloride); litoxetine; milnacipran (e.g., minlacipran hydrochloride); 6-nitroquipazine; tametraline hydrochloride; viqualine; and zimeldine (e.g., zimeldine hydrochloride). SNRIs (selective serotonin norepinephrine reuptake inhibitors), which include venlafaxine, duloxetine, and 4-(2-fluorophenyl)-6-methyl-2-piperazinothieno[2,3-d]pyrimidine, are also considered herein to be analogs of paroxetine, sertraline, and UK-416244 and, thus, may be used in connection with the invention. Pharmacologically active metabolites of any of the foregoing SSRIs and SNRIs can also be used in the methods, compositions, and kits of the invention. Exemplary metabolites are didesmethylcitalopram, desmethylcitalopram, desmethylsertraline, and norfluoxetine.

Other Compounds

Flupentixol

Flupentixol is a thioxanthene anti-psychotic drug. Flupentixol is described in U.S. Pat. No. 3,282,930, and exemplary analogs of flupentixol are described by formula I in U.S. Pat. No. 3,951,961, e.g., 2-trifluoromethyl-6-fluoro-9-(3-(4-(2-hydroxyethyl)piperazin-1-yl)-1-propenyl)thioxanthene, 2-trifluoromethyl-6-fluoro-9-(3-(4-(2-hydroxyethyl)piperazin-1-yl)-1-propenyl)thioxanthene, 2-trifluoromethyl-6-fluoro-9-(3-(4-(2-hydroxyethyl)piperazin-1-yl)-1-propenyl)thioxanthene dihydrochloride, 2-trifluoromethyl-6-fluoro-9-(3-(4-(2-hydroxyethyl)piperidine) 1-propenyl)thioxanthene, 2-trifluoromethyl-6-fluoro-9-(3-(4-(2-hydroxyethyl)piperidine) 1-propenyl)thioxanthene, and 2-trifluoromethyl-6-fluoro-9-(3-(4-(2-hydroxyethyl)piperidine) 1-propenyl)thioxanthene sulphate; by formula I of 4,022,896, e.g., 2-trifluoromethyl-6-fluoro-9-(3-(4-(2-hydroxyethyl)piperazin1-yl)-1-propen yl)thioxanthene, 2-trifluoromethyl-6-fluoro-9-(3-(4-(2-hydroxyethyl)piperidine) 1-propenyl)

thioxanthene, 2-trifluoromethyl-6-fluoro-9-(3-(4-(2-hydroxyethyl)piperazin1-yl)-1-propenyl)thioxanthene, and 2-trifluoromethyl-6-fluoro-9-(3-(4-(2-hydroxyethyl)piperidine) 1-propenyl)thioxanthene, by formula I of U.S. Pat. No. 4,042,695, e.g., 2-trifluoromethyl-6-fluoro-9-(3-(4-(2-hydroxyethyl)-piperazine-1-yl)propyl)-thiaxanthene, 2-trifluoromethyl-6-fluoro-9-(3-(4-(2-hydroxyethyl)-piperazine-1-yl)propyl)-thiaxanthene dihydrochloride, 2-trifluoromethyl-6-fluoro-9-(3-(4-(2-hydroxyethyl)-piperazine-1-yl) propylidene)-thiaxanthene, 2-trifluoromethyl-6-fluoro-9-(3-(4-(2-hydroxyethyl)piperazine-1-yl)propyl-thiaxanthene dihydrochloride, 2-trifluoromethyl-6-fluoro-9-(3-(piperazine-1-yl)propyl)thiaxanthene dioxalate salt, 2-trifluoromethyl-6-fluoro-9-(3-(4-(2-hydroxyethyl)piperazine-1-yl) propyl)-thiaxanthene dihydrochloride, 2-trifluoromethyl-6-fluoro-9-(3-(4-(2-hydroxyethyl)piperazine-1-yl)propyl)-thiaxanthene, 2-trifluoromethyl-6-fluoro-9-(3-(4-methyl-1-piperazinyl)propyl)thiaxanthene, 2-trifluoromethyl-6-fluoro-9-(3-(4-(2-hydroxyethyl)-piperazine-1-yl)propyl)-thiaxanthene palmitic acid ester, and 2-dimethylsulfamoyl-6-fluoro-9-(3-(4-methyl-piperazinyl)propyl-thiaxanthene; and by formula I of U.S. Pat. No. 4,044,024. Yet other examples are trifluoromethyl-6-fluoro-9-(3-dimethylaminopropylidene)-thiaxanthene and 2-trifluoromethyl-6-fluoro-9-(2-propenylidene)-thioxanthene.

Aripiprazole

Aripiprazole is an atypical antipsychotic described in U.S. Pat. No. 5,006,528. Exemplary analogs are given by variations of formula I in U.S. Pat. No. 5,006,528, e.g., 7-{4-[4-(2,3-dichlorophenyl)-1-piperazinyl]-butoxy}carbostyril, 7-{4-[4-(2-ethoxyphenyl)-1-piperazinyl]butoxy}-3,4-dihydrocarbostyril, and 7-{4-[4-]2-ethoxyphenyl)-1-piperazinyl butoxy}-carbostyril. Additional exemplary analogs include compounds described in U.S. Pat. No. 4,234,584 and compounds of formula I in U.S. Pat. No. 7,053,092, e.g., 7-{4-[4-(2,3-dichlorophenyl)-1-piperazinyl]butoxyl}-3,4-dihydrocarbostyril; compounds of formula 1 of U.S. Pat. No. 7,160,888, e.g., 7-[4-(4-naphthalen-1-yl-piperazin-1-yl)-butoxy]-3,4-dihydro-1H-[1,8]napht-hyridin-2-one, 7-[4-(4-napthalen-1-yl-piperazin-1-yl)-butoxy]-3,4-dihydro-1H-[1,8]naphth-hyridin-2-one, and 7-[4-(4-naphthalen-1-yl-piperazin-1-yl)-butoxy]-3,4-dihydro-1H-[1,8]napht-hyridin-2-one.

Pimozide

Pimozide is a benzimidazole compound with anti-psychotic activities. Analogs of pimozide may include, e.g., 3-[1-[4,4-bis(4-fluorophenyl)butyl]piperidin-4-yl]-1H-benzimidazol-2-one, 3-[1-[4,4-bis(4-fluorophenyl)butyl]piperidin-4-yl]-6-fluoro-1H-benzimidazol-2-one, 1-[4,4-bis(4-fluorophenyl)butyl]-3-piperidin-4-ylbenzimidazol-2-one, 3-[2-[4-[bis(4-fluorophenyl)methyl]piperidin-1-yl]ethyl]-1H-benzimidazol-2-one, 4-[4,4-bis(4-fluorophenyl)butyl] spiro[1,4-diazinan-1-ium-1,3'-1H-benzimidazol-3-ium]-2'-one, 3-[1-[4,4-bis(4-fluorophenyl)butyl]piperidin-4-yl]-6-iodo-1H-benzimidazol-2-one, 3-[3-[4-[bis(4-fluorophenyl)methyl]piperazin-1-yl]-2-methylpropyl]-1H-benzimidazol-2-one, 3-[3-[4-[bis(4-fluorophenyl)methyl]piperazin-1-yl]propyl]-1H-benzimidazol-2-one, 3-[1-[4,4-bis(4-fluorophenyl)butyl]-1-oxidopiperidin-1-ium-4-yl]-1H-benzimidazol-2-one, 3-[2-[4-[(4-fluoroanilino)-(4-fluorophenyl)methyl]piperidin-1-yl]ethyl]-1H-benzimidazol-2-one, 3-[2-[4-[bis(4-fluorophenyl)methyl]piperazin-1-yl]ethyl]-1H-benzimidazol-2-one, 3-[3-[4-[(4-fluorophenyl)-phenylmethyl]piperazin-1-yl]propyl]-1H-benzimidazol-2-one, 3-[4-[4-[bis(4-fluorophenyl)methyl]piperazin-1-yl]butyl]-1H-benzimidazol-2-one, 3-[(3R,6S)-6-(4-fluorophenyl)-1-(phenylmethyl)piperidin-3-yl]-1H-benzimidazol-2-one, 3-[(3R,6R)-6-(4-fluorophenyl)-1-(phenylmethyl)piperidin-3-yl]-1H-benzimidazol-2-one, 3-[1-[4,4-bis(4-fluorophenyl)butyl]piperidin-4-yl]-6-methyl-1H-benzimidazol-2-one, 3-[1-[4,4-bis(4-fluorophenyl) cyclohex-2-en-1-yl]piperidin-4-yl]-6-fluoro-1H-benzimidazol-2-one, 3-[1-[4,4-bis(4-fluorophenyl) cyclohex-2-en-1-yl]piperidin-4-yl]-1H-benzimidazol-2-one, 3-[1-[4,4-[bis(4-fluorophenyl)methyl]piperazin-1-yl]pentyl]-1H-benzimidazol-2-one, 3-[6-[4-[bis(4-fluorophenyl) methyl]piperazin-1-yl]hexyl]-1H-benzimidazol-2-one, 3-[4-[4-[(4-fluorophenyl)-phenylmethyl]piperazin-1-yl]butyl]-1H-benzimidazol-2-one, 3-[2-[4-[(4-fluorophenyl)-phenylmethyl]piperazin-1-yl]ethyl]-1H-benzimidazol-2-one, 3-[4,4-bis(4-fluorophenyl)butyl]-1H-benzimidazol-2-one, 3-[1-[4,4-bis(4-fluorophenyl)cyclohexyl]piperidin-4-yl]-1H-benzimidazol-2-one, 3-[1-[4,4-bis(4-fluorophenyl) cyclohex-2-en-1-yl]piperidin-4-yl]-6-fluoro-1H-benzimidazol-2-one hydrochloride, 3-[1-[4,4-bis(4-fluorophenyl)cyclohex-2-en-1-yl]piperidin-4-yl]-1H-benzimidazol-2-one hydrochloride, 3-[1-[3,3-bis(4-fluorophenyl)cyclopentyl]piperidin-4-yl]-1H-benzimidazol-2-one, 3-[1-[4,4-bis(4-fluorophenyl)cyclohexyl]piperidin-4-yl]-6-fluoro-1H-benzimidazol-2-one, 3-[1-[4,4-bis(2,4-difluorophenyl)cyclohex-2-en-1-yl]piperidin-4-yl]-6-fluoro-1H-benzimidazol-2-one, 3-[1-[3-[2-(4-fluorophenyl) anilino]propyl]piperidin-4-yl]-1H-benzimidazol-2-one, 3-[3-[4-[[2-(2-fluorophenyl)phenyl]methyl]piperazin-1-yl] propyl]-1H-benzimidazol-2-one, 1-[1-[4,4-bis(4-fluorophenyl)butyl]piperidin-4-yl]-3-(2,3-ditritiopropyl)benzimidazol-2-one, 3-[3-[4-[(4-fluorophenyl)methyl]piperidin-1-yl] propyl]-1H-benzimidazol-2-one, 3-[2-[4-[di(phenyl)methyl] piperidin-1-yl]ethyl]-1H-benzimidazol-2-one,-[4-[8-fluoro-5-(4-fluorophenyl)-3,4,4a,9b-tetrahydro-1H-pyrido[4,3-b] indol-2-yl]butyl]-1H-benzimidazol-2-one, 3-[1-[4,4-bis(4-fluorophenyl)butyl]-3-methylpiperidin-4-yl]-6-(trifluoromethyl)-1H-benzimidazol-2-one, and 3-[1-[4,4-bis (4-fluorophenyl)butyl]-2-methylpiperidin-4-yl]-6-(trifluoromethyl)-1H-benzimidazol-2-one.

Clomipramine

Clomipramine is a member of the tricyclic compounds described in U.S. Pat. No. 3,467,650. Analogs of clomipramine may be described by one the formulas (I), (II), (III), or (IV):

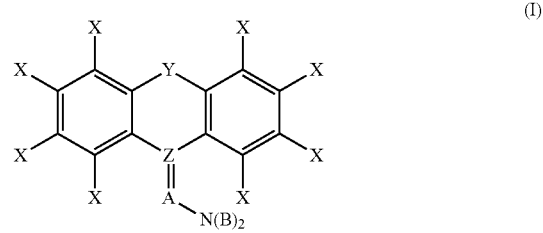

(I)

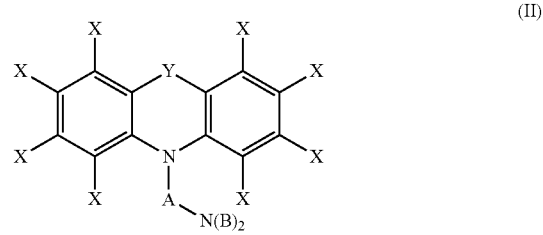

(II)

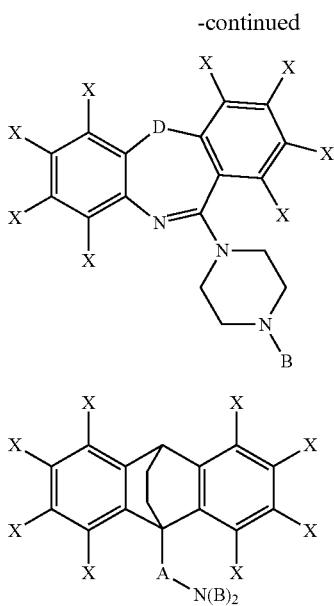

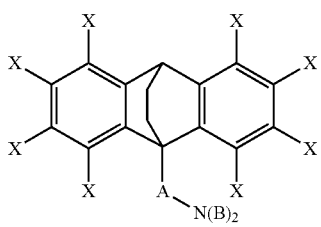

wherein each X is, independently, H, Cl, F, Br, I, CH$_3$, CF$_3$, OH, OCH$_3$, CH$_2$CH$_3$, or OCH$_2$CH$_3$; Y is CH$_2$, O, NH, S(O)$_{0-2}$, (CH$_2$)$_3$, (CH)$_2$, CH$_2$O, CH$_2$NH, CHN, or CH$_2$S; Z is C or S; A is a branched or unbranched, saturated or monounsaturated hydrocarbon chain having between 3 and 6 carbons, inclusive; each B is, independently, H, Cl, F, Br, I, CX$_3$, CH$_2$CH$_3$, OCX$_3$, or OCX$_2$CX$_3$; and D is CH$_2$, O, NH, or S(O)$_{0-2}$. In preferred embodiments, each X is, independently, H, Cl, or F; Y is (CH$_2$)$_2$, Z is C; A is (CH$_2$)$_3$; and each B is, independently, H, Cl, or F. Tricyclic compounds include tricyclic antidepressants such as clomipramine, amoxapine, 8-hydroxyamoxapine, 7-hydroxyamoxapine, loxapine (e.g., loxapine succinate, loxapine hydrochloride), 8-hydroxyloxapine, amitriptyline, doxepin, imipramine, trimipramine, desipramine, nortriptyline, and protriptyline. A tricyclic compound does not need to have antidepressant activities to be within the scope of clomipramine analogs.

Maprotiline

Maprotiline is a bridged-ring tetracyclic compound with psychotropic activities similar to those of the tricyclic antidepressants. The chemical structure of maprotiline and analogs of maprotiline are given by structural formulae in U.S. Pat. No. 3,399,201. Additional exemplary analogs of maprotiline are described by formula I in U.S. Pat. No. 4,017,542, e.g., 9-(2-hydroxy-3-methylamino-propyl)-9,10-dihydro-9,10-ethano-anthracene, 9-(2-hydroxy-3-dimethylamino-propyl)-9,10-dihydro-9,10-ethano-anthracene, 2-chloro-9-(2-hydroxy-3-methylamino-propyl)-9,10-dihydro-9,10-ethano-anthracene, 2-chloro-9-(2-hydroxy-3-dimethylamino-propyl)-9,10-dihydro-9,10-ethano-anthracene; by formula I of U.S. Pat. No. 4,045,560, e.g., 9-(2-morpholinylmethyl)-9,10-dihydro-9,10-methanoanthracene and 9-(4-benzyl-2-morpholinylmethyl)-9,10-dihydro-9,10-methanoanthracene; by formula I of U.S. Pat. No. 4,045,580, e.g., 9-(2-hydroxy-3-methylamino-propyl)-9,10-dihydro-9,10-ethano-anthracene, 9-(2-hydroxy-3-dimethylamino-propyl)-9,10-dihydro-9,10-ethano-anthracene, 2-chloro-9-(2-hydroxy-3-methylamino-propyl)-9,10-dihydro-9,10-ethano-anthracene, and 2-chloro-9-(2-hydroxy-3-dimethylamino-propyl)-9,10-dihydro-9,10-ethano-anthracene; by formula I of U.S. Pat. No. 4,224,344, e.g., γ-methylaminopropyl-9,10-dihydro-9,10-methanoanthracene and γ-dimethylaminopropyl-9,10-dihydro-9,10-methanoanthracene; by formula I of U.S. Pat. No. 4,358,620, e.g., 9-formyl-9,10-dihydro-9,10-methanoanthracene; by formulae I, Ia, and Ib of U.S. Pat. No. 5,266,570, e.g., N-(1-[(9S,10S)-(+)-2-chloro-9,10-dihydro-9,10-methanoanthracen-9-ylmethyl]-4-piperidyl)-2-ethoxyacetamide, (2R)—N-(1-[2-chloro-9,10-dihydro-9,10-methanoanthracen-9-ylmethyl]-4-piperidyl)-2-methoxypropionamide, (2R)-N-(1-[(9S,10S)-2-chloro-9,10-dihydro-9,10-methanoanthracen-9-ylmethyl]-4-piperidyl)-2-methoxypropionamide, N-(1-[2-chloro-9,10-dihydro-9,10-methanoanthracen-9-ylmethyl]-4-piperidyl)-2-(2-pyridyl)acetamide, N-(1-[2-chloro-9,10-dihydro-9,10-methanoanthracen-9-ylmethyl]-4-piperidyl)-2-ethoxypropionamide, N-(1-[2-chloro-9,10-dihydro-9,10-methanoanthracen-9-ylmethyl]-4-piperidyl)-2-(2,2,2-trifluoroethoxy)acetamide, N-(1-[2-chloro-9,10-dihydro-9,10-methanoanthracen-9-ylmethyl]-4-piperidyl)-2,2-dimethylpropionamide, 2-pyridylmethyl-N-(1-[2-chloro-9,10-dihydro-9,10-methanoanthracen-9-ylmethyl]-4-piperidyl)carbamate, N-(1-[(9S,10S)-2-chlor-9,10-dihydro-9,10-methoanthracen-9-yl-methyl]-4-(piperidyl)-2,2-diethoxyacetamide hydrochloride, N-(1-[(9S,10S)-2-chloro-9,10-dihydro-9,10-methanoanthracen-9-ylmethyl]-4-(piperidyl)-2-(2,2,2-trifluoroethoxy)acetamide, N-(1-[(9S,10S)-2-chloro-9,10-dihydro-9,10-methanoanthracen-9-ylmethyl]-4-(piperidyl)-2-methoxy-2-methylpropionamide, and N-(1-[2-chloro-9,10-dihydro-9,10-methanoanthracen-9-yl-methyl]-4-(piperidyl)-2-(4-tetrahydropyranyloxy)acetamide; by formula I of U.S. Pat. No. 5,399,568, e.g., R-1-[1-((9S,10S)-2-chloro-9,10-dihydro-9,10-methanoanthracen-9-ylmethyl)-4-piperidyl]-1-(3-pyridyl)methanol, S-1-[1-((9S,10S)-2-chloro-9,10-dihydro-9,10-methanoanthracen-9-ylmethyl)-4-piperidyl]-1-(3-pyridyl)methanol, (R,S)-1-[1-(9RS,10RS)-(2-chloro-9,10-dihydro-9,10-methanoanthracen-9-ylmethyl)-4-piperidyl]-1-(3-pyridyl)methanol, 1-((9S,10S)-2-chloro-9,10-dihydro-9,10-methanoanthracen-9-ylmethyl)-4-(2-hydroxy-3-pyridylmethyl)piperidine, 1-((9RS,10RS)-2-chloro-9,10-dihydro-9,10-methanoanthracen-9-ylmethyl)-4-(2-hydroxy-3-pyridylmethyl)piperidine; by formula I of U.S. Pat. No. 5,455,246, e.g., 1-(2-chloro-9,10-dihydro-9,10-methanoanthracen-9-ylmethyl)-4-(trans-2,6-dimethyl-4-morpholinyl)piperidine, 1-(2-chloro-9,10-dihydro-9,10-methanoanthracen-9-ylmethyl)-4-(4-morpholinyl)piperidine dihydrochloride, and 2-[1-(9S,10S-2-chloro-9,10-methanoanthracen-9-yl-methyl)-4-piperidylamino]pyrimidine; by formula 1 or 1' of U.S. Pat. No. 5,512,575, e.g., (−)-1-(9,10-dihydro-9,10-methanoanthracen-9-ylmethyl)-4-(2-ethylsulfinyl-3-pyridyl)piperidin-4-ol and (−)-1-(9,10-dihydro-9,10-methanoanthracen-9-yl-methyl)-4-(2-ethylsulfinyl-3-pyridyl)piperidin-4-ol; by formula I of U.S. Pat. No. 5,550,136; and by formulae I or I' of U.S. Pat. No. 5,681,840.

Benzatropine

Benzatropine (also known as benzatropine mesilate and benztropine mesylate) is a muscarinic receptor antagonist. The preparation of benzotropine is described in U.S. Pat. No. 2,595,405. Exemplary analogs of benzatropine are described in U.S. Pat. No. 5,506,359. Other examples are 3'-chloro-3-(diphenylmethoxy)tropane, 3'-chlorobenztropine, 4',4"-dichloro-3-(diphenylmethoxy)tropane, 4'-chloro-3-(diphenylmethoxy)tropane, 4'-chlorobenztropine, metoclophen, N-(n-butyl)-(bis-fluorophenylorophenyl)methoxytropane, N-allyl-(bisfluorophenyl)methoxytropane, N-methyl-3-(bis(4'-fluorophenyl)methoxy)tropane, 3'-chloro-3-(diphenylmethoxy)tropane, 3'-chlorobenztropine, 4',4"-dichloro-3-(diphenylmethoxy)tropane, 4'-chloro-3-(diphenylmethoxy)tropane, and 4'-chlorobenztropine.

Vinorelbine

Vinorelbine is a vinblastine-like anti-mitotic drug and is described in U.S. Pat. No. 4,307,100. Exemplary analogs of vinorelbine are described by formula I of U.S. Pat. No. 4,430,269; by formula I of U.S. Pat. No. 5,100,881, e.g., diethyl N-(4-O-deacetyl-5'-noranhydro-23-vinblastinoyl)-1-amino-2-methylpropylphosphonate, (+)-[diethyl N—($N_a$-deformyl-4-O-deacetyl-23-vincristinoyl)-1-amino-2-methylpropylphosphonate, (+)-[diethyl N-(4-O-deacetyl-23-vincristinoyl)-1-amino-2-methylpropylphosphonate], (−)-[diethyl N-(4-O-deacetyl-23-vincristinoyl)-1-amino-2-methylpropylphosphonate], and (+)-[diethyl N-(4-O-deacetyl-23-vincristinoyl)-1-aminoethylpropylphosphonate]; by formula I in U.S. Pat. No. 5,620,985, e.g., 19',19'-difluoro 15',20'-dihydrovinorelbine, 19',19'-difluoro 15',20'-dihydrovinorelbine, and 20'-deoxy 19',19'-difluorovinblastine; by formula I in U.S. Pat. No. 7,235,564, e.g., 11'-bromovinorelbine, 11'-iodovinorelbine, 11'-vinylvinorelbine, 11'-(3-oxohex-1-enyl)vinorelbine, 1 F-(2-tert-butoxycarbonylvinyl)vinorelbine, and 11'-(methoxycarbonylmethylsulfanyl)vinorelbine trifluoroacetate; and by formula I of U.S. Pat. No. 7,238,704, e.g., 12'-bromovinblastine trifluoroacetate, 12'-iodovinblastine, 12'-bromovincristine, 12'-iodovincristine, and 12'-(hexynyl)vinblastine. Yet other vinorelbine analogs are navelbine derivatives described in U.S. Pat. No. 5,220,016.

Azacitidine

Azacitidine is a pyrimidine analog that interferes with DNA metabolism and has been used as a chemotherapeutic agent.

Exemplary analogs of azacitidine are 2'-beta-deoxy-6-azacytidine, T-deoxy-6-methyl-5-azacytidine, 2'-deoxy-N4-(2-(4-nitrophenyl)ethoxycarbonyl)-5-azacytidine, 5'-azacytidine 5'-triphosphate, 5,6-dihydro-5-azacytidine, 5-aza-2'-deoxycytidine-5'-monophosphate, 5-aza-2'-deoxycytidine-5'-triphosphate, 6-azacytidine, decitabine, fazarabine, N(4),N(4)-dimethyl-5-azacytidine, N(4)-methyl-5-azacytidine, 2'-beta-deoxy-6-azacytidine, 2'-deoxy-6-methyl-5-azacytidine, T-deoxy-N4-(2-(4-nitrophenyl)ethoxycarbonyl)-5-azacytidine, 5'-azacytidine 5'-triphosphate, 5,6-dihydro-5-azacytidine, 5-aza-2'-deoxycytidine-5'-monophosphate, and 5-aza-2'-deoxycytidine-5'-triphosphate. Additional analogs of azacitidine are described in U.S. Pat. No. 4,788,181.

Dasatinib

Dasatinib is a tyrosine kinase inhibitor used for the treatment of certain cancers. Exemplary analogs of dasatinib are described by formula I in U.S. Pat. No. 7,091,223, e.g., N'-(2-chloro-6-methylphenyl)-2-[[2-methyl-6-[[2-(4-morpholinyl)ethyl]amin-o]-4-pyrimidinyl]amino]-5-thiazolecarboxamide, and by formula I of U.S. Pat. No. 7,091,223, e.g., N-(2-chloro-6-methylphenyl)-2-[(4,6-dimethyl-2-pyridinyl)amino]-5-thiazol-ecarboxamide.

Simvastatin

Simvastatin is an HMG-CoA reductase inhibitor and antihypercholesterolemia drug described in European Pat. No. EP0033538 and U.S. Pat. No. 4,444,784. An analog of simvastatin may be a structurally related compound, a compound that inhibits HMG-CoA reductase, or both. Specific examples of simvastatin analogs are lovastatin (GB2046737A), mevastatin (U.S. Pat. No. 3,983,140), pravastatin, monacolin M, monacolin X, fluvastatin (WO/1984/00213)1, atorvastatin, carvastatin (WO/1989/08094), cerivastatin, rosuvastatin, fluindostatin, velostatin, acitemate (101197-99-3), acitretin (CAS 55079-83-9), compactin, dihydrocompactin, rivastatin, dalvastatin (CAS 132100-55-1), itavastatin (U.S. Pat. No. 5,011,930), advicor (WO99/06035), BAY102987, BAY X 2678, BB476, bervastatin (CAS 132017-01-7), BMS-644950 (described in Ahmad et al., J. Med. Chem. 51:2722-2733, 2008), BMS-180431 (described in U.S. Pat. No. 4,824,959), BMY21950, BMY22089, colestolone (described in Green et al., Biochem. J. 135:63-71, 1973), CP-83101 (CAS 120360-17-0), crilvastatin (CAS 120551-59-9), DMP565 (CAS 199480-80-3), glenvastatin (described in EP-00307342), FR901512 (described in Hatori et al., J. Antibiot. 57: 390-393, 2004), L659699 (described in U.S. Pat. No. 4,988,697), L669262 (described in EP-00331250 and EP-00408806), NCX6560 (WO/2004/105754), NR-300s, P882222, P882284, PD134965, PD135022 (CAS 122548-95-2), rawsonol (CAS 125111-69-5), RBx-10558 (WO/2004/05250), RP61969, 52467, 52468, SC37111, SC45355, SQ33600 (Sliskovic et al., Drug News and Perspectives, 5:517-533), SR12813 (U.S. Pat. No. 5,043,330; WO/2002/95652), SR45023A, tocotrienols (described in Parker et al., J. Biol. Chem. 268:11230-11238, 1993) U20685, U88156, and U-9888 (CAS 190783-55-2), as well as pharmaceutically acceptable salts thereof (e.g., simvastatin sodium, lovastatin sodium, fluvastatin sodium, etc.). In addition, HMG CoA-reductase inhibitors are described in Procopiou, et al. (J. Med. Chem. 36: 3658-3665, 1993) and Chan et al. (J. Med. Chem. 36: 3646-3657, 1993).

Yet other simvastatin analogs are described in U.S. Pat. Nos. 3,983,140; 4,231,938; 4,282,155; 4,293,496; 4,294,926; 4,319,039; 4,343,814; 4,346,227; 4,351,844; 4,361,515; 4,376,863; 4,444,784; 4,448,784; 4,448,979; 4,450,171; 4,503,072; 4,517,373; 4,661,483; 4,668,699; 4,681,893; 4,719,229; 4,738,982; 4,739,073; 4,766,145; 4,782,084; 4,804,770; 4,824,959; 4,841,074; 4,847,306; 4,857,546; 4,857,547; 4,940,727; 4,946,864; 5,001,148; 5,006,530; 5,075,311; 5,112,857; 5,116,870; 5,120,848; 5,166,364; 5,173,487; 5,177,080; 5,273,995; 5,276,021; 5,369,123; 5,385,932; 5,502,199; 5,763,414; 5,877,208; and 6,541,511; U.S. Pat. Application Publication Nos. 2002/0013334 A1; 2002/0028826 A1; 2002/0061901 A1; and 2002/0094977 A1; and PCT publications WO/2001/96311 and WO/1996/08248.

Teicoplanin

Teicoplanin is a complex antibiotic agent containing several compounds, five major (named teicoplanin $A_2$-1 through $A_2$-5) and four minor (named teicoplanin $R_S$-1 through $R_S$-4). Thus, as used herein, the term teicoplanin encompasses each of these major and minor compounds. All teicoplanins share a same glycopeptide core, termed teicoplanin A3-1, featuring a fused ring structure to which two carbohydrates (mannose and N-acetylglucosamine) are attached. The major and minor components also contain a third carbohydrate moiety and differ by the length and conformation of a side chain attached to it. Teicoplanin analogs include compounds structurally related to the major and minor teicoplanin constituents and products of teicoplanin hydrolysis, e.g., L 17054 and L 17392. Other analogs of teicoplanin include L 17046, L 17932 (U.S. Pat. No. 5,594,102), 4,7-decadienoyl-teicoplanin, 4-hydroxydecanoyl-teicoplanin, MDL 62873, aglycone forms of any teicoplanin compound or teicoplanin derivative, compounds of formula I of U.S. Pat. No. 4,661,470, demannosyl teichoplanin derivativies, e.g., compounds of formula I of U.S. Pat. No. 5,064,811; compounds described in U.S. Pat. No. 5,085,990; de-(acetylglucosaminyl)-di(dehydro)-deoxy teicoplanin derivatives, e.g., compounds of formula I of U.S. Pat. No. 4,789,661; and substituted alkymides of teicoplanin according to formula I of U.S. Pat. No. 5,198,418.

Terconazole

Terconazole is described in U.S. Pat. No. 4,144,346 and has the following structure:

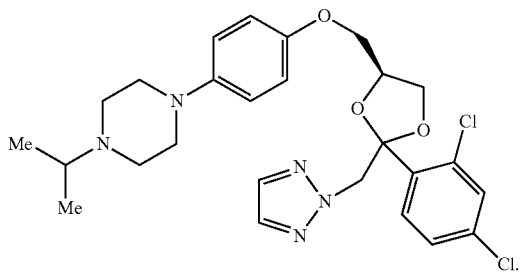 [SMILES: CC(C)N1CCN(c2ccc(OC[C@H]3COC(Cn4nccn4)(c4ccc(Cl)cc4Cl)O3)cc2)CC1]

Structural analogs of terconazole include any stereochemical isomers thereof. Other structural analogs are described in U.S. Pat. Nos. 3,575,999, 3,936,470, 4,223,036, 4,358,449 (see, for example, Examples I-LXXII), in Belgian Pat. No. 935,579, and in the PCT Publication No. WO00/76316.

Structural analogs of terconazole can also be described by the following formula:

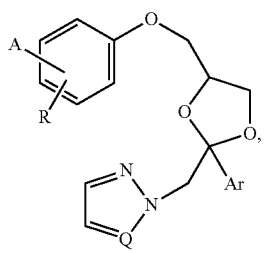

Wherein Q is —CH— or —N—; Ar is optionally substituted phenyl, wherein a substituted phenyl has 1, 2, or 3 substituents that are, independently, halogen, $C_{1-6}$ alkyl, or $C_{1-6}$ alkoxy; A is —NCS, —NR$_2$R$_3$, —NHC(X)—(Y)$_m$—R$_4$, or

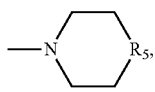

wherein each R$_2$ and R$_3$ is, independently, H or $C_{1-6}$ alkyl; X is O or W; Y is O or NH; m is 0 or 1; R$_4$ is H, optionally substituted $C_{1-6}$ alkyl, or optionally substituted phenyl, wherein a substituted $C_{1-6}$ alkyl, or substituted phenyl has 1 or 2 substituents that are each, independently, halogen, $C_{1-6}$ alkyl, or $C_{1-6}$ alkoxy; R$_5$ is a bond, —CH$_2$—, —O—, —S—, or —NR$_6$—, where R$_6$ is H or optionally substituted $C_{1-6}$ alkyl; and R is H or NO$_2$.

Exemplary, non-limiting structural analogs of terconazle are 4-[2-(3-chlorophenyl)-2-(1H-imidazol-1-ylmethyl)-1,3-dioxolan-4-ylmethoxy]-N-ethylbenzenamine, 4-[2-(4-bromophenyl)-2-(1H-imidazol-1-ylmethyl)-1,3-dioxolan-4-yl-methoxy]-N-ethylbenzenamine, N-ethyl-4-[2-(1H-imidazol-1-ylmethyl)-2-(3-methylphenyl)-1,3-dioxolan-4-ylmethoxy]benzenamine, N-ethyl-4-[2-(1H-imidazol-1-ylmethyl)-2-(4-methoxyphenyl)-1,3-dioxolan-4-yl methoxy]benzenamine, 4-[2-(2,4-dichlorophenyl)-2-(1H-1,2,4-triazol-1-ylmethyl)-1,3-dioxolan-4-yl methoxy]-N-ethylbenzenamine, N-{4-[2-(3-chlorophenyl)-2-(1H-imidazol-1-ylmethyl)-1,3-dioxolan-4-ylmethoxy]phenyl}acetamide. N-{4-[2-(4-bromophenyl)-2-(1H-imidazol-1-ylmethyl)-1,3-dioxolan-4-ylmethoxy]-phenyl}benzamide ethyl{4-[2-(1H-imidazol-1-ylmethyl)-2-(3-methylphenyl)-1,3-dioxolan-4-ylmethoxy]phenyl}carbamate, N-{4-[2-(1H-imidazol-1-ylmethyl)-2-(4-methoxyphenyl)-1,3-dioxolan-4-ylmethoxy]phenyl}-4-fluorobenzamide, N-{4-[2-(2,4-dichlorophenyl)-2-(1H-1,2,4-triazol-1-ylmethyl)-1,3 dioxolan-4-ylmethoxy]phenyl}acetamide, 1-{2-(3-chlorophenyl)-4-[4-(1-pyrrolidinyl)phenoxymethyl]-1,3-dioxolan-2-yl methyl}-1H-imidazole, 1-{2-(4-bromophenyl)-4-[4-(1-piperidinyl) phenoxymethyl]-1,3-dioxolan-2-ylmethyl}-1H-imidazole, 1-{2-(3-methylphenyl)-4-[4-(1-pyrrolidinyl)phenoxymethyl]-1,3-dioxolan-2-yl methyl}-1H-imidazole, 1-{2-(4-methoxyphenyl)-4-[4-(1-piperidinyl)phenoxymethyl]-1,3-dioxolan-2-yl methyl}-1H-imidazole, 1-{2-(2,4-dichlorophenyl)-4-[4-(1-pyrrolidinyl)phenoxymethyl]-1,3-dioxolan-2-ylmethyl}-1H-1,2,4-triazole, 1-{2-(2,4-dichlorophenyl)-4-[4-(1-piperidinyl)phenoxymethyl]-1,3-dioxolan-2-ylmethyl}-1H-1,2,4-triazole, 4-{4-[2-(3-chlorophenyl)-2-(1H-imidazol-1-ylmethyl)-1,3-dioxolan-4-ylmethoxy]phenyl}morpholine, 4-{4-[2-(1H-imidazol-1-ylmethyl)-2-(3-methylphenyl)-1,3-dioxolan-4-ylmethoxy]phenyl}morpholine, 4-{4-[2-(1H-imidazol-1-ylmethyl)-2-(4-methoxyphenyl)-1,3-dioxolan-4-ylmethoxy] phenyl}morpholine, and 4-{4-[2-(2,4-dichlorophenyl)-2-(1H-1,2,4-triazol-1-ylmethyl)-1,3-dioxolan-4-ylmethoxy]phenyl}morpholine.

Hycanthone

Hycanthone is a thioxanthenone schistosomicide described in U.S. Pat. Nos. 3,294,803 and 3,312,598. Analogs of hycanthone include other compounds of formula I in U.S. Pat. No. 3,312,598, lucanthone, methixene, prothixene, quantacure QTX, teflutixol, thiothixene, WIN 33377, chlorprothixene, clopenthixol, doxantrazole, flupenthixol, hycanthone methanesulfonate, hycanthone N-methylcarbamate, hycanthone sulfamate, IA 4, IA 4 N-oxide, 2-(beta-diethylaminoethylamino)-3,4-cyclohexenothia-xanthone, 2-chlorothioxanthen-9-one, 3-carboxy-thioxanthone-10,10-dioxide, 4-(beta-diethylaminoethylamino)-1,2-cyclohexenothiaxanthone, 7-oxo-7-thiomethoxyxanthone-2-carboxylic acid, BW 616U76, and 4-(bis(2'-chloroethyl) amino)propylamino-1,2-cyclohexenothioxanthone.

Atovaquone

Atovaquone is an anti-microbial napthalene compound described in U.S. Pat. No. 5,053,432. Analogs of atovaquone include compounds described by formula I of U.S. Pat. No. 5,053,432, e.g., 2-hydroxy-3-(4-methoxycyclohexyl)-1,4-naphthoquinone, 2-hydroxy-3-[4-(1-methoxy-1-methylethyl)cyclohexyl]-1,4-naphthoquinone, 2-(4-benzyloxycyclohexyl)-3-hydroxy-1,4-naphthoquinone, 2,4-(3,4-dichlorophenyl)cyclohexyl-3-hydroxy-1,4-naphthoquinone, 2-[4-(3,4-dimethylphenyecyclohexyl]-1,4-naphthoquinone, 2-(4-fluorocyclohexyl)-3-hydroxy-1,4-naphthoquinone, 2-hydroxy-3-(4-trifluoromethylcyclohexyl)-1,4-naphthoquinone, 2-(4-n-butoxycyclohexyl)-3-hydroxy-1,4-naphthoquinone, 2-(4-t-butoxycyclohexyl)-3-hydroxy-1,4-naphthoquinone, 2-(4,4-dimethylcyclohexyl)-3-hydroxy-1,4-naphthoquinone, 2-(4,4-diethylcyclohexyl)-3-hydroxy-1,4-naphthoquinone, 2-(4,4-diphenylcyclohexyl)-3-hydroxy-1, 4-naphthoquinone, 2-(4,4-di-n-propylcyclohexyl)-3-hydroxy-1,4-naphthoquinone, and 2-[4-(4-chlorophenoxymethyl)cyclohexyl]-3-hydroxy-1,4-naphthoquinone.

Other exemplary analogs include compounds described by formula II in U.S. Pat. No. 5,310,762, e.g., 2-(4-t-butylcyclohexyl)-3-hydroxy-1,4-naphthoquinone; by formula II in U.S.

Pat. No. 5,466,711, e.g., 2-acetoxy-3-[trans-4-(4-chlorophenyl)cyclohexyl]-1,4-naphthoquinone; by formula II in U.S. Pat. No. 5,567,738, e.g., 2-(4-(4-chlorophenyl)cyclohexyl)-3-hydroxy-1,4-Naphthoquinone; and by formula I, II, or III in U.S. Pat. No. 5,684,035, e.g., 5,8-dihydroxy-1,4-naphthoquinone.

Quinacrine

Quinacrine is an acridine derivative described in U.S. Pat. No. 2,113,357. Analogs of quinacrine include, for example, chloroquine, hydroxychloroquine, amodiaquine, mefloquine, primaquine, quinine, chemiochin (4-N-(6-chloro-2-methoxyacridin-9-yl)-1-N,1-N-diethylpentane-1,4-diamine dihydrochloride), atabrine hydrochloride (4-[(6-chloro-2-methoxyacridin-9-yl)azaniumyl]pentyl-diethylazanium dichloride), NSC240788 (2-N-(6-chloro-2-methoxyacridin-9-yl)-1-N,1-N-diethylpropane-1,2-diamine), NSC 8591 (4-[(6-chloro-2-methoxyacridin-9-yl)azaniumyl]butyl-diethylazanium dichloride), NSC56618 (N-(6-chloro-2-methoxyacridin-9-yl)-N,N-diethylheptane-1,7-diamine), NSC56619 (N'-(6-chloro-2-methoxyacridin-9-yl)-N,N-diethyloctane-1,8-diamine), AIDS 185224 (N-(3-aminopropyl)-N'-(6-chloro-2-methoxyacridin-9-yl)-N-methylpropane-1,3-diamine), NSC353 (N'-(6-chloro-2-methoxyacridin-9-yl)-N,N-diethylpropane-1,3-diamine hydrochloride), NSC 8591 (N'-(6-chloro-2-methoxyacridin-9-yl)-N,N-diethylbutane-1,4-diamine hydrochloride), (WIN 501 (N-(6-chloro-2-methoxyacridin-9-yl)-N',N'-dimethylbutane-1,4-diamine), NSC353 (N'-(6-chloro-2-methoxyacridin-9-yl)-N,N-diethylpropane-1,3-diamine), AIDS185219 (N-(6-chloro-2-methoxyacridin-9-yl)-N,N-dimethylpropane-1,3-diamine), LS-14291 (9[(E)-4-[(6-chloro-2-methoxyacridin-9-yl)azaniumyl]pent-2-enyl]-diethylazanium dichloride), (LS-14292 ([(Z)-4-[(6-chloro-2-methoxyacridin-9-yl)azaniumyl]pent-2-enyl]-diethylazanium dichloride), (S)-quinacrine, N'-(6-chloro-2-methoxyacridin-9-yl)-N,N-di(propan-2-yl)propane-1,3-diamine, (E)-4-N-(6-chloro-2-methoxyacridin-9-yl)-1-N,1-N-diethylpent-2-ene-1,4-diamine, 4-N-(6-chloro-2-methoxyacridin-9-yl)-1-N,1-N-diethylpentane-1,4-diamine hydrochloride, 5-N-(6-chloro-2-methoxyacridin-9-yl)-1-N,1-N-diethylhexane-1,5-diamine, 4-N-(6-chloro-2-methoxyacridin-9-yl)-1-N,1-N-diethylpentane-1,4-diamine chloride, 8-N-(6-chloro-2-methoxyacridin-9-yl)-1-N,1-N-diethylnonane-1,8-diamine, N'-(6-chloro-2-methoxyacridin-9-yl)-N,N-dipropylpropane-1,3-diamine, N'-(6-chloro-2-methoxyacridin-9-yl)-N,N-diethylpentane-1,5-diamine, and 4-N-(6-chloro-2-methoxyacridin-9-yl)pentane-1,4-diamine. Additional quinacrine analogs are described in Macfarlane and Manzel (*J. Immunol.* 160:1122-1131, 1998), Breslow et al. (*J. Am. chem. Soc.* 67:1472-1475, 1945), and Bloom et al. (*J. Am. chem. Soc.* 67:2206-2208, 1945).

Efavirenz

Efavirenz is a non-nucleoside reverse transcriptase inhibitor described in U.S. Pat. No. 5,519,021. Analogs of efavirenz include compounds described by formula I or II of U.S. Pat. No. 5,519,021, e.g., (−)$_6$-chloro-4-cyclopropyl-ethynyl-4-frifluoromethyl-1-4-dihydro-2H-3,1-benzoxazin-2-one, (−) 6-chloro-4-phenylethynyl-4-trifluoromethyl-1,4-dihydro-2H-3,1-benzoxazin-2-one, (+/−) 4-(1-chloro-1,1-difluoromethyl)-4-(2-phenylethynyl)-6-chloro-1,4-dihydro-2H-3,1-benzoxazin-2-one, or (+/−) 4-(2-[dimethylaminomethyl]ethynyl)-4-trifluoromethyl-6-chloro-1,4-dihydro-2H-3,1-benzoxazin-2-one, or a pharmaceutically acceptable salt thereof; by formula I of U.S. Pat. No. 5,874,430, e.g., (+/−)-6-chloro-4-(cyclopropyl ethynyl)-8-hydroxy-4-(trifluoromethyl)-1,4-dihydro-2H-3,1-benzoxazin-2-one, (−)-6-chloro-4-(cyclopropylethynyl)-8-hydroxy-4-(trifluoromethyl)-1,4-dihydro-2H-3,1-benzoxazin-2-one, (+/−)-6-chloro-4-(cyclopropylethynyl)-8-fluoro-4-(trifluoromethyl)-1,4-dihydro-2H-3,1-benzoxazin-2-one, (+/−)-4-cyclopropylethynyl-4-isopropyl-6-methyl-1,4-dihydro-2H-3,1-benzoxazin-2-one, (+/−)-4-isopropylethynyl-4-trifluoromethyl-6-methyl-1,4-dihydro-2H-3,1-benzoxazin-2-one, (+/−)-6-acetyl-4-cyclopropylethynyl-4-trifluoromethyl-1,4-dihydro-2H-3,1-benzoxazin-2-one, (+/−)-5,6-difluoro-4-(3-methyl)-1-buten-1-yl-4-trifluoromethyl-1,4-dihydro-2H-3,1-benzoxazin-2-one, (+/−)-4-isopropylethynyl-4-trifluoromethyl-5,6-difluoro-1,4-dihydro-2H-3,1-benzoxazin-2-one, (+/−)-4-cyclopropylethynyl-6-chloro-4-trifluoromethyl-7-aza-1,4-dihydro-2H-3,1-benzoxazin-2-one, (+/−)-6-chloro-4-(2-methoxyethoxy)-4-(trifluoromethyl)-1,4-dihydro-2H-3,1-benzoxazin-2-one, (+/−)-6-chloro-4-propylamino-4-(trifluoromethyl)-1,4-dihydro-2H-3,1-benzoxazin-2-one, (+/−)-4-(1-butynyl)-6-methoxy-4-trifluoromethyl-1,4-dihydro-2H-3,1-benzoxazin-2-one, (+/−)-4-(1'-hydroxy)-cyclopropylethynyl-4-trifluoromethyl-6-chloro-1,4-dihydro-2H-3,1-benzoxazin-2-one, (+/−)-4-isopropylethynyl-4-trifluoromethyl-5-fluoro-1,4-dihydro-2H-3,1-benzoxazin-2-one, (+/−)-6-chloro-4-(1-deuterocycloprop-1-ylethynyl)-4-(trifluoromethyl)-1,4-dihydro-2H-3,1-benzoxazin-2-one, (+/−)-4-isopropylethynyl-4-trifluoromethyl-5-fluoro-1,4-dihydro-2H-3,1-benzoxazin-2-one, (+/−)-6-chloro-4-(cyclopropylethynyl)-8-methoxy-4-(trifluoromethyl)-1,4-dihydro-2H-3,1-benzoxazin-2-one, (+/−)-6-chloro-4-(cyclopropylethynyl)-7-hydroxy-4-(trifluoromethyl)-1,4-dihydro-2H-3,1-benzoxazin-2-one, (+/−)-6-chloro-4-(1-butynyl)-8-fluoro-4-(trifluoromethyl)-1,4-dihydro-2H-3,1-benzoxazin-2-one, (+/−)-6-chloro-4-(isopentyl)-8-fluoro-4-(trifluoromethyl)-1,4-dihydro-2H-3,1-benzoxazin-2-one, (+/−)-5,6-difluoro-4-(cyclopropylethynyl)-4-(trifluoromethyl)-1,4-dihydro-2H-3,1-benzoxazin-2-one, (+/−)-5,6-difluoro-4-(isopropylethynyl)-4-(trifluoromethyl)-1,4-dihydro-2H-3,1-benzoxazin-2-one, (+/−)-5,6-difluoro-4-(1-pentynyl)-4-(trifluoromethyl)-1,4-dihydro-2H-3,1-benzoxazin-2-one, (+/−)-5,6-difluoro-4-(1-butynyl)-4-(trifluoromethyl)-1,4-dihydro-2H-3,1-benzoxazin-2-one, (+/−)-5,6-difluoro-4-(1-propynyl)-4-(trifluoromethyl)-1,4-dihydro-2H-3,1-benzoxazin-2-one, (+/−)-5,6-difluoro-4-pentyl-4-(trifluoromethyl)-1,4-dihydro-2H-3,1-benzoxazin-2-one, (+/−)-5,6-difluoro-4-isopentyl-4-(trifluoromethyl)-1,4-dihydro-2H-3,1-benzoxazin-2-one, (+/−)-5,6-difluoro-4-butyl-4-(trifluoromethyl)-1,4-dihydro-2H-3,1-benzoxazin-2-one, (+/−)-5,6-methylenedioxy-4-(cyclopropylethynyl)-4-(trifluoromethyl)-1,4-dihydro-2H-3,1-benzoxazin-2-one, (+/−)-5,6-methylenedioxy-4-(isopropylethynyl)-4-(trifluoromethyl)-1,4-dihydro-2H-3,1-benzoxazin-2-one, (+/−)-5,6-methylenedioxy-4-(1-pentynyl)-4-(trifluoromethyl)-1,4-dihydro-2H-3,1-benzoxazin-2-one, (+/−)-5,6-methylenedioxy-4-(1-butynyl)-4-(trifluoromethyl)-1,4-dihydro-2H-3,1-benzoxazin-2-one, (+/−)-5,6-methylenedioxy-4-(2-pentynyl)-4-(trifluoromethyl)-1,4-dihydro-2H-3,1-benzoxazin-2-one, (+/−)-5,6-methylenedioxy-4-(2-butynyl)-4-(trifluoromethyl)-1,4-dihydro-2H-3,1-benzoxazin-2-one, (+/−)-5,6-methylenedioxy-4-(isopentyl)-4-(trifluoromethyl)-1,4-dihydro-2H-3,1-benzoxazin-2-one, (+/−)-6-methoxy-4-(cyclopropylethynyl)-4-(trifluoromethyl)-1,4-dihydro-2H-3,1-benzoxazin-2-one, (+/−)-6-methoxy-4-(isopropylethynyl)-4-(trifluoromethyl)-1,4-dihydro-2H-3,1-benzoxazin-2-one, (+/−)-6-methoxy-4-(1-pentynyl)-4-(trifluoromethyl)-1,4-dihydro-2H-3,1-benzoxazin-2-one, (+/−)-6-methoxy-4-(1-propynyl)-4-(trifluoromethyl)-1,4-dihydro-2H-3,1-benzoxazin-2-one, (+/−)-6-methoxy-4-(2- pentynyl)-4-(trifluoromethyl)-1,4-dihydro-2H-3,1-benzoxazin-2-one, (+/−)-6-methoxy-4-(isopentyl)-4-(trifluoromethyl)-1,4-dihydro-2H-3,1-benzoxazin-2-one, (+/−)-6-methoxy-4-butyl-4-(trifluoromethyl)-1,4-dihydro-2H-3,1-benzoxazin-2-one, (+/−)-6-methoxy-4-(phenylethyl)-4-(trifluoromethyl)-1,4-dihydro-2H-3,1-benzoxazin-2-one, (+/−)-6-methoxy-4-(cyclopropylethynyl)-8-fluoro-4-(trifluoromethyl)-1,4-di hydro-2H-3,1-benzoxazin-2-one, (+/−)-6-dimethylamino-4-(cyclopropylethynyl)-4-(trifluoromethyl)-1,4-dihydro-2H-3,1-benzoxazin-2-one, (+/−)-6-dimethylamino-4-(isopropylethynyl)-4-(trifluoromethyl)-1,4-dihydro-2H-3,1-benzoxazin-2-one, (+/−)-6-dimethylamino-4-pentyl-4-(trifluoromethyl)-1,4-dihydro-2H-3,1-benzoxazin-2-one, (+/−)-6-dimethylamino-4-isopentyl-4-(trifluoromethyl)-1,4-dihydro-2H-3,1-benzoxazin-2-one, (+/−)-6-acetyl-4-(1-butynyl)-4-(trifluoromethyl)-1,4-dihydro-2H-3,1-benzoxazin-2-one, (+/−)-6-methyl-4-(cyclopropylethynyl)-4-(trifluoromethyl)-1,4-dihydro-2H-3,1-benzoxazin-2-one, (+/−)-6-methyl-4-(1-butynyl)-4-(trifluoromethyl)-1,4-dihydro-2H-3,1-benzoxazin-2-one, (+/−)-6,8-dichloro-4-(cyclopropylethynyl)-4-(trifluoromethyl)-1,4-dihydro-2H-3,1-benzoxazin-2-one, (+/−)-6,8-dichloro-4-(phenylethyl)-4-(trifluoromethyl)-1,4-dihydro-2H-3,1-benzoxazin-2-one, (+/−)-5,6,8-trifluoro-4-(cyclopropyl ethynyl)-4-(trifluoromethyl)-1,4-dihydro-2H-3,1-benzoxazin-2-one, (+/−)-5,6,8-trifluoro-4-(isopropylethynyl)-4-(trifluoromethyl)-1,4-dihydro-2H-3,1-benzoxazin-2-one, (+/−)-5,6,8-trifluoro-4-(1-pentynyl)-4-(trifluoromethyl)-1,4-dihydro-2H-3,1-benzoxazin-2-one, (+/−)-5,6,8-trifluoro-4-(1-butynyl)-4-(trifluoromethyl)-1,4-dihydro-2H-3,1-benzoxazin-2-one, (+/−)-5,8-difluoro-4-(cyclopropylethynyl)-4-(trifluoromethyl)-1,4-dihydro-2H-3,1-benzoxazin-2-one, (+/−)-5,8-difluoro-4-(isopropylethynyl)-4-(trifluoromethyl)-1,4-dihydro-2H-3,1-benzoxazin-2-one, (+/−)-5,8-difluoro-4-(1-pentynyl)-4-(trifluoromethyl)-1,4-dihydro-2H-3,1-benzoxazin-2-one, (+/−)-5,8-difluoro-4-(1-butynyl)-4-(trifluoromethyl)-1,4-dihydro-2H-3,1-benzoxazin-2-one, (+/−)-6-isopropyl-4-(cyclopropylethynyl)-4-(trifluoromethyl)-1,4-dihydro-2h,3,1-benzoxazin-2-one, (+/−)-6-isopropyl-4-(isopropylethynyl)-4-(trifluoromethyl)-1,4-dihydro-2H-3,1-benzoxazin-2-one, (+/−)-6-isopropyl-4-(phenylethynyl)-4-(trifluoromethyl)-1,4-dihydro-2H-3,1-benzoxazin-2-one, (+/−)-6-isopropyl-4-pentyl-4-(trifluoromethyl)-1,4-dihydro-2H-3,1-benzoxazin-2-one, (+/−)-6-isopropyl-4-(isopentyl)-4-(trifluoromethyl)-1,4-dihydro-2H-3,1-benzoxazin-2-one, (+/−)-6-isopropyl-4-(phenylethyl)-4-(trifluoromethyl)-1,4-dihydro-2H-3,1-benzoxazin-2-one, (+/−)-6-trifluoromethoxy-4-(cyclopropylethynyl)-4-(trifluoromethyl)-1,4-dihydro-2H-3,1-benzoxazin-2-one, (+/−)-6-trifluoromethoxy-4-(isopropylethynyl)-4-(trifluoromethyl)-1,4-dihydro-2H-3,1-benzoxazin-2-one, (+/−)-6-trifluoromethoxy-4-(phenylethynyl)-4-(trifluoromethyl)-1,4-dihydro-2H-3,1-benzoxazin-2-one, (+/−)-6-trifluoromethoxy-4-pentyl-4-(trifluoromethyl)-1,4-dihydro-2H-3,1-benzoxazin-2-one, (+/−)-6-trifluoromethoxy-4-(isopentyl)-4-(trifluoromethyl)-1,4-dihydro-2H-3,1-benzoxazin-2-one, (+/−)-6-trifluoromethoxy-4-(phenylethyl)-4-(trifluoromethyl)-1,4-dihydro-2h-3,1-benzoxazin-2-one, (+/−)-4-(phenylethyl)-4-(trifluoromethyl)-1,4-dihydro-2H-3,1-benzoxazin-2-one, (+/−)-4-(isopropylethynyl)-4-(trifluoromethyl)-1,4-dihydro-2H-3,1-benzoxazin-2-one, (+/−)-4-(phenylethynyl)-4-(trifluoromethyl)-1,4-dihydro-2H-3,1-benzoxazin-2-one, (+/−)-4-(pentyl)-4-(trifluoromethyl)-1,4-dihydro-2H-3,1-benzoxazin-2-one, (+/−)-4-(isopentyl)-4-(trifluoromethyl)-1,4-dihydro-2H-3,1-benzoxazin-2-one, (+/−)-6-phenyl-4-(cyclopropylethynyl)-4-(trifluoromethyl)-1,4-dihydro-2H-3,1-benzoxazin-2-one, (+/−)-6-phenyl-4-(isopropylethynyl)-4-(trifluoromethyl)-1,4-dihydro-2H-3,1-benzoxazin-2-one, (+/−)-6-phenyl-4-(1-pentynyl)-4-(trifluoromethyl)-1,4-dihydro-2H-3,1-benzoxazin-2-one, (+/−)-6-phenyl-4-(4-methylpentynyl)-4-(trifluoromethyl)-1,4-dihydro-2H-3,1-benzoxazin-2-one, (+/−)-6-phenyl-4-(1-butynyl)-4-(trifluoromethyl)-1,4-dihydro-2H-3,1-benzoxazin-2-one, (+/−)-6-phenyl-4-(isopentyl)-4-(trifluoromethyl)-1,4-dihydro-2H-3,1-benzoxazin-2-one, (+/−)-6-methoxy-4-(cyclopropylethynyl)-4-isopropyl-1,4-dihydro-2H-3,1-benzoxazin-2-one, (+/−)-6-methoxy-4-(isopropylethynyl)-4-isopropyl-1,4-dihydro-2H-3,1-benzoxazin-2-one, (+/−)-6-methyl-4-(isopropylethynyl)-4-cyclopropyl-1,4-dihydro-2H-3,1-benzoxazin-2-one, (+/−)-6-methyl-4-(isopropylethynyl)-4-isopropyl-1,4-dihydro-2H-3,1-benzoxazin-2-one, (+/−)-6-methyl-4-(isopropylethynyl)-4-ethyl-1,4-dihydro-2H-3,1-benzoxazin-2-one, (+/−)-6-methyl-4-(1-butynyl)-4-ethyl-1,4-dihydro-2H-3,1-benzoxazin-2-one, (+/−)-6,7-dichloro-4-(isopropylethynyl)-4-cyclopropyl-1,4-dihydro-21'-3,1-benzoxazin-2-one, (+/−)-6,7-dichloro-4-(isopropylethynyl)-4-isopropyl-1,4-dihydro-2H-3,1-benzoxazin-2-one, (+/−)-7-chloro-4-(cyclopropylethynyl)-4-cyclopropyl-1,4-dihydro-2H-3,1-benzoxazin-2-one, (+/−)-7-chloro-4-(isopropylethynyl)-4-cyclopropyl-1,4-dihydro-2H-3,1-benzoxazin-2-one, (+/−)-7-chloro-4-(4-methylpentynyl)-4-cyclopropyl-1,4-dihydro-2H-3,1-benzoxazin-2-one, (+/−)-7-chloro-4-(cyclopropylethynyl)-4-isopropyl-1,4-dihydro-2H-3,1-benzoxazin-2-one, (+/−)-7-chloro-4-(isopropylethynyl)-4-isopropyl-1,4-dihydro-2H-3,1-benzoxazin-2-one, (+/−)-6-chloro-4-(cyclopropylethynyl)-4-(trifluoromethyl)-8-aza-1,4-dihydro-2H-3,1-benzoxazin-2-one, (+/−)-6-chloro-4-(isopropylethynyl)-4-(trifluoromethyl)-8-aza-1,4-dihydro-2H-3,1-benzoxazin-2-one, (+/−)-6-chloro-4-(-phenylethyl)-4-(trifluoromethyl)-8-aza-1,4-dihydro-2H-3,1-benzoxazin-2-one, (+/−)-6-methoxy-4-(cyclopropylethynyl)-4-(trifluoromethyl)-7-aza-1,4-dihydro-2H-3,1-benzoxazin-2-one, and (+/−)-4-(cyclopropylethynyl)-4-(trifluoromethyl)-6-aza-1,4-dihydro-2H-3,1-benzoxazin-2-one; by formula II, Ia, or Ib of U.S. Pat. No. 6,090,821; by formula I of U.S. Pat. No. 6,124,302, e.g., (+/−)-6-chloro-4-cyclopropylethynyl-4-trifluoromethyl-3,4-dihydro-2(1H)-quinazolinone, (+/−)-6-chloro-4-(2-pyridyl)ethynyl-4-trifluoromethyl-3,4-dihydro-2(1H)-quinazolinone, (+/−)-6-chloro-4-phenylethynyl-4-trifluoromethyl-3,4-dihydro-2(1H)-quinazolinone, (+/−)-4-cyclopropylethynyl-6-methoxy-4-trifluoromethyl-3,4-dihydro-2(1H)-quinazolinone, (+/−)-6-methoxy-4-(2-pyridyl)ethynyl-4-trifluoromethyl-3,4-dihydro-2(1H)-quinazolinone, (+/−)-6-methoxy-4-phenylethynyl-4-trifluoromethyl-3,4-dihydro-2(1H)-quinazolinone, (+/−)-4-cyclopropylethynyl-5,6-difluoro-4-trifluoromethyl-3,4-dihydro-2(1H-quinazolinone, (+/−)-5,6-difluoro-4-(2-pyridyl)ethynyl-4-trifluoromethyl-3,4-dihydro-2(1H)-quinazolinone, (+/−)-5,6-difluoro-4-phenylethynyl-4-trifluoromethyl-3,4-dihydro-2(1H)-quinazolinone, (+/−)-4-cyclopropylethynyl-6-fluoro-4-trifluoromethyl-3,4-dihydro-2(1H)-quinazolinone, (+/−)-6-fluoro-4-(2-pyridyl)ethynyl-4-trifluoromethyl-3,4-dihydro-2(1H)-quinazolinone, (+/−)-6-fluoro-4-phenylethynyl-4-trifluoromethyl-3,4-dihydro-2(1H)-quinazolinone, (+/−)-6-fluoro-4-(2'-2-pyridyl)ethyl-4-trifluoromethyl-3,4-dihydro-2(1H)-quinazolinone, (+/−)-6-fluoro-4-phenylethyl-4-trifluoromethyl-3,4-dihydro-2(1H)-quinazolinone, (−)-6-chloro-4-cyclopropylethynyl-4-trifluoromethyl-3,4-dihydro-2(1H)-quinazolinone, (+)-6-chloro-4-cyclopropylethynyl-4-trifluoromethyl-3,4-dihydro-2(1H)-quinazolinone, (+)-4-cyclopropylethynyl-5, 6-difluoro-4-trifluoromethyl-3,4-dihydro-2(1H)-quinazolinone, (−)-4-cyclopropylethynyl-5,6-difluoro-4-trifluoromethyl-3,4-dihydro-2(1H)-quinazolinone, (+)-E-4-cyclopropylethynyl-5,6-difluoro-4-trifluoromethyl-3,4-dihydro-2(1H)-quinazolinone, and (−)-6-chloro-4-E-cyclopropylethynyl-4-trifluoromethyl-3,4-dihydro-2(1H)-quinazolinone; by formula I of U.S. Pat. No. 6,127,375, e.g., (+/−)-4-cyclopropylethynyl-5,6-difluoro-4-trifluoromethyl-3,4-dihydro-2(1H)-quinazolinthione, (+/−)-6-chloro-4-cyclopropylethynyl-4-trifluoromethyl-3,4-dihydro-2(1H)-quinazolinthione, (+/−)-4-cyclopropylethynyl-5,6-difluoro-4-trifluoromethyl-3,4-dihydro-2-methyl(1H)-quinazolinthione, and (+/−)-6-chloro-4-cyclopropylethynyl-4-trifluoromethyl-3,4-dihydro-2-methyl(1H)-quinazolinthione; by formula I of U.S. Pat. No. 6,140,320, e.g., 5-(1-butynyl)-7-chloro-1,5-dihydro-5-(trifluoromethyl)-4,1-benzoxazepin-2(3H)-one, rel-(3S,5S)-5-(1-butynyl)-7-chloro-1,5-dihydro-3-phenyl-5-(trifluoromethyl)-4,1-benzoxazepin-2(3H)-one, 7-chloro-1,5-dihydro-5-(isopropylethynyl)-5-(trifluoromethyl)-4,1-benzoxazepin-2(3H)-one, (+)-(5S)-7-chloro-1,5-dihydro-5-(isopropylethynyl)-5-(trifluoromethyl)-4,1-benzoxazepin-2(3H)-one, trans-7-chloro-5-(2-cyclopropylethenyl)-1,5-dihydro-5-(trifluoromethyl)-4,1-benzoxazepin-2(3H)-one, rel-(3S,5S)-trans-7-chloro-5-(2cyclopropylethenyl)-1,5-dihydro-3-methyl-5-trifluozomethyl)-4,1-benzoxazepin-2(3H)-one, 1,5-dihydro-7-fluoro-5-isopropylethynyl-5-(trifluoromethyl)-4,1-benzoxazepin-2(3H)-one, 1,5-dihydro-7-fluoro-5-(3-methylbutyl)-5-(trifluoromethyl)-4,1-benzoxazepin-2(3H)-one, rel-(3S,5S)-trans-7-chloro-1,5-dihydro-5-(2-furan-2-ylethenyl)-3-methyl-5-(trifluoromethyl)-4,1-benzoxazepin-2(3H)-one, trans-7-chloro-1,5-dihydro-5-(2-furan-2-yl)ethenyl-5-(trifluoromethyl)-4,1-benzoxazepin-2(3H)-one, rel-(3S,5S)-7-chloro-1,5-dihydro-5-(2-furanyl)ethynyl-3-methyl-5-(trifluoromethyl)-4,1-benzoxazepin-2(3H)-one, 5-butyl-7-chloro-1,5-dihydro-5-(trifluoromethyl)-4,1-benzoxazepin-2(3H)-one 4-isopropylethynyl-4-trifluoromethyl-5,6-difluoro-1,4-dihydro-2H-3,1-benzoxazepin-2-one, rel-(3S,5S)-7-chloro-5-cyclopropylethynyl-1,5-dihydro-3-propyl-5-(trifluoromethyl)-4,1-benzoxazepin-2(3H)-one, rel-(3R,5S)-7-chloro-5-cyclopropylethynyl-1,5-dihydro-3-propyl-5-(trifluoro methyl)-4,1-benzoxazepin-2(3H)-one, rel-(3S,5S)-7-chloro-5-cyclopropletethynyl-1,5-dihydro-3-isopropyl-5-(trifluoromethyl-)-4,1-benzoxazepin-2(3H)-one, 7-chloro-5-phenylethynyl-1,5-dihydro-5-(trifluoromethyl)-4,1-benzoxazepin-2 (3H)-one, rel-(3S,5S)-7-chloro-5-isopropylethynyl-1,5-dihydro-3-methyl-5-(trifluoromethyl)-4,1-benzoxazepin-2(3H)-one, 7-chloro-5-cyclopropylethynyl-1,5-dihydro-5-(trifluoromethyl)-4,1-benzoxazepin-2(3H)-one, 7-chloro-5-isopropylethynyl-1,5-dihydro-5-(trifluoromethyl)-4,1-benzoxazepin-2(3H)-one, trans-7-chloro-5-(2-isopropylethenyl)-1,5-dihydro-5-(trifluoromethyl)-4,1-benzoxazepin-2(3H)-one, 7-methoxy-5-(3-methylbutyl)-1,5-dihydro-5-(trifluoromethyl)-4,1-benzoxazepin-2(3H)-one, rel-(3S,5S)-7-chloro-5-cyclopropylethynyl-1,5-dihydro-3-ethyl-5-(trifluoromethyl)-4,1-benzoxazepin-2(3H)-one, rel-(3R,5S)-7-chloro-5-cyclopropylethynyl-1,5-dihydro-3-ethyl-5-(trifluoromethyl)-4,1-benzoxazepin-2(3H)-one, 7-chloro-5-(3-pyridyl)ethynyl-1,5-dihydro-5-(trifluoromethyl)-4,1-benzoxazepin-2(3H)-one, trans-7-chloro-5-(3-pyrid-3-ylethenyl)-1,5-dihydro-5-(trifluoromethyl)-4,1-benzoxazepin-2(3H)-one, trans-7-fluoro-5-(2-isopropylethenyl)-1,5-dihydro-5-(trifluoromethyl)-4,1-benzoxazepin-2(3H)-one, trans-6,7-difluoro-5-(2-isopropylethenyl)-1,5-dihydro-5-(trifluoromethyl)-4,1-benzoxazepin-2(3H)-one, rel-(3S,5S)-7-chloro-5-cyclopropylethynyl-1,5-dihydro-3-methyl-5-(trifluoro methyl)-4,1-benzoxazepin-2(3H)-one, rel-(3S,5S)-trans-7-chloro-5-(2-cyclopropylethenyl)-1,5-dihydro-3-methyl-5-(trifluoromethyl)-4,1-benzoxazepin-2(3H)-one, rel-(3S,5S)-trans-7-chloro-5-(2-cyclopropylethenyl)-1,5-dihydro-3-propyl-5-(trifluoromethyl)-4,1-benzoxazepin-2(3H)-one, rel-(3S,5S)-7-chloro-5-(3-furanylethynyl)-1,5-dihydro-3-methyl-5-(trifluoromethyl)-4,1-benzoxazepin-2(3H)-one, rel-(3S,5S)-7-chloro-5-(3-furanylethynyl)-1,5-dihydro-3-ethyl-5-(trifluoromethyl)-4,1-benzoxazepin-2(3H)-one, rel-(3S,5S)-6,7-difluoro-5-cyclopropylethynyl-1,5-dihydro-3-methyl-5-(trifluoromethyl)-4,1-benzoxazepin-2(3H)-one, rel-(3S,5S)-6,7-difluoro-5-cyclopropylethynyl-1,5-dihydro-3-ethyl-5-(trifluoromethyl)-4,1-benzoxazepin-2(3H)-one, rel-(3S,5S)-trans-6,7-difluoro-5-(2-cyclopropylethenyl)-1,5-dihydro-3-methyl-5-(trifluoromethyl)-4,1-benzoxazepin-2(3H)-one, (+)-(3S,5S)-7-chloro-5-cyclopropylethynyl-1,5-dihydro-3-methyl-5-(trifluoromethyl)-4,1-benzoxazepin-2(3H)-one, (3S)-7-chloro-5-cyclopropylethynyl-1,5-dihydro-5-(trifluoromethyl)-4,1-benzocazepin-2(3H)-one, rel-(3S,5S)-trans-7-chloro-5-(2-cyclopropylethenyl)-1,5-dihydro-3-ethyl-5-(trifluoromethyl)-4,1-benzoxazepin-2(3H)-one, (+)-(3S,5S)-trans-7-chloro-5-(2-cyclopropylethenyl)-1,5-dihydro-3-methyl-5-(trifluoromethyl)-4,1-benzoxazepin-2(3H)-one, (+)-(3S,5S)-trans-7-chloro-5-(2-cyclopropylethenyl)-1,5-dihydro-3-ethyl-5-(trifluoromethyl)-4,1-benzoxazepin-2(3H)-one, rel-(3S,5S)-7-chloro-5-(2-cyclopropylethynyl)-1,5-dihydro-3-ethenyl-5-(trifluoromethyl)-4,1-benzoxazepin-2(3H)-one, rel-(3S,5S)-trans-7-chloro-5-(2-cyclopropylethenyl)-1,5-dihydro-3-ethenyl-5-(trifluoromethyl)-4,1-benzoxazepin-2(3H)-one, rel-(3S,5S)-7-chloro-5-(2-cyclopropylethynyl)-1,5-dihydro-3-cyclopropyl-5-(trifluoromethyl)-4,1-benzoxazepin-2(3H)-one, rel-(3S,5S)-trans-7-chloro-5-(2-cyclopropylethenyl)-1,5-dihydro-3-cyclopropyl-5-(trifluoromethyl)-4,1-benzoxazepin-2(3H)-one, rel-(3S,5S)-6,7-difluoro-5-(2-cyclopropylethynyl)-1,5-dihydro-3-ethenyl-5-(trifluoromethyl)-4,1-benzoxazepin-2(3H)-one, rel-(3S,5S)-6,7-difluoro-5-(2-cyclopropylethynyl)-1,5-dihydro-3-cyclopropyl-5-(trifluoromethyl)-4,1-benzoxazepin-2(3H)-one, rel-(3S,5S)-7-fluoro-5-(2-cyclopropylethynyl)-1,5-dihydro-3-ethenyl-5-(trifluoromethyl)-4,1-benzoxazepin-2(3H)-one, rel-(3S,5 S)-7-fluoro-5-(2-cyclopropylethynyl)-1,5-dihydro-3-methyl-5-(trifluoromethyl)-4,1-benzoxazepin-2 (3H)-one, rel-(3S,5S)-7-fluoro-5-(2-cyclopropylethynyl)-1,5-dihydro-3-ethyl-5-(trifluoromethyl)-4,1-benzoxazepin-2(3H)-one, rel-(3S,5S)-trans-7-fluoro-5-(2-cyclopropylethenyl)-1,5-dihydro-3-methyl-5-(trifluoromethyl)-4,1-benzoxazepin-2(3H)-one, rel-(3S,5S)-trans-7-fluoro-5-(2-cyclopropylethenyl)-1,5-dihydro-3-ethyl-5-(trifluoromethyl)-4,1-benzoxazepin-2(3H)-one, rel-(3S,5S)-6,7-methylenedioxy-5-(2-cyclopropylethynyl)-1,5-dihydro-3-methyl-5-(trifluoromethyl)-4,1-benzoxazepin-2(3H)-one, rel-(3S,5S)-6,7-methylenedioxy-5-2-cyclopropylethynyl)-1,5-dihydro-3-ethyl-5-(trifluoromethyl)-4,1-benzoxazepin-2(3H)-one, rel-(3S,5S)-trans-6,7-methylenedioxy-5-(2-cyclopropylethenyl)-1,5-dihydro-3-methyl-5-(trifluoromethyl)-4,1-benzoxazepin-2(3H)-one, and rel-(3S,5S)-trans-6,7-methylenedioxy-5-(2-cyclopropylethenyl)-1,5-dihydro-3-ethyl-5-(trifluoromethyl)-4,1-benzoxazepin-2(3H)-one, by formula I or II of U.S. Pat. No. 6,303,780, e.g., (+/−)-6-chloro4-(cyclopropylethynyl)-8-hydroxy-4-(trifluoromethyl)-1,4-dihydro-2H-3,1-benzoxazin-2-one; (−)-6-chloro-4-(cyclopropylethynyl)-8-hydroxy-4-(trifluoromethyl)-1,4-dihydro-2H-3,1-benzoxazin-2-one, (+/−)-6-chloro-4-(cyclopropylethynyl)-

8-fluoro-4-(trifluoromethyl)-1,4-dihydro-2H-3,1-benzoxazin-2-one, (+/−)-4-cyclopropylethynyl-4-isopropyl-6-methyl-1,4-dihydro-2H-3,1-benzoxazin-2-one, (+/−)-4-isopropylethynyl-4-trifluoromethyl-6-methyl-1,4-dihydro-2H-3,1-benzoxazin-2-one, (+/−)-6-acetyl-4-cyclopropylethynyl-4-trifluoromethyl-1,4-dihydro-2H-3,1-benzoxazin-2-one, (+/−)-5,6-difluoro-4-(3-methyl)-1-buten-1-yl-4-trifluoromethyl-1,4-dihydro-2H-3,1-benzoxazin-2-one, (+/−)-4-isopropylethynyl-4-trifluoromethyl-5,6-difluoro-1,4-dihydro-2H-3,1-benzoxazin-2-one, (+/−)-4-cyclopropyl ethynyl-6-chloro-4-trifluoromethyl-7-aza-1,4-dihydro-2H-3,1-benzoxazin-2-one, (+/−)-6-chloro-4-(2-methoxyethoxy)-4-(trifluoromethyl)-1,4-dihydro-2H-3,1-benzoxazin-2-one, (+/−)-6-chloro-4-propylamino-4-(trifluoromethyl)-1,4-dihydro-2H-3,1-benzoxazin-2-one, (+/−)-6-chloro-4-(2-(furan-2-yl)ethynyl)-4-(trifluoromethyl)-1,4-dihydro-2H-3,1-benzoxazin-2-one, (+/−)-4-(1-butynyl)-6-methoxy-4-trifluoromethyl-1,4-dihydro-2H-3,1-benzoxazin-2-one, (+/−)-4-(1'-hydroxy)-cyclopropylethynyl-4-trifluoromethyl-6-chloro-1,4-dihydro-2H-3,1-benzoxazin-2-one, (+/−)-4-isopropylethynyl-4-trifluoromethyl-5-fluoro-1,4-dihydro-2H-3,1-benzoxazin-2-one, (+/−)-6-chloro-4-(1-deuterocycloprop-1-ylethynyl)-4-(trifluoromethyl)-1,4-dihydro-2H-3,1-benzoxazin-2-one, and (+/+4-isopropylethynyl-4-trifluoromethyl-5-fluoro-1,4-dihydro-2H-3,1-benzoxazin-2-one; by formula I of U.S. Pat. No. 6,492,515, e.g., (+/−)-6-chloro-4-(cyclopropylethynyl)-8-hydroxy-4-(trifluoromethyl)-1,4-dihydro-2H-3,1-benzoxazin-2-one, (−)-6-chloro-4-(cyclopropylethynyl)-8-hydroxy-4-(trifluoromethyl)-1,4-dihydro-2H-3,1-benzoxazin-2-one, and (+/−)-6-chloro-4-(cyclopropylethynyl)-8-fluoro-4-(trifluoromethyl)-1,4-dihydro-2H-3,1-benzoxazin-2-one; by formula I of U.S. Pat. No. 6,593,337, e.g., 7-chloro-5-(cyclopropylmethoxy)-5,10-dihydro-5-(trifluoromethyl)benzo[b][1,8]naphthyridine, 7-chloro-5-(benzyloxy)-5,10-dihydro-5-(trifluoromethyl)benzo[b][1,8]naphthyridine, 7-chloro-5-(cyclobutylmethoxy)-5,10-dihydro-5-(trifluoromethyl)benzo[b][1,8]naphthyridine, 7-chloro-5-(ethoxy)-5,10-dihydro-5-(trifluoromethyl)benzo[b][1,8]naphthyridine, 7-chloro-5-(hydroxy)-5,10-dihydro-5-(trifluoromethyl)benzo[b][1,8]naphthyridine, 7-chloro-5-(n-propoxy)-5,10-dihydro-5-(trifluoromethyl)benzo[b][1,8]naphthyridine, 7-chloro-5-(i-propoxy)-5,10-dihydro-5-(trifluoromethyl)benzo[b][1,8]naphthyridine, 7-chloro-5-(butyl)-5,10-dihydro-5-(trifluoromethyl)benzo[b][1,8]naphthyridine, 7-chloro-5-(methoxy)-5,10-dihydro-5-(trifluoromethyl)benzo[b][1,8]naphthyridine, 7-chloro-5(S)-(cyclopropylmethoxy)-5,10-dihydro-5-(trifluoromethyl)benzo[b][1,8]naphthyridine, 7-chloro-5(R)-(cyclopropylmethoxy)-5,10-dihydro-5-(trifluoromethyl)benzo[b][1,8]naphthyridine, 7-chloro-5-(2-cyclopropylethyl)-5,10-dihydro-5-(trifluoromethyl)benzo[b][1,8]naphthyridine, 7-chloro-5-(2,2,2-trifluoroethoxy)-5,10-dihydro-5-(trifluoromethyl)benzo[b][1,8]naphthyridine, 7-chloro-5-(propargoxy)-5,10-dihydro-5-(trifluoromethyl)benzo[b][1,8]naphthyridine, 7-chloro-5-(ethyl)-5,10-dihydro-5-(trifluoromethyl)benzo[b][1,8]naphthyridine, 7-chloro-5-(cyclopropylmethoxy)-2-methyl-5,10-dihydro-5-(trifluoromethyl)benzo[b][1,8]naphthyridine, 7-chloro-5-(n-butyl)-2-methyl-5,10-dihydro-5-(trifluoromethyl)benzo[b][1,8]naphthyridine, 7-chloro-5-(2-cyclopropylethyl)-2-methyl-5,10-dihydro-5-(trifluoromethyl)benzo[b][1,8]naphthyridine, 7-chloro-5-(cyclopropylamino)-5,10-dihydro-5-(trifluoromethyl)benzo[b][1,8]naphthyridine, 7-chloro-5-(i-propylamino)-5,10-dihydro-5-(trifluoromethyl)benzo[b][1,8]naphthyridine, 7-chloro-5-(N,N-dimethylaminoethoxy)-5,10-dihydro-5-(trifluoromethyl)benzo[b][1,8]naphthyridine, 7-chloro-5-(N-morpholinylethylamino)-5,10-dihydro-5-(trifluoromethyl)benzo[b][1,8]naphthyridine, 7-chloro-5-((1-methylcyclopropyl)methoxy)-5,10-dihydro-5-(trifluoromethyl)benzo[b][1,8]naphthyridine, 7-chloro-5-(3,3,3-trifluoroprop-1-oxy)-5,10-dihydro-5-(trifluoromethyl)benzo[b][1,8]naphthyridine, 7-chloro-5-(cyclopropylmethylamino)-5,10-dihydro-5-(trifluoromethyl)benzo[b][1,8]naphthyridine, 7-chloro-5-(methylamino)-5,10-dihydro-5-(trifluoromethyl)benzo[b][1,8]naphthyridine, 7-chloro-5-(ethylamino)-5,10-dihydro-5-(trifluoromethyl)benzo[b][1,8]naphthyridine, (S)-7-chloro-5-(cyclopropylethyl)-5,10-dihydro-5-(trifluoromethyl)benzo[b][1,8]naphthyridine, (R)-7-chloro-5-(cyclopropylethyl)-5,10-dihydro-5-(trifluoromethyl)benzo[b][1,8]naphthyridine, 7-fluoro-5-(cyclopropylmethoxy)-5,10-dihydro-5-(trifluoromethyl)benzo[b][1,8]naphthyridine, 7-fluoro-5-(cyclopropylethoxy)-5,10-dihydro-5-(trifluoromethyl)benzo[b][1,8]naphthyridine, 7-fluoro-5-(allyloxy)-5,10-dihydro-5-(trifluoromethyl)benzo[b][1,8]naphthyridine, 7-chloro-5-(phenylamino)-5,10-dihydro-5-(trifluoromethyl)benzo[b][1,8]naphthyridine, 7-chloro-5-(cyclopropylmethoxy)-2-methyl-5,10-dihydro-5-(trifluoromethyl)benzo[b][1,8]naphthyridine, 7-chloro-5-(n-butyl)-2-methyl-5,10-dihydro-5-(trifluoromethyl)benzo[b][1,8]naphthyridine, 7-chloro-5-(cyclopropylethyl)-2-methyl-5,10-dihydro-5-(trifluoromethyl)benzo[b][1,8]naphthyridine, 7-chloro-5-cyclopropylmethoxy-5-trifluoromethyl-5,10-dihydro-benzo[b][1,8]naphthyridine 1-oxide, 5-Allyloxy-7-fluoro-5-trifluoromethyl-5,10-dihydro-benzo[b][1,8]naphthyridine, 7-fluoro-5-trifluoromethyl-5,10-dihydro-benzo[b][1,8]naphthyridine-5-carbonitrile, 7-fluoro-5-trifluoromethyl-5,10-dihydro-benzo[b][1,8]naphthyridin-5-ol, 5-cyclopropylmethoxy-7-fluoro-5-trifluoromethyl-5,10-dihydro-benzo[b][1,8]naphthyridine 1-oxide, 7-chloro-5-prop-2-ynyloxy-5-trifluoromethyl-5,10-dihydro-benzo[b][1,8]naphthyridine 1-oxide, 7-chloro-5-(1-methyl-cyclopropylmethoxy)-5-trifluoromethyl-5,10-dihydro-benzo[b][1,8]naphthyridine 1-oxide, 7-chloro-5-(2-cyclopropy-ethoxy)-5-trifluoromethyl-5,10-dihydro-benzo[b][1,8]naphthyridine 1-oxide, (7-chloro-5-trifluoromethyl-5,10-dihydro-benzo[b][1,8]naphthyridin-5-yl)-isopropyl-amine, (7-chloro-5-trifluoromethyl-5,10-dihydro-benzo[b][1,8]naphthyridin-5-yl)-cyclobutylmethyl-amine, 7-chloro-5-(2-cyclopropyl-ethyl)-5-trifluoromethyl-5,10-dihydro-benzo[b][1,8]naphthyridine 1-oxide, 5-cyclobutylmethoxy-7-fluoro-5-trifluoromethyl-5,10-dihydro-benzo[b][1,8]naphthyridine 1-oxide, (7-fluoro-1-oxy-5-trifluoromethyl-5,10-dihydro-benzo[b][1,8]naphthyridin-5-yl)-isopropyl-amine, 5-cyclobutylmethoxy-7-fluoro-5-trifluoromethyl-5,10-dihydro-benzo[b][1,8]naphthyridin-2-ol, 7-chloro-5-(pyridin-2-ylmethoxy)-5-trifluoromethyl-5,10-dihydro-benzo[b][1,8]naphthyridine, 5-butyl-7-fluoro-5-trifluoromethyl-5,10-dihydro-benzo[b][1,8]naphthyridine, 7-chloro-1-oxy-5-trifluoromethyl-5,10-dihydro-benzo[b][1,8]naphthyridin-5-o 1,7-chloro-5-cyclopropylmethoxy-5-trifluoromethyl-5,10-dihydro-benzo[b][1,8]naphthyridine 1-oxide, 7-chloro-5-pyridin-2-ylmethyl-5-trifluoromethyl-5,10-dihydro-benzo[b][1,8]naphthyridine 1-oxide, 7-fluoro-5-pyridin-2-ylmethyl-5-trifluoromethyl-5,10-dihydro-benzo[b][1,8]naphthyridine, 5-cyclopropylmethoxy-7-fluoro-5-trifluoromethyl-5,10-dihydro-benzo[b][1,8]naphthyridine 1-oxide, 7-chloro-5-pyridin-2-ylmethyl-5-trifluoromethyl-5,10-dihydro-benzo[b][1,8]naphthyridine, 3,7-dichloro-5-cyclopropylmethoxy-5-trifluoromethyl-5,10-dihydro-benzo[b][1,8]naphthyridine, 3,7-dichloro-5-cyc(opropylmethoxy-5-trifluoromethyl-5,10-dihydro-benzo[b][1,8]naphthyridine 1-oxide, 3,7- dichloro-5-pentyl-5-trifluoromethyl-5,10-dihydro-benzo[b][1,8]naphthyridine 1-oxide, 5-(2-cyclopropyl-ethyl)-7-fluoro-5-trifluoromethyl-5,10-dihydro-benzo[b][1,8]naphthyridine, 5-(2-cyclopropyl-ethyl)-7-fluoro-5-trifluoromethyl-5,10-dihydro-benzo[b][1,8]naphthyridine 1-oxide, 3,7-dichloro-5-cyclopropylmethoxy-5-trifluoromethyl-5,10-dihydro-benzo[b][1,8]naphthyridine 1-oxide, 5-(2-cyclopropyl-ethyl)-7-fluoro-5-trifluoromethyl-5,10-dihydro-benzo[b][1,8]naphthyridine 1-oxide, 3-chloro-5-cyclopropylmethoxy-7-fluoro-5-trifluoromethyl-5,10-dihydro-benzo[b][1,8]naphthyridine, 3-chloro-5-cyclopropylmethoxy-7-fluoro-5-trifluoromethyl-5,10-dihydro-benzo[b][1,8]naphthyridine 1-oxide, 7-chloro-5-isobutoxy-5-trifluoromethyl-5,10-dihydro-benzo[b][1,8]naphthyridine 1-oxide, 5-butyl-7-chloro-5-trifluoromethyl-5,10-dihydro-benzo[b][1,8]naphthyridine 1-oxide, (S) 3-chloro-5-cyclopropylmethoxy-7-fluoro-5-trifluoromethyl-5,10-dihydro-benzo[b][1,8]naphthyridine 1-oxide, (7-chloro-5-trifluoromethyl-5,10-dihydro-benzo[b][1,8]naphthyridin-5-yl)-methanol, 7-fluoro-5-isobutoxy-5-trifluoromethyl-5,10-dihydro-benzo[b][1,8]naphthyridine 1-oxide, 7-fluoro-5-isopropoxy-5-trifluoromethyl-5,10-dihydro-benzo[b][1,8]naphthyridine 1-oxide, methanesulfonic acid 7-chloro-5-trifluoromethyl-5,10-dihydro-benzo[b][1,8]naphthyridin-5-ylmethyl ester, 7-chloro-5-isopropoxy-5-trifluoromethyl-5,10-dihydro-benzo[b][1,8]naphthyridine 1-oxide, 3-bromo-5-cyclopropylmethoxy-7-fluoro-5-trifluoromethyl-5,10-dihydro-benzo[b][1,8]naphthyridine 1-oxide, 5-butyl-7-fluoro-5-trifluoromethyl-5,10-dihydro-benzo[b][1,8]naphthyridine 1-oxide, 5-diisopropoxymethyl-7-fluoro-5-trifluoromethyl-5,10-dihydro-benzo[b][1,8]naphthyridine, 7-fluoro-5-isopropoxymethyl-5-trifluoromethyl-5,10-dihydro-benzo[b][1,8]naphthyridine 1-oxide, 7-chloro-5-isobutyl-5-trifluoromethyl-5,10-dihydro-benzo[b][1,8]naphthyridine 1-oxide, 7-chloro-5-propoxy-5-trifluoromethyl-5,10-dihydro-benzo[b][1,8]naphthyridine 1-oxide, (S) 7-fluoro-5-isobutoxy-5-trifluoromethyl-5,10-dihydro-benzo[b][1,8]naphthyridine 1-oxide, (R) 7-fluoro-5-isobutoxy-5-trifluoromethyl-5,10-dihydro-benzo[b][1,8]naphthyridine 1-oxide, (7-chloro-5-trifluoromethyl-5,10-dihydro-benzo[b][1,8]naphthyridin-5-yl)-acetaldehyde, 7-chloro-5-(2,2-diisopropoxy-ethyl)-5-trifluoromethyl-5,10-dihydro-benzo[b][1,8]naphthyridine, 7-chloro-5-(2-isopropoxy-ethyl)-5-trifluoromethyl-5,10-dihydro-benzo[b][1,8]naphthyridine, 2-(7-chloro-5-trifluoromethyl-5,10-dihydro-benzo[b][1,8]naphthyridin-5-yl)-ethanol, 7-chloro-5-(2-isopropoxy-ethyl)-5-trifluoromethyl-5,10-dihydro-benzo[b][1,8]naphthyridine 1-oxide, (R) 7-fluoro-5-(2-isopropoxy-ethyl)-5-trifluoromethyl-5,10-dihydro-benzo[b][1,8]naphthyridine 1-oxide, (7-fluoro-5-trifluoromethyl-5,10-dihydro-benzo[b][1,8]naphthyridin-5-yl)-acetic acid tert-butyl ester, (7-fluoro-1-oxy-5-trifluoromethyl-5,10-dihydro-benzo[b][1,8]naphthyridin-5-yl)-acetic acid tert-butyl ester, 7-chloro-5-cyclopropylmethoxy-5-(1,1-difluoro-ethyl)-5,10-dihydro-benzo[b][1,8]naphthyridine 1-oxide, 5-cyclopropylmethoxy-5-(1,1-difluoro-ethyl)-7-fluoro-5,10-dihydro-benzo[b][1,8]naphthyridine, 5-cyclopropylmethoxy-5-(1,1-difluoro-ethyl)-7-fluoro-5,10-dihydro-benzo[b][1,8]naphthyridine 1-oxide, 7-chloro-5-(1,1-difluoro-ethyl)-5-isobutoxy-5,10-dihydro-benzo[b][1,8]naphthyridine, 7-chloro-5-(1,1-difluoro-ethyl)-5-isobutoxy-5,10-dihydro-benzo[b][1,8]naphthyridine 1-oxide, (R) 7-chloro-5-cyclopropylmethoxy-5-(1,1-difluoro-ethyl)-5,10-dihydro-benzo[b][1,8]naphthyridine 1-oxide, (S) 7-chloro-5-cyclopropylmethoxy-5-(1,1-difluoro-ethyl)-5,10-dihydro-benzo[b][1,8]naphthyridine 1-oxide, 7-chloro-5-difluoromethyl-5-isopropoxymethyl-5,10-dihydro-benzo[b][1,8]naphthyridine, 7-chloro-5-difluoromethyl-5-isopropoxymethyl-5,10-dihydro-benzo[b][1,8]naphthyridine 1-oxide, 7-chloro-1,5-dihydro-5-(N-ethylaminomethyl)-5-(trifluoromethyl)benzo[b][1,8]napthyridine, 7-chloro-5,10-dihydro-5-(N-isopropylaminomethyl)-5-(trifluoromethyl)benzo[b][1,8]napthyridine, 7-chloro-5,10-dihydro-5-(N-isopropyl-N-ethylaminomethyl)-5-(trifluoromethyl)benzo[b][1,8]napthyridine, 7-chloro-5-(N,N-diethylaminomethyl)-5,10-dihydro-5-(trifluoromethyl)benzo[b][1,8]napthyridine, 5-(acetamidomethyl)-7-chloro-5,10-dihydro-5-(trifluoromethyl)benzo[b][1,8]napthyridine, 5,10-dihydro-7-fluoro-5-(N-methylsulfonylmethyl)-5-(trifluoromethyl)benzo[b][1,8]napthyridine, 5,10-dihydro-7-fluoro-5-(isopropylamidomethyl)-5-(trifluoromethyl)benzo[b][1,8]napthyridine, 5,10-dihydro-7-fluoro-5-(isopropylguanadinomethyl)-5-(trifluormethyl)benzo[b][1,8]napthyridine, 5,10-dihydro-7-fluoro-5-(N-isopropylmethyl)-5-(trifluoromethyl)benzo[b][1,8]napthyridine-1-(N-oxide), 5-(N,N-diethylaminomethyl)-5,10-dihydro-7-fluoro-5-(trifluoromethyl)benzo[b][1,8]napthyridine-1-(N-oxide), 5,10-dihydro-5-(N,N-dimethylaminomethyl)-7-fluoro-5-(trifluoromethyl)benzo[b][1,8]napthyridine-1-(N-oxide), 7-chloro-5,10-dihydro-5-(N-isopropylaminomethyl)-5-(trifluoromethyl)benzo[b][1,8]napthyridine-1-(N-oxide), 7-chloro-5-(N,N-diethylaminomethyl)-5,10-dihydro-5-(trifluoromethyl)benzo[b][1,8]napthyridine-1-(N-oxide), and 7-chloro-5,10-dihydro-5-(N,N-dimethylaminomethyl)-5-(trifluoromethyl)benzo[b][1,8]napthyridine-1-(N-oxide); by formula I of U.S. Pat. No. 6,596,729, e.g., 7-fluoro-2-methyl-5-[(6-methyl-2-pyridinyl)methyl]-5-(trifluoromethyl)-5,10-dihydrobenzo[b]-1,7-naphthyridin-1(2H)-one, 5-(2-cyclopropylethynyl)-7-fluoro-5-(trifluoromethyl)-5,10-dihydrobenzo[b]-1,7-naphthyridin-1(2H)-one, 7-fluoro-5-propyl-5-(trifluoromethyl)-5,10-dihydrobenzo[b]-1,7-naphthyridin-1(2H)-one, 5-butyl-7-fluoro-5-(trifluoromethyl)-5,10-dihydrobenzo[b]-1,7-naphthyridin-1(2H)-one, 7-fluoro-5-(4-fluorophenylmethyl)-5-(trifluoromethyl)-5,10-dihydrobenzo[b]-1,7-naphthyridin-1(2H)-one, 7-fluoro-5-(2-pyridylmethyl)-5-(trifluoromethyl)-5,10-dihydrobenzo[b]-1,7-naphthyridin-1(2H)-one, 7-fluoro-5-(isopropyl)-5-(trifluoromethyl)-5,10-dihydrobenzo[b]-1,7-naphthyridin-1(2H)-one, 7-fluoro-5-(3-pyridylmethyl)-5-(trifluoromethyl)-5,10-dihydrobenzo[b]-1,7-naphthyridin-1(2H)-one, 7-fluoro-5-(4-pyridylmethyl)-5-(trifluoromethyl)-5,10-dihydrobenzo[b]-1,7-naphthyridin-1(2H)-one, 7-fluoro-5-(3-propynyl)-5-(trifluoromethyl)-5,10-dihydrobenzo[b]-1,7-naphthyridin-1(2H)-one, 7-fluoro-5-(2-pyridylethynyl)-5-(trifluoromethyl)-5,10-dihydrobenzo[b]-1,7-naphthyridin-1(2H)-one, 7-fluoro-5-(2-(2-pyridyl)ethyl)-5-(trifluoromethyl)-5,10-dihydrobenzo[b]-1,7-naphthyridin-1(2H)-one, 3-chloro-7-fluoro-5-propyl-5-(trifluoromethyl)-5,10-dihydrobenzo[b]-1,7-naphthyridin-1(2H)-one, 7-fluoro-5-(3-propenyl)-5-(trifluoromethyl)-5,10-dihydrobenzo[b]-1,7-naphthyridin-1(2H)-one, 5-(2-cyclopropylethyl)-7-fluoro-5-(trifluoromethyl)-5,10-dihydrobenzo[b]-1,7-naphthyridin-1(2H)-one, 7-fluoro-5-(ethynyl)-5-(trifluoromethyl)-5,10-dihydrobenzo[b]-1,7-naphthyridin-1(2H)-one, 7-fluoro-5-(2-ethoxyethyl)-5-(trifluoromethyl)-5,10-dihydrobenzo[b]-1,7-naphthyridin-1(2H)-one, 5-butyl-7-chloro-5-trifluoromethyl-5,10-dihydrobenzo[b]-1,7-naphthyridin-1(2H)-one, 7-chloro-5-(2-pyridylmethyl)-5-trifluoromethyl-5,10-dihydrobenzo[b]-1,7-naphthyridin-1(2H)-one, 7-chloro-5-(2-cyclopropylethyl)-5-trifluoromethyl-5,10-dihydrobenzo[b]-1,7-naphthyridin-1(2H)-one, 7-chloro-5-cyclopropylethynyl-5-trifluoromethyl- 5,10-dihydrobenzo[b]-1,7-naphthyridin-1(2H)-one, 7-chloro-5-(N-cyclopropylaminomethyl)-5-trifluoromethyl-5,10-dihydrobenzo[b]-1,7-naphthyridin-1(2H)-one, 7-chloro-5-hydroxymethyl-5-trifluoromethyl-5,10-dihydrobenzo[b]-1,7-naphthyridin-1(2H)-one, 7-chloro-3-methyl-5-(2-pyridylmethyl)-5-trifluoromethyl-5,10-dihydrobenzo[b]-1,7-naphthyridin-1(2H)-one, 7-chloro-5-(2-cyclopropylethyl)-3-methyl-5-trifluoromethyl-5,10-dihydrobenzo[b]-1,7-naphthyridin-1(2H)-one, 7-chloro-5-(n-propoxymethyl)-5-trifluoromethyl-5,10-dihydrobenzo[b]-1,7-naphthyridin-1(2H)-one, 7-chloro-5-(i-propoxymethyl)-5-trifluoromethyl-5,10-dihydrobenzo[b]-1,7-naphthyridin-1(2H)-one, 7-chloro-5-(2-methoxyethyl)-5-trifluoromethyl-5,10-dihydrobenzo[b]-1,7-naphthyridin-1(2H)-one, 7-chloro-5-(i-propylaminomethyl)-5-trifluoromethyl-5,10-dihydrobenzo[b]-1,7-naphthyridin-1(2H)-one, 7-chloro-5-(N-methyl-N-1-propylaminomethyl)-5-trifluoromethyl-5,10-dihydrobenzo[b]-1,7-naphthyridin-1(2H)-one, 7-chloro-5-(cyclopropylaminomethyl)-5-trifluoromethyl-5,10-dihydrobenzo[b]-1,7-naphthyridin-1(2H)-one, 7-chloro-5-(n-propylaminomethyl)-5-trifluoromethyl-5,10-dihydrobenzo[b]-1,7-naphthyridin-1(2H)-one, 7-chloro-5-(cyclobutylaminomethyl)-5-trifluoromethyl-5,10-dihydrobenzo[b]-1,7-naphthyridin-1(2H)-one, 7-chloro-5-(i-butylaminomethyl)-5-trifluoromethyl-5,10-dihydrobenzo[b]-1,7-naphthyridin-1(2H)-one, 7-chloro-5-(i-propoxymethyl)-5-trifluoromethyl-5,10-dihydrobenzo[b]-1,7-naphthyridin-1(2H)-one, 7-cyano-5-(n-butyl)-5-trifluoromethyl-5,10-dihydrobenzo[b]-1,7-naphthyridin-1(2H)-one, 7-cyano-5-(i-propoxymethyl)-5-trifluoromethyl-5,10-dihydrobenzo[b]-1,7-naphthyridin-1(2H)-one, 7-chloro-5-(cyclopropylsulfanylmethyl)-5-trifluoromethyl-5,10-dihydrobenzo[b]-1,7-naphthyridin-1(2H)-one, 7-chloro-5-(cyclopropanesulfinylmethyl)-5-trifluoromethyl-5,10-dihydrobenzo[b]-1,7-naphthyridin-1(2H)-one, 7-chloro-5-(t-butylsulfinylmethyl)-5-trifluoromethyl-5,10-dihydrobenzo[b]-1,7-naphthyridin-1(2H)-one, 7-chloro-5-(methylsulfanylmethyl)-5-trifluoromethyl-5,10-dihydrobenzo[b]-1,7-naphthyridin-1(2H)-one, 7-chloro-5-(ethylsulfanylmethyl)-5-trifluoromethyl-5,10-dihydrobenzo[b]-1,7-naphthyridin-1(2H)-one, 7-chloro-5-(i-propylsulfanylmethyl)-5-trifluoromethyl-5,10-dihydrobenzo[b]-1,7-naphthyridin-1(2H)-one, 7-fluoro-5-(i-propylsulfanylmethyl)-5-trifluoromethyl-5,10-dihydrobenzo[b]-1,7-naphthyridin-1(2H)-one, 7-chloro-5-(t-butylsulfanylmethyl)-5-trifluoromethyl-5,10-dihydrobenzo[b]-1,7-naphthyridin-1(2H)-one, 7-chloro-5-(cyclopropylmethoxymethyl)-5-trifluoromethyl-5,10-dihydrobenzo[b]-1,7-naphthyridin-1(2H)-one, 7-chloro-5-(cyclobutoxymethyl)-5-trifluoromethyl-5,10-dihydrobenzo[b]-1,7-naphthyridin-1(2H)-one, 5-(cyclobutoxymethyl)-7-fluoro-5-trifluoromethyl-5,10-dihydrobenzo[b]-1,7-naphthyridin-1(2H)-one, 5-(cyclopropylmethoxymethyl)-7-fluoro-5-trifluoromethyl-5,10-dihydrobenzo[b]-1,7-naphthyridin-1(2H)-one, 7-chloro-3-methyl-5-(i-propoxymethyl)-5-trifluoromethyl-5,10-dihydrobenzo[b]-1,7-naphthyridin-1(2H)-one, 7-chloro-3-methyl-5-(n-butyl)-5-trifluoromethyl-5,10-dihydrobenzo[b]-1,7-naphthyridin-1(2H)-one, 7-cyano-3-methyl-5-(n-butyl)-5-trifluoromethyl-5,10-dihydrobenzo[b]-1,7-naphthyridin-1(2H)-one, 7-chloro-2-methyl-5-(i-propoxymethyl)-5-trifluoromethyl-5,10-dihydrobenzo[b]-1,7-naphthyridin-1(2H)-one, 3,7-dichloro-5-(n-butyl)-5-trifluoromethyl-5,10-dihydrobenzo[b]-1,7-naphthyridin-1(2H)-one, 4,7-dichloro-5-(n-butyl)-5-trifluoromethyl-5,10-dihydrobenzo[b]-1,7-naphthyridin-1(2H)-one, 7-chloro-5-(ethoxyethyl)-5-trifluoromethyl-5,10-dihydrobenzo[b]-1,7-naphthyridin-1(2H)-one, 7-chloro-5-(n-butyl)-5-methyl-5,10-dihydrobenzo[b]-1,7-naphthyridin-1(2H)-one, 7-chloro-5-(i-propoxymethyl)-5-methyl-5,10-dihydrobenzo[b]-1,7-naphthyridin-1(2H)-one, 7-chloro-5-(n-butyl)-5-cyano-5,10-dihydrobenzo[b]-1,7-naphthyridin-1(2H)-one, 7-chloro-5-(n-butyl)-5-(hydroxymethyl)-5,10-dihydrobenzo[b]-1,7-naphthyridin-1(2H)-one, 7-chloro-5-(n-butyl)-5-difluoromethyl-5,10-dihydrobenzo[b]-1,7-naphthyridin-1(2H)-one, 7-chloro-5-(i-propoxymethyl)-5-difluoromethyl-5,10-dihydrobenzo[b]-1,7-naphthyridin-1(2H)-one, 5-(n-butyl)-5-(1,1-difluoroethyl)-7-fluoro-5,10-dihydrobenzo[b]-1,7-naphthyridin-1(2H)-one, 7-chloro-5-(n-butyl)-5-(1,1-difluoroethyl)-5,10-dihydrobenzo[b]-1,7-naphthyridin-1(2H)-one, 7-cyano-5-(n-butyl)-5-(1,1-difluoroethyl)-5,10-dihydrobenzo[b]-1,7-naphthyridin-1(2H)-one, 7-chloro-5-(ethoxymethyl)-5-(1,1-difluoroethyl)-5,10-dihydrobenzo[b]-1,7-naphthyridin-1(2H)-one, 5-(allyl)-7-fluoro-5-trifluoromethyl-5,10-dihydrobenzo[b]-1,7-naphthyridin-1(2H)-one, 5-(2-methyl-1-propenyl)-7-fluoro-5-trifluoromethyl-5,10-dihydrobenzo[b]-1,7-naphthyridin-1(2H)-one, 5-(1-propynyl)-7-fluoro-5-trifluoromethyl-5,10-dihydrobenzo[b]-1,7-naphthyridin-1(2H)-one, 5-(cyanomethyl)-7-fluoro-5-trifluoromethyl-5,10-dihydrobenzo[b]-1,7-naphthyridin-1(2H)-one, 5-(2-(ethylamino)ethyl)-7-fluoro-5-trifluoromethyl-5,10-dihydrobenzo[b]-1,7-naphthyridin-1(2H)-one, 5-(2-(dimethylamino)ethyl)-7-fluoro-5-trifluoromethyl-5,10-dihydrobenzo[b]-1,7-naphthyridin-1(2H)-one, 542-(methylamino)ethyl)-7-fluoro-5-trifluoromethyl-5,10-dihydrobenzo[b]-1,7-naphthyridin-1(2H)-one, 5-(2-ethoxyethyl)-7-fluoro-5-trifluoromethyl-5,10-dihydrobenzo[b]-1,7-naphthyridin-1(2H)-one, 5-(2-(i-propylamino)ethyl)-7-fluoro-5-trifluoromethyl-5,10-dihydrobenzo[b]-1,7-naphthyridin-1(2H)-one, 5-(2-(diethylamino)ethyl)-7-fluoro-5-trifluoromethyl-5,10-dihydrobenzo[b]-1,7-naphthyridin-1(2H)-one, 5-(2-(cyclopropylamino)ethyl)-7-fluoro-5-trifluoromethyl-5,10-dihydrobenzo[b]-1,7-naphthyridin-1(2H)-one, 5-(pentyl)-7-fluoro-5-trifluoromethyl-5,10-dihydrobenzo[b]-1,7-naphthyridin-1(2H)-one, 5-(i-butyl)-7-fluoro-5-trifluoromethyl-5,10-dihydrobenzo[b]-1,7-naphthyridin-1(2H)-one, 5-(vinyl)-7-fluoro-5-trifluoromethyl-5,10-dihydrobenzo[b]-1,7-naphthyridin-1(2H)-one, 5-(imidazolylethyl)-7-fluoro-5-trifluoromethyl-5,10-dihydrobenzo[b]-1,7-naphthyridin-1(2H)-one, 5-(2-i-propylamino)ethyl)-7-fluoro-5-trifluoromethyl-5,10-dihydrobenzo[b]-1,7-naphthyridin-1(2H)-one, 5-(1,2,4-triazolylethyl)-7-fluoro-5-trifluoromethyl-5,10-dihydrobenzo[b]-1,7-naphthyridin-1(2H)-one, 5-(i-propylaminomethyl)-7-fluoro-5-trifluoromethyl-5,10-dihydrobenzo[b]-1,7-naphthyridin-1(2H)-one, 5-(i-propoxymethyl)-7-fluoro-5-trifluoromethyl-5,10-dihydrobenzo[b]-1,7-naphthyridin-1(2H)-one, 5-(2-(methylethylamino)ethyl)-7-fluoro-5-trifluoromethyl-5,10-dihydrobenzo[b]-1,7-naphthyridin-1(2H)-one, 5-(2-(i-propylethylamino)ethyl)-7-fluoro-5-trifluoromethyl-5,10-dihydrobenzo[b]-1,7-naphthyridin-1(2H)-one, 5-(2-(pyrrolidinyl)ethyl)-7-fluoro-5-trifluoromethyl-5,10-dihydrobenzo[b]-1,7-naphthyridin-1(2H)-one, 5-(2-(methoxy)ethyl)-7-fluoro-5-trifluoromethyl-5,10-dihydrobenzo[b]-1,7-naphthyridin-1(2H)-one, 5-(1-propoxymethyl)-7-fluoro-5-trifluoromethyl-5,10-dihydrobenzo[b]-1,7-naphthyridin-1(2H)-one, 5-(3-pentanylaminomethyl)-7-fluoro-5-trifluoromethyl-5,10-dihydrobenzo[b]-1,7-naphthyridin-1(2H)-one, 5-(dimethoxymethyl)-7-fluoro-5-trifluoromethyl-5,10-dihydrobenzo[b]-1,7-naphthyridin-1(2H)-one, 5-(i-butylami nomethyl)-7-fluoro-5-trifluoromethyl-5,10-dihydrobenzo[b]-1,7-naphthyridin-1(2H)-one, 5-(cyclopropylmethylaminomethyl)-7-fluoro-5-trifluoromethyl-5,10-dihydrobenzo[b]-1,7-naphthyridin-1(2H)-one, 5-(allylaminomethyl)-7-fluoro-5-trifluoromethyl-5,10-dihydrobenzo[b]-1,7-naphthyridin-1(2H)-one, 5-((R)-sec-butylaminomethyl)-7-fluoro-5-trifluoromethyl-5,10-dihydrobenzo[b]-1,7-naphthyridin-1(2H)-one, 5-((S)-sec-butylaminomethyl)-7-fluoro-5-trifluoromethyl-5,10-dihydrobenzo[b]-1,7-naphthyridin-1(2H)-one, 5-(diethoxymethyl)-7-fluoro-5-trifluoromethyl-5,10-dihydrobenzo[b]-1,7-naphthyridin-1(2H)-one, 3-chloro-5-(propyl)-7-fluoro-5-trifluoromethyl-5,10-dihydrobenzo[b]-1,7-naphthyridin-1(2H)-one, 5-(butyl)-7-fluoro-2-methyl-5-trifluoromethyl-5,10-dihydrobenzo[b]-1,7-naphthyridin-1(2H)-one, 5-(2-(i-propoxy)ethyl)-7-fluoro-2-methyl-5-trifluoromethyl-5,10-dihydrobenz o[b]-1,7-naphthyridin-1(2H)-one, 5-(i-propylaminomethyl)-7-fluoro-2-methyl-5-trifluoromethyl-5,10-dihydrobenzo[b]-1,7-naphthyridin-1(2H)-one, 5-(i-propoxymethyl)-7-fluoro-2-methyl-5-trifluoromethyl-5,10-dihydrobenzo[b]-1,7-naphthyridin-1(2H)-one, 5-(2-ethoxyethyl)-7-fluoro-2-methyl-5-trifluoromethyl-5,10-dihydrobenzo[b]-1,7-naphthyridin-1(2H)-one, 5-(sec-butylaminomethyl)-7-fluoro-2-methyl-5-trifluoromethyl-5,10-dihydrobenzo[b]-1,7-naphthyridin-1(2H)-one, 5-(cyclopentylaminomethyl)-7-fluoro-5-trifluoromethyl-5,10-dihydrobenzo[b]-1,7-naphthyridin-1(2H)-one, 5-(cyclobutylaminomethyl)-7-fluoro-5-trifluoromethyl-5,10-dihydrobenzo[b]-1,7-naphthyridin-1(2H)-one, 5-(dimethylaminomethyl)-7-fluoro-5-trifluoromethyl-5,10-dihydrobenzo[b]-1,7-naphthyridin-1(2H)-one, 5-(pyrrolidinylmethyl)-7-fluoro-5-trifluoromethyl-5,10-dihydrobenzo[b]-1,7-naphthyridin-1(2H)-one, 5-(cyclopropylaminomethyl)-7-fluoro-5-trifluoromethyl-5,10-dihydrobenzo[b]-1,7-naphthyridin-1(2H)-one, 5-(2-(dimethoxy)ethyl)-7-fluoro-5-trifluoromethyl-5,10-dihydrobenzo[b]-1,7-naphthyridin-1(2H)-one, 5-(2-(diethoxy)ethyl)-7-fluoro-5-trifluoromethyl-5,10-dihydrobenzo[b]-1,7-naphthyridin-1(2H)-one, 5-(2-(1,3-dioxolanyl)methyl)-7-fluoro-5-trifluoromethyl-5,10-dihydrobenzo[b]-1,7-naphthyridin-1(2H)-one, and 5-(2-(methoxy)ethyl)-7-fluoro-5-trifluoromethyl-5,10-dihydrobenzo[b]-1,7-naphthyridin-1(2H)-one; by formula I of U.S. Pat. No. 6,825,210, e.g., 3,7-dichloro-5-isopropoxymethyl-5-trifluoromethyl-5,10-dihydro-benzo[b][1,8]naphthyridine, 3,7-dichloro-5-isopropoxymethyl-5-trifluoromethyl-5,10-dihydro-benzo[b][1,8]naphthyridine 1-oxide, 3-chloro-7-fluoro-5-isopropoxymethyl-5-trifluoromethyl-5,10-dihydro-benzo[b][1,8]naphthyridine, 3-chloro-7-fluoro-5-isopropoxymethyl-5-trifluoromethyl-5,10-dihydro-benzo[b][1,8]naphthyridine 1-oxide, 3-chloro-5-isopropoxymethyl-5-trifluoromethyl-4-a,5,10,10a-tetrahydro-benzo[b][1,8]naphthyridine-7-carbonitrile, 3-chloro-5-isopropoxymethyl-1-oxy-5-trifluoromethyl-4-a,5,10,10a-tetrahydro-benzo[b][1,8]naphthyridine-7-carbonitrile, 3-bromo-7-cyano-5-trifluoromethyl-5-isopropoxymethyl-5,10-dihydrobenzo[b][1,8]naphthyridine, 3-bromo-7-cyano-5-trifluoromethyl-5-isopropoxymethyl-5,10-dihydrobenzo[b][1,8]naphthyridine-1-N-oxide, 3,7-dicyano-5-trifluoromethyl-5-isopropoxymethyl-5,10-dihydrobenzo[b][1,8]naphthyridine, and 3,7-dicyano-5-trifluoromethyl-5-isopropoxymethyl-5,10-dihydrobenzo[b][1,8]naphthyridine-1-N-oxide, (R)3,7-dichloro-5-isopropoxymethyl-5-trifluoromethyl-5,10-dihydro-benzo[b][1,8]naphthyridine, (R)3,7-dichloro-5-isopropoxymethyl-5-trifluoromethyl-5,10-dihydro-benzo[b][1,8]naphthyridine 1-oxide, (R)$_3$-chloro-7-fluoro-5-isopropoxymethyl-5-trifluoromethyl-5,10-dihydro-benzo[b][1,8]naphthyridine, (R)$_3$-chloro-7-fluoro-5-isopropoxymethyl-5-trifluoromethyl-5,10-dihydro-benzo[b][1,8]naphthyridine 1-oxide, (R)$_3$-chloro-5-isopropoxymethyl-5-trifluoromethyl-4-a,5,10,10a-tetrahydro-benzo[b][1,8]naphthyridine-7-carbonitrile, (R)$_3$-chloro-5-isopropoxymethyl-1-oxy-5-trifluoromethyl-4-a,5,10,10a-tetrahydro-benzo[b][1,8]naphthyridine-7-carbonitrile, (R)$_3$-bromo-7-cyano-5-trifluoromethyl-5-isopropoxymethyl-5,10-dihydrobenzo[b][1,8]naphthyridine, (R)$_3$-bromo-7-cyano-5-trifluoromethyl-5-isopropoxymethyl-5,10-dihydrobenzo[b][1,8]naphthyridine-1-N-oxide, (R)3,7-dicyano-5-trifluoromethyl-5-isopropoxymethyl-5,10-dihydrobenzo[b][1,8]naphthyridine, and (R)3,7-dicyano-5-trifluoromethyl-5-isopropoxymethyl-5,10-dihydrobenzo[b][1,8]naphthyridine-1-N-oxide; and by formula I of U.S. Pat. No. 6,844,340, e.g., b-chloro-10-(isopropoxmethyl)-10-(trifluoromethyl)-5,10-dihydropyrimido[5,4-b]quinolin-4 (3H)-one, 8-cyano-10-(isopropoxymethyl)-10-(trifluoromethyl)-5,10-dihydropyrimido[5,4-b]quinolin-4(3H)-one, 8-cyano-10-(isopropoxymethyl)-2-methyl-10-(trifluoromethyl)-5,10-dihydropyrimido[5,4-b]quinolin-4(3H)-one, 8-cyano-10-(2-cyclopropylethyl)-10-(trifluoromethyl)-5,10-dihydropyrimido-[5,4-b]quinolin-4(3H)-one, and (R)-8-cyano-10-(isopropoxymethyl)-10-(trifluoromethyl)-5,10-dihydropyrimido-[5,4-b]quinolin-4(3H)-one. Additional analogs include phosphonate derivatives of efavirenz, e.g, compounds described in U.S. Pat. No. 7,462,608.

K-Strophanthin

K-strophanthin (cymarine) is a cardiac glycoside derived from Strophanthus plant species. Analogs of strophanthins include other cardiac glycosides and their aglycone derivatives. Cardiac glycosides are derived from the cyclopentanoperhydro-phenanthrene nucleus of steroid compounds and are characterized by lactone rings joined by an ether linkage to one or more sugar residues. Aglycone derivatives of cardiac glycosides lack the carbohydrates characterstic of the cardiac glycosides. Exemplary analogs of strophanthins include, but are not limited to, G-strophanthin (ouabain), lanatoside A, desacetyllanatoside A, actyl digitoxin, digitoxin, lanatoside c, desacetyllanatoside c, digoxin, strophanthoside, scillaren A, proscillaridin A, uzarin, digitoxose, gitoxin, strophanthidine-3b-digitoxoside, strophanthidin aL-rhamnopyranoside, strophanthidol, oleandrin, acovenoside A, strophanthidine digilanobioside, strophanthidin-D-cymaroside, digitoxigenin-L-rhamnoside digitoxigenin theretoside, and the like. Aglycones include, but are not limited to, strophanthidin, digitoxigenin, uzarigenin, digoxigenin, digoxigenin 3,12-diacetate, gitoxigenin, gitoxigenin 3-acetate, gitoxigenin 3,16-diacetate, 16-acetyl gitoxigenin, acetyl strophanthidin, ouabagenin, 3-epidigoxigenin, and the like.

Mycophenolate Mofetil

Mycophenolate mofetil is an immunosuppressant described in U.S. Pat. No. 4,753,935. Analogs of mycophenolate mofetil are described by formula A in U.S. Pat. No. 4,753,935; by formulae I and II in U.S. Pat. No. 4,861,776, e.g., 2-(pyrrolidin-1-yl)ethyl E-6-(1,3-dihydro-4-hydroxy-6-methoxy-7-methyl-3-oxo-5-isobenzofuranyl)-4-methyl-4-hexenoate, 2-(isoxazolidin-1-yl)ethyl E-6-(1,3-dihydro-4-hydroxy-6-methoxy-7-methyl-3-oxo-5-isobenzofuranyl)-4-methyl-4-hexenoate, 2-(thiazolidin-1-yl)ethyl E-6-(1,3-dihydro-4-hydroxy-6-methoxy-7-methyl-3-oxo-5-isobenzofuranyl)-4-methyl-4-hexenoate, 2-(imidazolidin-1-yl)ethyl E-6-(1,3-dihydro-4-hydroxy-6-methoxy-7-methyl-3-oxo-5-isobenzofuranyl)-4-methyl-4-hexenoate, 2-(2-methyl-1,2-pyrazolidin-1-yl)ethyl E-6-(1,3-dihydro-4-hydroxy-6-methoxy-7-methyl-3-oxo-5-isobenzofuranyl)-4-methyl-4-hexenoate, 2-(piperidin-1-yl)ethyl E-6-(1,3- dihydro-4-hydroxy-6-methoxy-7-methyl-3-oxo-5-isobenzofuranyl)-4-methyl-4-hexenoate, 2-(2-oxazin-1-yl)ethyl E-6-(1,3-dihydro-4-hydroxy-6-methoxy-7-methyl-3-oxo-5-isobenzofuranyl)-4-methyl-4-hexenoate, 2-(4-thiazin-1-yl)ethyl E-6-(1,3-dihydro-4-hydroxy-6-methoxy-7-methyl-3-oxo-5-isobenzofuranyl)-4-methyl-4-hexenoate, 2-(piperazin-1-yl)ethyl E-6-(1,3-dihydro-4-hydroxy-6-methoxy-7-methyl-3-oxo-5-isobenzofuranyl)-4-methyl-4-hexenoate, 2-(4-methylpiperazin-1-yl)ethyl E-6-(1,3-dihydro-4-hydroxy-6-methoxy-7-methyl-3-oxo-5-isobenzofuranyl)-4-methyl-4-hexenoate, 2-(3-methyl-1,3-perhydrodiazin-1-yl)ethyl E-6-(1,3-dihydro-4-hydroxy-6-methoxy-7-methyl-3-oxo-5-isobenzofuranyl)-4-methyl-4-hexenoate, 2-(perhydroazepin-1-yl)ethyl E-6-(1,3-dihydro-4-hydroxy-6-methoxy-7-methyl-3-oxo-5-isobenzofuranyl)-4-methyl-4-hexenoate, 2-(perhydro-2-oxazepin-1-yl)ethyl E-6-(1,3-dihydro-4-hydroxy-6-methoxy-7-methyl-3-oxo-5-isobenzofuranyl)-4-methyl-4-hexenoate, 2-(perhydro-4-thiazepin-1-yl)ethyl E-6-(1,3-dihydro-4-hydroxy-6-methoxy-7-methyl-3-oxo-5-isobenzofuranyl)-4-methyl-4-hexenoate, 2-(1,2-perhydrodiazepin-1-yl)ethyl E-6-(1,3-dihydro-4-hydroxy-6-methoxy-7-methyl-3-oxo-5-isobenzofuranyl)-4-methyl-4-hexenoate, 2-(3-ethyl-1,3-perhydrodiazepin-1-yl)ethyl E-6-(1,3-dihydro-4-hydroxy-6-methoxy-7-methyl-3-oxo-5-isobenzofuranyl)-4-methyl-4-hexenoate, 3-(pyrrolidin-1-yl)propyl E-6-(1,3-dihydro-4-hydroxy-6-methoxy-7-methyl-3-oxo-5-isobenzofuranyl)-4-methyl-4-hexenoate, 3-(piperidin-1-yl)propyl E-6-(1,3-dihydro-4-hydroxy-6-methoxy-7-methyl-3-oxo-5-isobenzofuranyl)-4-methyl-4-hexenoate, 3-(morpholin-1-yl)propyl E-6-(1,3-dihydro-4-hydroxy-6-methoxy-7-methyl-3-oxo-5-isobenzofuranyl)-4-methyl-4-hexenoate, 3-(perhydroazepin-1-yl)propyl E-6-(1,3-dihydro-4-hydroxy-6-methoxy-7-methyl-3-oxo-5-isobenzofuranyl)-4-methyl-4-hexenoate, 4-(pyrazolidin-1-yl)butyl E-6-(1,3-dihydro-4-hydroxy-6-methoxy-7-methyl-3-oxo-5-isobenzofuranyl)-4-methyl-4-hexenoate, 4-(piperidin-1-yl)butyl E-6-(1,3-dihydro-4-hydroxy-6-methoxy-7-methyl-3-oxo-5-isobenzofuranyl)-4-methyl-4-hexenoate, 4-(morpholin-1-yl)butyl E-6-(1,3-dihydro-4-hydroxy-6-methoxy-7-methyl-3-oxo-5-isobenzofuranyl)-4-methyl-4-hexenoate, 4-(4-thiazin-1-yl)butyl E-6-(1,3-dihdydro-4-hydroxy-6-methoxy-7-methyl-3-oxo-5-isobenzofuranyl)-4-methyl-4-hexenoate, 4-(perhydro-2-oxazepin-1-yl)butyl E-6-(1,3-dihydro-4-hydroxy-6-methoxy-7-methyl-3-oxo-5-isobenzofuranyl)-4-methyl-4-hexenoate, 4-(4-t-butyl-1,4-perhydrodiazepin-1-yl)butyl E-6-(1,3-dihydro-4-hydroxy-6-methoxy-7-methyl-3-oxo-5-isobenzofuranyl)-4-methyl-4-hexenoate, morpholinoethyl (E)-6-(1,3-dihydro-4-heptanoyloxy-6-methoxy-7-methyl-3-oxo-5-isobenzofuranyl)-4-methyl-4-hexenoate, morpholinoethyl (E)-6-{1,3-dihydro-4-[N-(4-carbomethoxyphenyl) carbamoyloxy]-6-methoxy-7-methyl-3-oxo-5-isobenzofuranyl}-4-methyl-4-hexenoate, morpholinoethyl (E)-6-[1,3-dihydro-4-(N,N-diethylcarbamoyloxy)-6-methoxy-7-methyl-3-oxo-5-isobenzofuranyl]-4-methyl-4-hexenoate, morpholinoethyl (E)-6-[1,3-dihydro-4-(N-methyl-N-isobutylcarbamoyloxy)-6-methoxy-7-methyl-3-oxo-5-isobenzofuranyl]-4-methyl-4-hexenoate, morpholinoethyl (E)-6-{1,3-dihydro-4-[N-(4-carboethoxyphenyl)-N-ethylcarbamoyloxy]-6-methoxy-7-methyl-3-oxo-5-iso-benzofuranyl}-4-methyl-4-hexenoate, morpholinoethyl (E)-6-(1,3-dihydro-4-thiopropionoyloxy-6-methoxy-7-methyl-3-oxo-5-isobenzofuranyl)-4-methyl-4-hexenoate, morpholinoethyl (E)-6-(1,3-dihydro-4-thiopivaloyloxy-6-methoxy-7-methyl-3-oxo-5-isobenzofuranyl)-4-methyl-4-hexenoate, morpholinoethyl (E)-6-(1,3-dihydro-4-thioheptanoyloxy-6-methoxy-7-methyl-3-oxo-5-isobenzofuranyl)-4-methyl-4-hexenoate, morpholinoethyl (E)-6-(1,3-dihydro-4-thiobenzoyloxy-6-methoxy-7-methyl-3-oxo-5-isobenzofuranyl)-4-methyl-4-hexenoate, morpholinoethyl (E)-6-{1,3-dihydro-4-[N-(4-carboethoxyphenyl)thiocarbamoyloxy]-6-methoxy-7-methyl-3-oxo-5-isobenzofuranyl}-4-methyl-4-hexenoate, morpholinoethyl (E)-6-[1,3-dihydro-4-(N,N-diethylthiocarbamoyloxy)-6-methoxy-7-methyl-3-oxo-5-isobenzofuranyl]-4-methyl-4-hexenoate, morpholinoethyl (E)-6-[1,3-dihydro-4-(N-methyl-N-isobutylthiocarbamoyloxy)-6-methoxy-7-methyl-3-oxo-5-isobenzofuranyl]-4-methyl-4-hexenoate, morpholinoethyl (E)-6-{1,3-dihydro-4-[N-(4-carboethoxyphenyl)-N-ethylthiocarbamoyloxy]-6-methoxy-7-methyl-3-oxo-5-iso-benzofuranyl}-4-methyl-4-hexenoate, morpholinoethyl (E)-6-[1,3-dihydro-4-(carboethoxy-carbonyloxy)-6-methoxy-7-methyl-3-oxo-5-isobenzofuranyl]-4-methyl-4-hexenoate, morpholinoethyl (E)-6-[1,3-dihydro-4-(carbomethoxyethanoyloxy)-6-methoxy-7-methyl-3-oxo-5-isobenzofuranyl]-4-methyl-4-hexenoate, morpholinoethyl (E)-6-[1,3-dihydro-4-(carboethoxyethanoyloxy)-6-methoxy-7-methyl-3-oxo-5-isobenzofuranyl]-4-methyl-4-hexenoate, morpholinoethyl (E)-6-[1,3-dihydro-4-(3-carbomethoxypropionyloxy)-6-methoxy-7-methyl-3-oxo-5-isobenzofuranyl]-4-methyl-4-hexenoate, morpholinoethyl (E)-6-[1,3-dihydro-4-(3-carboethoxypropionyloxy)-6-methoxy-7-methyl-3-oxo-5-isobenzofuranyl]-4-methyl-4-hexenoate, morpholinoethyl (E)-6-[1,3-dihydro-4-(4-carbomethoxybutanoyloxy)-6-methoxy-7-methyl-3-oxo-5-isobenzofuranyl]-4-methyl-4-hexenoate, morpholinoethyl (E)-6-[1,3-dihydro-4-(5-carbomethoxypentanoyloxy)-6-methoxy-7-methyl-3-oxo-5-isobenzofuranyl]-4-methyl-4-hexenoate, 2-(thiazolidin-1-yl)ethyl E-6-[1,3-dihydro-4-(2-methylpropionyloxy)-6-methoxy-7-methyl-3-oxo-5-isobenzofuranyl]-4-methyl-4-hexenoate, 2-(piperidin-1-yl)ethyl E-6-(1,3-dihydro-4-pivaloyloxy-6-methoxy-7-methyl-3-oxo-5-isobenzofuranyl)-4-methyl-4-hexenoate, 3-(morpholin-1-yl)propyl E-6-(1,3-dihydro-4-adamantoyloxy-6-methoxy-7-methyl-3-oxo-5-isobenzofuranyl)-4-methyl-4-hexenoate, 4-(perhydro-2-oxazepin-1-yl)butyl E-6-(1,3-dihydro-4-benzoyloxy-6-methoxy-7-methyl-3-oxo-5-isobenzofuranyl)-4-methyl-4-hexenoate, 2-(4-thiazin-1-yl)ethyl E-6-{1,3-dihydro-4-[N-(4-carbomethoxyphenyl)thiocarbamoloxy]-6-methoxy-7-methyl-3-oxo-5-isobenzofuranyl}-4-methyl-4-hexenoate, 3-(morpholin-1-yl)propyl (E)-6-(1,3-dihydro-4-carboethoxycarbonyloxy-6-methoxy-7-methyl-3-oxo-5-isobenzofuranyl)-4-methyl-4-hexenoate, 3-(morpholin-1-yl)propyl (E)-6-(1,3-dihydro-4-carbomethoxyethanoyloxy-6-methoxy-7-methyl-3-oxo-5-isobenzofuranyl)-4-methyl-4-hexenoate, 3-(morpholin-1-yl)propyl (E)-6-(1,3-dihydro-4-carboethoxyethanoyloxy-6-methoxy-7-methyl-3-oxo-5-isobenzofuranyl)-4-methyl-4-hexenoate, and 3-(morpholin-1-yl)propyl (E)-6-[1,3-dihydro-4-(3-carbomethoxypropionyloxy)-6-methoxy-7-methyl-3-oxo-5-isobenzofuranyl]-4-methyl-4-hexenoate; by formula I in U.S. Pat. No. 5,380,879, e.g., methyl (E)-6-(1,3-dihydro-4-hydroxy-6-methoxy-7-methyl-3-oxoisobenzofuran-5-yl)-4-methyl-4-hexenoate, methyl (E)-6-(1,3-dihydro-4-trifluoromethylsulfonyloxy-6-methoxy-7-methyl-3-oxoisobenzofuran-5-yl)-4-methyl-4-hexenoate, methyl (E)-6-(1,3-dihydro-4-cyano-6-methoxy-7-methyl-3-oxoisobenzofuran-5-yl)-4-methyl-4-hexenoate, 2-(morpholin-4-yl)ethyl E-6-[1,3-dihydro-4-(3,3-dimethylureido)-6-methoxy-7-methyl-3-oxoisobenzofuran-5-yl]-4-methyl-4-hexenoate, 2-(morpholin-4-yl)ethyl E-6-[1,3-dihydro-4-(3-methyl)ureido-6-methoxy-7-methyl-3-oxoisobenzofuran-5-yl]-4-methyl-4-hexenoate, 2-(morpholin-4-yl)ethyl (E)-6-(1,3-dihydro-4-ureido-6- methoxy-7-methyl-3-oxoisobenzofuran-5-yl)-4-methyl-4-hexenoate, 2-(morpholin-4-yl)ethyl (E)-6-[1,3-dihydro-4-(3,3-diethyl)ureido-6-methoxy-7-methyl-3-oxoisobenzofuran-5-yl]-4-methyl-4-hexenoate, 2-(morpholin-4-yl)ethyl (E)-6-[1,3-dihydro-4-(3-ethyl)ureido-6-methoxy-7-methyl-3-oxoisobenzofuran-5-yl]-4-methyl-4-hexenoate, 2-(morpholin-4-yl)ethyl (E)-6-[1,3-dihydro-4-(3-methyl-4-3-ethyl)ureido-6-methoxy-7-methyl-3-oxoisobenzofuran-5-yl]-4-methyl-4-hexenoate, 2-(morpholin-4-yl)ethyl (E)-6-[1,3-dihydro-4-(3,3-diphenyl)ureido-6-methoxy-7-methyl-3-oxoisobenzofuran-5-yl]-4-methyl-4-hexenoate, 2-(morpholin-4-yl)ethyl (E)-6-[1,3-dihydro-4-(3-phenyl)ureido-6-methoxy-7-methyl-3-oxoisobenzofuran-5-yl]-4-methyl-4-hexenoate; and 2-(morpholin-4-yl)ethyl (E)-6-[1,3-dihydro-4-(3-methyl-4-3-phenyl)ureido-6-methoxy-7-methyl-3-oxoisobenzofuran-5-yl]-4-methyl-4-hexenoate.2-(pyrrolidin-1-yl)ethyl (E)-6-[1,3-dihydro-4-(3,3-dimethylureido)-6-methoxy-7-methyl-3-oxoisobenzofuran-5-yl]-4-methyl-4-hexenoate, 2-(piperidin-1-yl)ethyl (E)-6-[1,3-dihydro-4-(3,3-dimethylureido)-6-methoxy-7-methyl-3-oxoisobenzofuran-5-yl]-4-methyl-4-hexenoate, 2-(thiazolidin-3-yl)ethyl (E)-6-[1,3-dihydro-4-(3,3-dimethylureido)-6-methoxy-7-methyl-3-oxoisobenzofuran-5-yl]-4-methyl-4-hexenoate, 3-(morpholin-4-yl)propyl (E)-6-[1,3-dihydro-4-(3,3-dimethylureido)-6-methoxy-7-methyl-3-oxoisobenzofuran-5-yl]-4-methyl-4-hexenoate, 4-(morpholin-4-yl)butyl (E)-6-[1,3-dihydro-4-(3,3-dimethylureido)-6-methoxy-7-methyl-3-oxoisobenzofuran-5-yl]-4-methyl-4-hexenoate, 2-(imidazolidin-1-yl)ethyl (E)-6-[1,3-dihydro-4-(3,3-dimethylureido)-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3,3-dimethylureido)-6-methoxy-7-methyl-3-oxoisobenzofuran-5-yl]-4-methyl-4-hexenoate, 2-(pyrrolidin-1-yl)ethyl (E)-6-[1,3-dihydro-4-(3-methyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3-methyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3-methyl)ureido-6-methoxy-7-methyl-3-oxoisobenzofuran-5-yl]-4-methyl-4-hexenoate, 3-(morpholin-4-yl)propyl (E)-6-[1,3-dihydro-4-(3-methyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3-methyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3-methyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3-methyl)ureido-6-methoxy-7-methyl-3-oxoisobenzofuran-5-yl]-4-methyl-4-hexenoate, 2-(pyrrolidin-1-yl)ethyl (E)-6-(1,3-dihydro-4-ureido-6-methoxy-7-methyl-3-oxoisobenzofuran-5-yl)-4-methyl-4-hexenoate, 2-(piperidin-1-yl)ethyl (E)-6-(1,3-dihydro-4-ureido-6-methoxy-7-methyl-3-oxoisobenzofuran-5-yl)-4-methyl-4-hexenoate, 2-(thiazolidin-3-yl)ethyl (E)-6-(1,3-dihydro-4-ureido-6-methoxy-7-methyl-3-oxoisobenzofuran-5-yl)-4-methyl-4-hexenoate, 3-(morpholin-4-yl)propyl (E)-6-(1,3-dihydro-4-ureido-6-methoxy-7-methyl-3-oxoisobenzofuran-5-yl)-4-methyl-4-hexenoate, 4-(morpholin-4-yl)butyl (E)-6-(1,3-dihydro-4-ureido-6-methoxy-7-methyl-3-oxoisobenzofuran-5-yl)-4-methyl-4-hexenoate, 2-(imidazolidin-1-yl)ethyl (E)-6-(1,3-dihydro-4-ureido-6-methoxy-7-methyl-3-oxoisobenzofuran-5-yl)-4-methyl-4-hexenoate, 2-(2-methyl-1,2-pyrazolidin-1-yl)ethyl (E)-6-(1,3-dihydro-4-ureido-6-methoxy-7-methyl-3-oxoisobenzofuran-5-yl)-4-methyl-4-hexenoate, 2-(pyrrolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3,3-diethyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3,3-diethyl)ureido-6-methoxy-7-methyl-3-oxoisobenzofuran-5-yl]-4-methyl-4-hexenoate, 3-(morpholin-4-yl)propyl (E)-6-[1,3-dihydro-4-(3,3-diethyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3,3-diethyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate, 2-(pyrrolidin-1-yl)ethyl (E)-6-[1,3-dihydro-4-(3-ethyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3-ethyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3-ethyl)ureido-6-methoxy-7-methyl-3-oxoisobenzofuran-5-yl]-4-methyl-4-hexenoate, 3-(morpholin-4-yl)propyl (E)-6-[1,3-dihydro-4-(3-ethyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3-ethyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3-ethyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3-ethyl)ureido-6-methoxy-7-methyl-3-oxoisobenzofuran-5-yl]-4-methyl-4-hexenoate, 2-(pyrrolidin-1-yl)ethyl (E)-6-[13-dihydro-4-(3-methyl-3-ethyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3-methyl-3-ethyl)ureido-6-methoxy-7-methyl-3-oxoisobenzofuran-5-yl]-4-methyl-4-hexenoate, 3-(morpholin-4-yl)propyl (E)-6-[13-dihydro-4-(3-methyl-3-ethyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3-methyl-3-ethyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate, 2-(pyrrolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3,3-diphenyl)ureido-6-methoxy-7-methyl-3-oxoisobenzofuran-5-yl]-4-methyl-4-hexenoate, 3-(morpholin-4-yl)propyl (E)-6-[1,3-dihydro-4-(3,3-diphenyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3,3-diphenyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate, 2-(pyrrolidin-1-yl)ethyl (E)-6-[1,3-dihydro-4-(3-phenyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3-phenyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3-phenyl)ureido-6-methoxy-7-methyl-3-oxoisobenzofuran-5-yl]-4-methyl-4-hexenoate, 3-(morpholin-4-yl)propyl (E)-6-[1,3-dihydro-4-(3-phenyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3-phenyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3-phenyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3-phenyl)ureido-6-methoxy-7-methyl-3-oxoisobenzofuran-5-yl]-4-methyl-4-hexenoate, 2-(pyrrolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3-methyl-3-phenyl)ureido-6-methoxy-7-methyl-3-oxoisobenzofuran-5-yl]-4-methyl-4-hexenoate, 3-(morpholin-4-yl) propyl (E)-6-[1,3-dihydro-4-(3-methyl-3-phenyl)ureido-6-methoxy-7-methyl-3-oxoisobenzofuran-5-yl]-4-methyl-4-hexenoate, 4-(morpholin-4-yl)butyl (E)-6-[1,3-dihydro-4-(3-methyl-3-phenyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate, 2-(pyrrolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate, 2-(piperidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate, 2-(thiazolidin-3-yl)ethyl (E)-6-[1,3-dihydro-4-(3-butyl-3-propyl)ureido-6-methoxy-7-methyl-3-oxoisobenzofuran-5-yl]-4-methyl-4-hexenoate, 3-(morpholin-4-yl) propyl (E)-6-[1,3-dihydro-4-(3-butyl-3-propyl)ureido-6-methoxy-7-methyl-3oxoisobenzofuran-5-yl]-4-methyl-4-hexenoate, 4-(morpholin-4-yl)butyl (E)-6-[1,3-dihydro-4-(3-butyl-3-propyl)ureido-6-methoxy-7-methyl-3-oxoisobenzofuran-5-yl]-4-methyl-4-hexenoate, 2-(imidazolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate, 2-(2-methyl-1,2-pyrazolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate, 2-(pyrrolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate, 2-(piperidin-1-yl)ethyl (E)-6-[1,3-dihydro-4-3-(2-chlorophenyl)ureido)-6-methoxy-7-methyl-3-oxoisobenzofuran-5-yl]-4-methyl-4-hexenoate, 2-(thiazolidin-3-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate, 3-(morpholin-4-yl)propyl (E)-6-[1,3-dihydro-4-(3-(2-chlorophenyl)ureido)-6-methoxy-7-methyl-3-oxoisobenzofuran-5-yl]-4-methyl-4-hexenoate, 4-(morpholin-4-yl)butyl (E)-6-[1,3-dihydro-4-(3-(2-chlorophenyl)ureido)-6-methoxy-7-methyl-3-oxoisobenzofuran-5-yl]-4-methyl-4-hexenoate, 2-(imidazolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate; and methyl E-6-[1,3-dihydro-4-(trifluoroacetyl)amino-6-methoxy-7-methyl-3-oxoisobenzofuran-5-yl]-4-methyl-4-hexenoate, methyl (E)-6-[1,3-dihydro-4-(difluoroacetyl)amino-6-methoxy-7-methyl-3-oxoisobenzofuran-5-yl]-4-methyl-4-hexenoate, methyl (E)-6-[1,3-dihydro-4-(fluoroacetyl)amino-6-methoxy-7-methyl-3-oxoisobenzofuran-5-yl]-4-methyl-4-hexenoate, methyl (E)-6-[1,3-dihydro-4-(trichloroacetyl)amino-6-methoxy-7-methyl-3-oxoisobenzofuran-5-yl]-4-methyl-4-hexenoate; and methyl (E)-6-[1,3-dihydro-4-(fluorodichloroacetyl)-amino-6-methoxy-7-methyl-3-oxo isobenzofuran-5-yl]-4-methyl-4-hexenoate. (E)-6-[1,3-dihydro-4-(difluoroacetyl)amino-6-methoxy-7-methyl-3-oxoisobenzofuran-5-yl]-4-methyl-4-hexenoic acid, (E)-6-[1,3-dihydro-4-(fluoroacetyl)amino-6-methoxy-7-methyl-3-oxoisobenzofuran-5-yl]-4-methyl-4-hexenoic acid, (E)-6-[1,3-dihydro-4-(trichloroacetyl)amino-6-methoxy-7-methyl-3-oxoisobenzofuran-5-yl]-4-methyl-4-hexenoic acid, (E)-6-[1,3-dihydro-4-(fluorodichloroacetyl)amino-6-methoxy-7-methyl-3-oxoisobenzofuran-5-yl]-4-methyl-4-hexenoic acid. 2-(2-methyl-1,2-pyrazolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate. (E)-6-[1,3-dihydro-4-(trifluoroacetyl) amino-6-methoxy-7-methyl-3-oxoisobenzofuran-5-yl]-4-methyl-4-hexenoic acid, (E)-6-[1,3-dihydro-4-acetamido-6-methoxy-7-methyl-3-oxoisobenzofuran-5-yl]-4-methyl-4-hexenoic acid, methyl (E)-6-[1,3-dihydro-4-(difluoroacetyl)amino-6-methoxy-7-methyl-3-oxoisobenzofuran-5-yl]-4-methyl-4-hexenoate, methyl (E)-6-[1,3-dihydro-4-(fluoroacetyl)amino-6-methoxy-7-methyl-3-oxoisobenzofuran-5-yl]-4-methyl-4-hexenoate, methyl (E)-6-[1,3-dihydro-4-(trichloroacetyl)amino-6-methoxy-7-methyl-3-oxoisobenzofuran-5-yl]-4-methyl-4-hexenoate, methyl (E)-6-[1,3-dihydro-4-(fluorodichloroacetyl)amino-6-methoxy-7-methyl-3-oxoisobenzofuran-5-yl]-4-methyl-4-hexenoate, ethyl (E)-6-(1,3-dihydro-4-methylamino-6-methoxy-7-methyl-3-oxoisobenzofuran-5-yl)-4-methyl-4-hexenoate, n-propyl (E)-6-(1,3-dihydro-4-methylamino-6-methoxy-7-methyl-3-oxoisobenzofuran-5-yl)-4-methyl-4-hexenoate, isopropyl (E)-6-(1,3-dihydro-4-methylamino-6-methoxy-7-methyl-3-oxoisobenzofuran-5-yl)-4-methyl-4-hexenoate, t-butyl (E)-6-(1,3-dihydro-4-methylamino-6-methoxy-7-methyl-3-oxoisobenzofuran-5-yl)-4-methyl-4-hexenoate, 2-trifluoromethylphenyl (E)-6-(1,3-dihydro-4-methylamino-6-methoxy-7-methyl-3-oxoisobenzofuran-5-yl)-4-methyl-4-hexenoate, 2-chloro-3,4-dimethoxyphenyl (E)-6-(1,3-dihydro-4-methylamino-6-methoxy-7-methyl-3-oxoisobenzofuran-5-yl)-4-methyl-4-hexenoate, and ethyl (E)-6-(1,3-dihydro-4-ethylamino-6-methoxy-7-methyl-3-oxoisobenzofuran-5-yl)-4-methyl-4-hexenoate; formula I in U.S. Pat. No. 5,441,953, e.g., E)-6-(1,3-dihydro-4-amino-6-methoxy-7-methyl-3-oxoisobenzofuran-5-yl)-4-methyl-4-hexenoic acid and E-6-(1,3-dihydro-4-(trifluoroacetyl)amino-6-methoxy-7-methyl-3-oxoisobenzofuran-5-yl)-4-hexenoic acid; formula I in U.S. Pat. No. 5,444,072, e.g., E) 6-(1,3-dihydro-4-hydroxy-6,7-dimethyl-3-oxoisobenzofuran-5-yl)-4-methyl-4-hexenoic acid, (E) 6-(1,3-dihydro-6-ethyl-4-hydroxy-7-methyl-3-oxoisobenzofuran-5-yl)-4-methyl-4-hexenoic acid, (E) 6-(6-cyclopropyl-1,3-dihydro-4- hydroxy-7-methyl-3oxoisobenzofuran-5-yl)-4-methyl-4-hexenoic acid, (E) 6-(1,3-dihydro-4-hydroxy-7-methyl-3-oxo-6-vinylisobenzofuran-5-yl)-4-methyl-4-hexenoic acid, (E) 6-(1,3-dihydro-6-ethyl-4-hydroxy-7-methyl-3-oxoisobenzofuran-5-yl)-3,4-dimethyl-4-hexenoic acid, and (E)-2-[2-[2-[1,3-dihydro-6-ethyl 4-hydroxy-7-methyl-3-oxoisobenzofuran-5-yl]ethylidene]cyclopent-1-yl]acetic acid; by formula I in U.S. Pat. No. 5,493,030, e.g., (+) (E) 6-(1,3-dihydro-4-hydroxy-6-methoxy-7-methyl-3-oxoisobenzofuran-5-yl)-3,4-dimethyl-4-hexenoic acid, (E) 6-(1,3-dihydro-4-hydroxy-6-methoxy-7-methyl-3-oxoisobenzofuran-5-yl)-2-(S),4-dimethyl-4-hexenoic acid, (+) (E) 6-(1,3-dihydro-4-hydroxy-6-methoxy-7-methyl-3-oxoisobenzofuran-5-yl)-2,3,4-trimethyl-4-hexenoic acid, (E) 6-(1,3-dihydro-4-hydroxy-6-methoxy-7-methyl-3-oxoisobenzofuran-5-yl)-2-(S)-ethyl-4-methyl-4-hexenoic acid, 2-{2-[2-(1,3-dihydro-4-hydroxy-6-methoxy-7-methyl-3-oxoisobenzofuran-5-yl)ethylidene]cyclohex-1-(S)-yl}acetic acid, 2-{2-[2-[1,3-dihydro-4-hydroxy-6-methoxy-7-methyl-3-oxoisobenzofuran-5-yl]ethylidene]cyclopent-1-(S)-yl}acetic acid, 2-{2-[2-(4-hydroxy-1,3-dihydro-6-methoxy-7-methyl-3-oxoisobenzofuran-5-yl)ethylidene]cyclohex-1-(S)-yl}-2-(S)-methylacetic acid, 2-{2-[2-[1,3-dihydro-4-hydroxy-6-methoxy-7-methyl-3-oxoisobenzofuran-5-yl]ethylidene]cyclopent-1-(S)-yl}-2-(S)-ethylacetic acid, (–)-2-{2-[2o[1,3-dihydro-4-hydroxy-6-methoxy-7-methyl-3-oxoisobenzofuran-5-yl]ethylidene]cyclopent-1-(S)-yl}-2-methylacetic acid, including the 2-(R)-methylacetic acid and 2-(S)-methylacetic acid isomers, (–)-2-{4-[2-[1,3-dihydro-4-hydroxy-6-methoxy-7-methyl-3-oxoisobenzofuran-5-yl]ethylidene]tetrahydropyran-3-yl}acetic acid, (E) 2-[3-(1,3-dihydro-4-hydroxy-6-methoxy-7-methyl-3-oxoisobenzofuran-5-yl)-1-methylprop-1-en-1-yl]tetrahydropyran-1-carboxylic acid, (E) 2-(S)-{4-[2-(1,3-dihydro-4-hydroxy-6-methoxy-7-methyl-3-oxoisobenzofuran-5-yl)ethylidene]-tetrahydropyran-3-(S)-yl}propionic acid, (E) 2-[3-(1,3-dihydro-4-hydroxy-6-methoxy-7-methyl-3-oxoisobenzofuran-5-yl)-1-methylprop-1-en-1-yl]cyclopentane-1-carboxylic acid, and (E) 2-[3-(1,3-dihydro-4-hydroxy-6-methoxy-7-methyl-3-oxoisobenzofuran-5-yl)-1-methylprop-1-en-1-yl]cyclohexane-1-carboxylic acid, most particularly: (E) 6-(1,3-dihydro-4-hydroxy-6-methoxy-7-methyl-3-oxoisobenzofuran-5-yl)-2-(S),4-dimethyl-4-hexenoic acid, (+) (E) 6-(1,3-dihydro-4-hydroxy-6-methoxy-7-methyl-3 oxoisobenzofuran-5-yl)-2,3,4-trimethyl-4-hexenoic acid (having a melting point of 146.degree.-148.degree. C. when recrystallized from hexane/methylene chloride), (E) 2-(S)-{4-[2-(1,3-dihydro-4-hydroxy-6-methoxy-7-methyl-3-isobenzofuran-5-yl)ethylidene]-tetrahydropyran-3-(S)-yl}propionic acid, and (–)-2-{2-[2-[1,3-dihydro-4-hydroxy-6-methoxy-7-methyl-3-oxoisobenzofuran-5-yl]ethylidene]cyclopent-1(S)-yl}-2-methylacetic acid, including the 2-(R)-methylacetic acid and 2-(S)-methylacetic acid isomers; by formula I in U.S. Pat. No. 5,538,969, e.g., (E)-6-(4-amino-1,3-dihydro-6-methoxy-7-methyl-3-oxoisobenzofuran-5-yl)-2(S),4-dimethyl-4-hexenoic acid, (E)-6-(4-amino-1,3-dihydro-6-methoxy-7-methyl-3-oxoisobenzofuran-5-yl)-3(S),4-dimethyl-4-hexenoic acid, (E)-2-[2-[2-[4-amino-1,3-dihydro-6-methoxy-7-methyl-3-oxoisobenzofuran-5-yl]ethylidene]cyclopent-1(S)-yl]acetic acid, and (E)-2-{4-[2-(4-amino-1,3-dihydro-6-methoxy-7-methyl-3-oxoisobenzofuran-5-yl)ethylidene]tetrahydropyran-3(S)-yl}acetic acid; by formula I of U.S. Pat. No. 5,554,612, e.g., (E)-6-(4-amino-1,3-dihydro-6-ethyl-7-methyl-3-oxoisobenzofuran-5-yl)-4-methyl-4-hexenoic acid, (E)-6-(4-amino-1,3-dihydro-6-ethyl-7-methyl-3-oxoisobenzofuran-5-yl)-3,4-di methyl-4-hexenoic acid, and (E)-2-{2-[2-(4-amino-1,3-dihydro-6-ethyl-7-methyl-3-oxoisobenzofuran-5-yl)-ethylidene]-cyclopent-1-yl}acetic acid; and by formula I of U.S. Pat. No. 5,633,279, e.g., (+) (E)-6-(1,3-dihydro-4-hydroxy-6-methoxy-7-methyl-3-oxoisobenzofuran-5-yl)-3,4-dimethyl-4-hexenoic acid; (E)-6-(1,3-dihydro-4-hydroxy-6-methoxy-7-methyl-3-oxoisobenzofuran-5-yl)-2(S),4-dimethyl-4-hexenoic acid, (+) (E)-6-(1,3-dihydro-4-hydroxy-6-methoxy-7-methyl-3-oxoisobenzofuran-5-yl)-2,3,4-trimethyl-4-hexenoic acid, (E)-6-(1,3-dihydro-4-hydroxy-6-methoxy-7-methyl-3-oxoisobenzofuran-5-yl)-2(S)-ethyl-4-methyl-4-hexenoic acid, 2-{2-[2-(1,3-dihydro-4-hydroxy-6-methoxy-7-methyl-3-oxoisobenzofuran-5-yl)ethylidene]cyclohex-1(S)-yl}acetic acid, 2-{2-[2-[1,3-dihydro-4-hydroxy-6-methoxy-7-methyl-3-oxoisobenzofuran-5-yl]ethylidene]cyclopent-[(S)-yl}acetic acid, 2-{2-[2-(4-hydroxy-1,3-dihydro-6-methoxy-7-methyl-3-oxoisobenzofuran-5-yl)ethylidene]cyclohex-1(S)-yl}-2(S)-methylacetic acid, 2-{2-[2-[1,3-dihydro-4-hydroxy-6-methoxy-7-methyl-3-oxoisobenzofuran-5-yl]ethylidene]cyclopent-1(S)-yl}-2(S)-ethylacetic acid, (–) 2-{2-[2-[1,3-dihydro-4-hydroxy-6-methoxy-7-methyl-3-oxoisobenzofuran-5-yl]ethylidene]cyclopent-1(S)-yl}-2-methylacetic acid, including the 2(R)-methylacetic acid and 2(S)-methylacetic acid isomers, (–) 2-{4-[2-[1,3-dihydro-4-hydroxy-6-methoxy-7-methyl-3-oxoisobenzofuran-5-yl]ethylidene]tetrahydropyran-3-yl}acetic acid, (E)-2-[3-(1,3-dihydro-4-hydroxy-6-methoxy-7-methyl-3-oxoisobenzofuran-5-yl)-1-methylprop-1-en-1-yl]tetrahydropyran-1-carboxylic acid, (E)-2(S)-{4-[2-(1,3-dihydro-4-hydroxy-6-methoxy-7-methyl-3-oxoisobenzofuran-5-yl)ethylidene]-tetrahydropyran-3(S)-yl}propionic acid, (E)-2-[3-(1,3-dihydro-4-hydroxy-6-methoxy-7-methyl-3-oxoisobenzofuran-5-yl)-1-methylprop-1-en-1-yl]cyclopentane-1-carboxyli c acid, and (E)-2-[3-(1,3-dihydro-4-hydroxy-6-methoxy-7-methyl-3-oxoisobenzofuran-5-yl)-1-methylprop-1-en-1-yl]cyclohexane-1-carboxylic acid, (E)-6-(1,3-dihydro-4-hydroxy-6-methoxy-7-methyl-3-oxoisobenzofuran-5-yl)-2(S),4-dimethyl-4-hexenoic acid, (+) (E)-6-(1,3-dihydro-4-hydroxy-6-methoxy-7-methyl-3-oxoisobenzofuran-5-yl)-2,3,4-trimethyl-4-hexenoic acid, (E)-2(S)-{4-[2-(1,3-dihydro-4-hydroxy-6-methoxy-7-methyl-3-isobenzofuran-5-yl)ethylidene]-tetrahydropyran-3(S)-yl}propionic acid, and (–) 2-[2-[2-[1,3-dihydro-4-hydroxy-6-methoxy-7-methyl-3-oxoisobenzofuran-5-yl]ethylidene]cyclopent-1(S)-yl]-2-methylacetic acid, including the 2(R)-methylacetic acid and 2(S)-methylacetic acid isomers.

Conjugates

If desired, the agents used in any of the combinations described herein may be covalently attached to one another to form a conjugate of formula I.

(A)-(L)-(B)     (I)

In formula I, (A) is a Compound A and (B) is Compound B of a pair of agents from e.g., Table 1, and L is a covalent linker that tethers (A) to (B). Conjugates of the invention can be administered to a subject by any route and for the treatment of a filovirus-mediated disease (e.g., those described herein).

The conjugates of the invention can be prodrugs, releasing drug (A) and drug (B) upon, for example, cleavage of the conjugate by intracellular and extracellular enzymes (e.g., amidases, esterases, and phosphatases). The conjugates of the invention can also be designed to largely remain intact in vivo, resisting cleavage by intracellular and extracellular enzymes. The degradation of the conjugate in vivo can be controlled by the design of linker (L) and the covalent bonds formed with drug (A) and drug (B) during the synthesis of the conjugate.

Conjugates can be prepared using techniques familiar to those skilled in the art. For example, the conjugates can be prepared using the methods disclosed in G. Hermanson, *Bioconjugate Techniques*, Academic Press, Inc., 1996. The synthesis of conjugates may involve the selective protection and deprotection of alcohols, amines, ketones, sulfhydryls or carboxyl functional groups of drug (A), the linker, and/or drug (B). For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxyl functionalities and the conditions required for their removal are provided in detail in T. W. Green and P. G. M. Wuts, *Protective Groups in Organic Synthesis* ($2^{nd}$ Ed.), John Wiley & Sons, 1991 and P. J. Kocienski, *Protecting Groups*, Georg Thieme Verlag, 1994. Additional synthetic details are provided below.

Linkers

The linker component of the invention is, at its simplest, a bond between drug (A) and drug (B), but typically provides a linear, cyclic, or branched molecular skeleton having pendant groups covalently linking drug (A) to drug (B).

Thus, linking of drug (A) to drug (B) is achieved by covalent means, involving bond formation with one or more functional groups located on drug (A) and drug (B). Examples of chemically reactive functional groups which may be employed for this purpose include, without limitation, amino, hydroxyl, sulfhydryl, carboxyl, carbonyl, carbohydrate groups, vicinal diols, thioethers, 2-aminoalcohols, 2-aminothiols, guanidinyl, imidazolyl, and phenolic groups.

The covalent linking of drug (A) and drug (B) may be effected using a linker that contains reactive moieties capable of reaction with such functional groups present in drug (A) and drug (B). For example, an amine group of drug (A) may react with a carboxyl group of the linker, or an activated derivative thereof, resulting in the formation of an amide linking the two.

Examples of moieties capable of reaction with sulfhydryl groups include α-haloacetyl compounds of the type $XCH_2CO$— (where X=Br, Cl, or I), which show particular reactivity for sulfhydryl groups, but which can also be used to modify imidazolyl, thioether, phenol, and amino groups as described by Gurd, *Methods Enzymol.* 11:532 (1967). N-Maleimide derivatives are also considered selective towards sulfhydryl groups, but may additionally be useful in coupling to amino groups under certain conditions. Reagents such as 2-iminothiolane (Traut et al., *Biochemistry* 12:3266 (1973)), which introduce a thiol group through conversion of an amino group, may be considered as sulfhydryl reagents if linking occurs through the formation of disulfide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type $XCH_2CO$— (where X=Br, Cl, or I), for example, as described by Wong *Biochemistry* 24:5337 (1979);

(ii) N-maleimide derivatives, which may react with amino groups either through a Michael type reaction or through acylation by addition to the ring carbonyl group, for example, as described by Smyth et al., *J. Am. Chem. Soc.* 82:4600 (1960) and *Biochem. J.* 91:589 (1964);

(iii) aryl halides such as reactive nitrohaloaromatic compounds;

(iv) alkyl halides, as described, for example, by McKenzie et al., *J. Protein Chem.* 7:581 (1988);

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sufhydryl, and hydroxyl groups;

(viii) aziridines based on s-triazine compounds detailed above, e.g., as described by Ross, *J. Adv. Cancer Res.* 2:1 (1954), which react with nucleophiles such as amino groups by ring opening;

(ix) squaric acid diethyl esters as described by Tietze, *Chem. Ber.* 124:1215 (1991); and (x) α-haloalkyl ethers, which are more reactive alkylating agents than normal alkyl halides because of the activation caused by the ether oxygen atom, as described by Benneche et al., *Eur. J. Med. Chem.* 28:463 (1993).

Representative amino-reactive acylating agents include:

(i) isocyanates and isothiocyanates, particularly aromatic derivatives, which form stable urea and thiourea derivatives respectively;

(ii) sulfonyl chlorides, which have been described by Herzig et al., *Biopolymers* 2:349 (1964);

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation, for example, as described by M. Bodansky, *Principles of Peptide Synthesis*, Springer-Verlag, 1984;

(vii) acylazides, e.g., wherein the azide group is generated from a preformed hydrazide derivative using sodium nitrite, as described by Wetz et al., *Anal. Biochem.* 58:347 (1974); and (viii) imidoesters, which form stable amidines on reaction with amino groups, for example, as described by Hunter and Ludwig, *J. Am. Chem. Soc.* 84:3491 (1962).

Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96 (1990).

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169 (1947). Carboxyl modifying reagents such as carbodiimides, which react through O-acylurea formation followed by amide bond formation, may also be employed.

It will be appreciated that functional groups in drug (A) and/or drug (B) may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of drug (A) with a reactive chemical group of drug (B) without introducing additional linking material may, if desired, be used in accordance with the invention.

More commonly, however, the linker will include two or more reactive moieties, as described above, connected by a spacer element. The presence of such a spacer permits bifunctional linkers to react with specific functional groups within drug (A) and drug (B), resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between drug (A) and drug (B).

Spacer elements in the linker typically consist of linear or branched chains and may include a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl.

In some instances, the linker is described by formula (II):

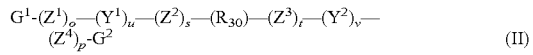

(II)

In formula (II), $G^1$ is a bond between drug (A) and the linker; $G^2$ is a bond between the linker and drug (B); $Z^1$, $Z^2$, $Z^3$, and $Z^4$ each, independently, is selected from O, S, and $NR_{31}$; $R_{31}$ is hydrogen, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl; $Y^1$ and $Y^2$ are each, independently, selected from carbonyl, thiocarbonyl, sulphonyl, or phosphoryl; o, p, s, t, u, and v are each, independently, 0 or 1; and $R_{30}$ is a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, or $C_{1-10}$ heteroalkyl, or a chemical bond linking $G^1$-$(Z^1)_o$—$(Y^1)_u$—$(Z^2)_s$— to —$(Z^3)_t$—$(Y^2)_v$—$(Z^4)_p$-$G^2$.

Examples of homobifunctional linkers useful in the preparation of conjugates of the invention include, without limitation, diamines and diols selected from methylenediamine, propylenediamine and hexamethylenediamine, ethylene glycol, diethylene glycol, propylene glycol, 1,4-butanediol, 1,6-hexanediol, cyclohexanediol, and polycaprolactone diol.

Formulation of Pharmaceutical Compositions

The compositions, methods, and kits of the invention can include formulation(s) of compound(s) that, upon administration to a subject, result in a concentration of the compound(s) that treats a filovirus-mediated disease. The compound(s) may be contained in any appropriate amount in any suitable carrier substance, and are generally present in an amount of 1-95% by weight of the total weight of the composition. The composition may be provided in a dosage form that is suitable for the oral, parenteral (e.g., intravenously or intramuscularly), rectal, dermatological, cutaneous, nasal, vaginal, inhalant, skin (patch), ocular, intrathecal, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions according to the invention or used in the methods of the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the combination to a particular target cell type. Administration of compound(s) in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound(s) are formulated with appropriate excipients into a pharmaceutical composition that, upon administration, releases the compound(s) in a controlled manner. Examples include single or multiple unit tablet or capsule compositions, oil solutions, suspensions, emulsions, microcapsules, molecular complexes, microspheres, nanoparticles, patches, and liposomes.

Delivery of Compound(s)

It is not intended that administration of compounds be limited to a single formulation and delivery method for all compounds of a combination. The combination can be administered using separate formulations and/or delivery methods for each compound of the combination using, for example, any of the above-described formulations and methods. In one example, a first agent is delivered orally, and a second agent is delivered intravenously.

Dosages

The dosage of a compound or a combination of compounds depends on several factors, including: the administration method, the type of disease to be treated, the severity of the infection, whether administration first occurs at an early or late stage of infection, and the age, weight, and health of the patient to be treated.

For combinations that include a synergistic pair of agents identified herein (e.g., a pair of Table 4), the recommended dosage for the anti-viral agent can be less than or equal to the recommended dose as given in the *Physician's Desk Reference*, 60$^{th}$ Edition (2006).

As described above, the compound(s) in question may be administered orally in the form of tablets, capsules, elixirs or syrups, or rectally in the form of suppositories. Parenteral administration of a compound is suitably performed, for example, in the form of saline solutions or with the compound(s) incorporated into liposomes. In cases where the compound in itself is not sufficiently soluble to be dissolved, a solubilizer such as ethanol can be applied. The correct dosage of a compound can be determined by examining the efficacy of the compound in viral replication assays, as well as its toxicity in humans.

An antiviral agent is usually given by the same route of administration that is known to be effective for delivering it as a monotherapy. When used in combination therapy according to the methods of this invention, an agent of Table 2 or Table 3 is dosed in amounts and frequencies equivalent to or less than those that result in its effective monotherapeutic use.

Additional Applications

If desired, the compounds of the invention may be employed in mechanistic assays to determine whether other combinations, or single agents, are as effective as the combinations of the invention in inhibiting a viral disease (e.g., those described herein) using assays generally known in the art. For example, candidate compounds may be tested, alone or in combination (e.g., with an agent that inhibits viral replication, such as those described herein) and applied to cells (e.g., hepatic cells such as HepG2, kidney epithelial cells such as 293T, macrophages such as THP-1, or isolated primary cells). After a suitable time, viral replication or load of these cells is examined. A decrease in viral replication or viral load identifies a candidate compound or combination of agents as an effective agent for treating a viral disease.

The agents of the invention are also useful tools in elucidating mechanistic information about the biological pathways involved in viral diseases. Such information can lead to the development of new combinations or single agents for treating, preventing, or reducing a viral disease. Methods known in the art to determine biological pathways can be used to determine the pathway, or network of pathways affected by contacting cells (e.g., hepatic cells) infected with a virus with the compounds of the invention. Such methods can include, analyzing cellular constituents that are expressed or repressed after contact with the compounds of the invention as compared to untreated, positive or negative control compounds, and/or new single agents and combinations, or analyzing some other activity of the cell or virus such as an enzymatic activity, nutrient uptake, and proliferation. Cellular components analyzed can include gene transcripts, and protein expression. Suitable methods can include standard biochemistry techniques, radiolabeling the compounds of the invention (e.g., $^{14}$C or $^{3}$H labeling), and observing the compounds binding to proteins, e.g., using 2D gels, gene expression profiling. Once identified, such compounds can be used in in vivo models (e.g., knockout or transgenic mice) to further validate the tool or develop new agents or strategies to treat viral disease.

Exemplary Candidate Compounds

Peptide Moieties

Peptides, peptide mimetics, and peptide fragments (whether natural, synthetic or chemically modified) are suitable for use in the methods of the invention. Exemplary inhibitors include compounds that reduce the amount of a target protein or RNA levels (e.g., antisense compounds, dsRNA, ribozymes) and compounds that compete with viral reproduction machinery (e.g., dominant negative proteins or polynucleotides encoding the same).

Antisense Compounds

The biological activity of any protein that increases viral replication, viral RNA or DNA replication, viral RNA translation, viral protein processing or activity, or viral packaging can be reduced through the use of an antisense compound directed to RNA encoding the target protein. Antisense compounds can be identified using standard techniques. For example, accessible regions of the target the mRNA of the target enzyme can be predicted using an RNA secondary structure folding program such as MFOLD (M. Zuker, D. H. Mathews & D. H. Turner, *Algorithms and Thermodynamics for RNA Secondary Structure Prediction: A Practical Guide. In: RNA Biochemistry and Biotechnology*, J. Barciszewski & B. F. C. Clark, eds., NATO ASI Series, Kluwer Academic Publishers, (1999)). Sub-optimal folds with a free energy value within 5% of the predicted most stable fold of the mRNA are predicted using a window of 200 bases within which a residue can find a complimentary base to form a base pair bond. Open regions that do not form a base pair are summed together with each suboptimal fold and areas that are predicted as open are considered more accessible to the binding to antisense nucleobase oligomers. Other methods for antisense design are described, for example, in U.S. Pat. No. 6,472,521, *Antisense Nucleic Acid Drug Dev.* 7:439-444 (1997), *Nucleic Acids Res.* 28:2597-2604 (2000), and *Nucleic Acids Res.* 31:4989-4994 (2003).

RNA Interference

The biological activity of a molecule involved in a viral infection or viral replication can be reduced through the use of RNA interference (RNAi), employing, e.g., a double stranded RNA (dsRNA) or small interfering RNA (siRNA) directed to the signaling molecule in question (see, e.g., Miyamoto et al., *Prog. Cell Cycle Res.* 5:349-360 (2003); U.S. Pat. Application Publication No. 20030157030). Methods for designing such interfering RNAs are known in the art. For example, software for designing interfering RNA is available from Oligoengine (Seattle, Wash.).

Dominant Negative Proteins

One skilled in the art would know how to make dominant negative proteins to the molecules involved in a viral infection or viral replication. Such dominant negative proteins are described, for example, in Gupta et al., *J. Exp. Med.*, 186:473-478 (1997); Maegawa et al., *J. Biol. Chem.* 274:30236-30243 (1999); and Woodford-Thomas et al., *J. Cell Biol.* 117:401-414 (1992).

EXAMPLES

The following examples are intended to illustrate rather than limit the invention.

Example 1

Identification of Single Therapeutic Agents using a Genetically Engineered Fully Infectious Ebola Virus A genetically engineered Ebolavirus (EBOV) expressing the green fluorescent protein (GFP) has been used to develop a high throughput assay for drug discovery (Towner et al., Virology, 332: 20 (2005)). The genetically engineered virus has the unique property of making infected cells glow fluorescent green. The green signal can be detected by fluorescence microscopy, flow cytometry, or fluorometry, and other types of fluorescence detection systems adapted for high-throughput format. In order to perform the assay, seed Vero or HepG2 cells on a 96-well plate at 40,000 cells/well in a total volume of 100 μL/well. The plated cells are incubated cells at 37° C., 5% $CO_2$ until they achieve a stationary growth phase. Next 50 μl of pre-diluted compounds are added at a 4× concentration to each well to achieve the desired final concentration. Finally, 50 μl of GFP-EBOV (multiplicity of infection of 0.01) is added to cells. Plates are centrifuged at 2000 RPM, 5 minutes following the addition of EBOV. Cells are incubated an additional 48 hours at 37° C., 5% $CO_2$, and the plates are then removed from the incubator and the amount of GPF in each well is determined using a spectrofluorometer from Molecular Devices (excitation: 485 nm, emission: 515 nm, cutoff: 495 nm). Antiviral activity is identified by the inhibition of GFP compared to untreated control cells.

To confirm that a decrease in GFP activity correlates with inhibition of Ebola replication and not an increase in cell death, a counter screen is run in tandem using uninfected Vero or HepG2 cells. Seed cells on a 96-well plate as described above. Cells are mock infected and treated with compounds the following day. After a 48 hour incubation at 37° C., 5% $CO_2$, the amount of ATP is determined using Promega Cell Titer-Glo luminescent Cell viability kit. This assay provides a quantitative measure of the levels of ATP in the cell cultures in each well, where higher levels of ATP correlate with greater cellular viability. Thus, a compound with antiviral activity is expected to inhibit the levels of GPF measured without any or minimal effect on the ATP levels measured by the Cell Titer-Glo assay.

The assay described above was used to identify agents that inhibit the replication of Ebola virus in Vero cells. Agents thus identified (IC50) are listed in Table 6. The extent of inhibition is represented as maximum fraction inhibition (Max Effect), where a value of 1.0 is indicative of complete inhibition, and 0 is indicative of no effect. As available, 50% inhibitory concentrations of the agents are provided.

TABLE 6

| Agent | Max Effect | IC50 (μM) | Previously described activity |
| --- | --- | --- | --- |
| Cetrimide | 0.692 | 5.6 | Antibiotic |
| Pentamidine | 0.422 | 10.5 | Antiparasitic |
| Hexachlorophene | 0.713 | 3.2 | Bacterial dihydrolipoamide dehydrogenase inhibitor |
| Emetine dihydrochloride hydrate | 0.893 | 0.3 | Bacteria ribosome binder |
| Puromycin dihydrochloride | 0.835 | 6.6 | Bacteria ribosome binder |
| Thiostrepton | 0.454 | | Bacteria ribosome binder |
| Gramicidin | 0.678 | 1.7 | Bacterial membrane disrupter |
| Chlorhexidine Diacetate | 0.543 | 6.1 | Bacterial wall disrupter |
| Teicoplanin | 0.930 | 5.6 | Bacterial penicillin binding protein inhibitor |
| Cephapirin Sodium | 0.662 | 9.8 | Bacterial penicillin binding protein inhibitor |
| Pyrithione Zinc | 0.767 | 2.4 | Antifungal |
| Haloprogin | 0.588 | 2.9 | Antifungal |
| Ciclopirox Olamine | 0.431 | | Fungal Na—K channel blocker |
| Hycanthone | 0.597 | 10.4 | Antiparasitic, anthelmintic |
| Niclosamide | 0.842 | 2.6 | Antiparasitic, inhibits parasite metabolism |
| Efavirenz | 0.516 | 7.8 | HIV non-nucleoside reverse transcriptase inhibitor |
| Ritonavir | 0.485 | | HIV protease inhibitor |
| Chromomycin A3 | 0.629 | 0.4 | DNA damaging agent, DNA minor groove binder |
| Azacitidine | 0.595 | 5.0 | DNA methyltransferase inhibitor |
| (−)-Arctigenin | 0.411 | | DNA_function, topoisomerase 2 inhibitor |
| Danazol | 0.546 | 12.9 | Androgen receptor antagonist |
| Bicalutamide | 0.464 | | Androgen receptor antagonist |
| Hydroxyprogesterone Caproate | 0.719 | 3.7 | Estrogen receptor antagonist |
| Equilin | 0.424 | | Estrogen receptor antagonist |
| Clomiphene Citrate | 0.912 | 3.0 | Estrogen receptor antagonist, antifungal squalene epoxidase inhibitor |
| Quinestrol | 0.549 | 7.2 | Estrogen receptor 1 agonist |
| Tamoxifen | 0.900 | 2.3 | Estrogen receptor 1 agonist |
| Raloxifene Hydrochloride | 0.691 | 2.4 | Estrogen receptor 1 agonist |
| Tamoxifen Citrate | 0.900 | 1.7 | Estrogen receptor 1 agonist |
| Toremifene Citrate | 0.900 | >1 | Estrogen receptor 1 inhibitor |
| Toremifene | 0.461 | 2.7 | Estrogen receptor 1 inhibitor |
| Diethylstilbestrol | 0.436 | | Estrogen receptor 1 inhibitor |
| Tibolone | 1.119 | 1.2 | Nuclear GC glucocorticoid receptor activator |
| Lomerizine Dihydrochloride | 0.665 | 10.1 | Ca channel blocker |
| Maduramicin NH4 | 0.452 | | Ca ionophore |
| Bepridil Hydrochloride Monohydrate | 0.720 | 3.1 | Ca-A1A channel blocker |

TABLE 6-continued

| Agent | Max Effect | IC50 (μM) | Previously described activity |
|---|---|---|---|
| Loperamide | 0.716 | 5.5 | Ca-A1A channel blocker |
| Loperamide Hydrochloride | 0.418 | | Ca-A1A channel blocker |
| K-Strophanthin | 0.900 | <0.5 | H channel blocker |
| Carbonyl cyanide 4-(trifluoromethoxy)phenylhydrazone | 0.752 | 4.5 | Ion_transport, H ionophore |
| Beta Escin | 0.878 | 6.3 | Ion_transport, Na channel modulator |
| Auranofin | 0.020 | <1 | Gold compound |
| Calcimycin A23187 | 0.789 | 1.1 | Ions, Cation Ionophore |
| Edetate Calcium Disodium | 0.841 | 6.6 | Ions, Ca chelator |
| Octyl Gallate | 0.439 | | Ions, Ga |
| Magnesium Sulfate | 0.719 | 9.2 | Ions, Mg |
| Rescinnamine | 0.512 | | Angiotensin-Converting Enzyme inhibitor |
| Cilastatin Sodium | 0.912 | 8.8 | Dipeptidase 1 inhibitor |
| Bromelain | 0.769 | 4.0 | Prostaglandin E2 antagonist |
| Quinacrine Dihydrochloride | 0.779 | 9.5 | Phospholipase A2 receptor inhibitor |
| PGG (1,2,3,4,6-b-O-Pentagalloyl glucose) | 0.487 | 3.2 | Metabolism, unknown herbal |
| L-Asparagine | 0.771 | 7.2 | Metabolism, amino acid |
| Chondroitin Sulfate | 0.535 | 11.4 | Sietary supplement |
| Atovaquone | 0.900 | <1 | Dihydroorotate dehydrogenase inhibitor |
| Mycophenolate Mofetil | 0.900 | <1 | Inosine monophosphate dehydrogenase inhibitor |
| Mycophenolic Acid | 0.800 | <1 | Inosine monophosphate dehydrogenase inhibitor |
| Flucytosine | 0.793 | 4.4 | Thymidylate synthase inhibitor |
| 6-Azauridine | 0.800 | <1 | Pyrimidine biowynthesis inhibitor |
| Bafilomycin A1 | 0.880 | 0.019 | Vacuolar-type H+ pump or ATPase inhibitor |
| 2-Methoxy-antimycin A3 | 0.791 | 1.2 | Mitochondrial ATP synthase B chain inhibitor, cytochrome B inhibitor |
| Oligomycin | 0.426 | | Mitochondrial ATP synthase B chain inhibitor |
| Antimycin A | 0.850 | <0.04 | Mitochondrial ATP synthase B chain inhibitor, cytochrome b inhibitor |
| Rotenone | 0.700 | <2 | Mitochondrial ATP synthase B inhibitor; Tubulin destablizer |
| FR122047 | 0.688 | 3.7 | Cyclooxygenase-1 inhibitor |
| Fenoprofen Calcium | 0.454 | | Cyclooxygenase 1 and 2 inhibtor |
| Perhexiline Maleate | 0.890 | 4.1 | Carnitine palmitoyltransferase 1A/Carnitine palmitoyltransferase 2 inhibitor |
| PDMP Hydrochloride | 0.390 | | UDP-glucose ceramide glucosyltransferase inhibitor |
| Licochalcone-A | 0.522 | 4.7 | Metabolism, antioxidant |
| Tiratricol | 0.478 | | Metabolism, antioxidant |
| CAPE | 0.368 | | Metabolism, antioxidant |
| Amlodipine Besylate | 0.528 | 13.2 | Redox metabolism, Carbonic anhydrase I inhibitor; Ca channel blocker |
| Diphenyleneiodonium chloride | 0.800 | <1.6 | Redox metabolism, iNOS inhibitor |
| Terconazole | 0.785 | 7.7 | Sterol metabolism, fungal ERG11/CYP51 inhibitor |
| Sulconazole Nitrate | 0.904 | 4.1 | Sterol metabolism, fungal ERG11/CYP51 inhibitor inhib |
| Tioconazole | 0.729 | 8.5 | Sterol metabolism, fungal ERG11/CYP51 inhibitor |
| Oxiconazole Nitrate | 0.411 | | Fungal ERG11/CYP51 inhib |
| Simvastatin | 0.690 | 2.0 | HMG-CoA reductase (or 3-hydroxy-3-methyl-glutaryl-CoA reductase/fung HMG2 inhib |
| Cerivastatin Sodium | 0.443 | 0.1 | HMG-CoA reductase (or 3-hydroxy-3-methyl-glutaryl-CoA reductase/fung HMG2 inhib |
| Metergoline | 0.577 | 6.1 | Serotonin receptor inhibitor |
| Thioridazine Hydrochloride | 0.915 | 4.3 | 5-Hydroxytryptamine(serotonin) receptor 2A/adrenergic, alpha-1A receptor inhibitor, dopamine receptor antagonist/ ADRA1A inhib; DRD antag |
| Thiethylperazine Maleate | 0.832 | 4.4 | 5-Hydroxytryptamine(serotonin) receptor 2A/adrenergic, alpha-1A receptor inhibitor, dopamine receptor antagonist/ ADRA1A inhib; DRD antag |
| Cyproheptadine Hydrochloride | 0.493 | | 5-Hydroxytryptamine(serotonin) receptor 2A/histamine H(1) receptor inhibitor |
| Prochlorperazine Edisylate | 0.890 | 5.2 | 5-Hydroxytryptamine(serotonin) receptor 2A/histamine H(1) receptor inhibitor; dopamine D2 receptor agonist |

TABLE 6-continued

| Agent | Max Effect | IC50 (μM) | Previously described activity |
|---|---|---|---|
| Triflupromazine Hydrochloride | 0.541 | 12.1 | 5-Hydroxytryptamine (serotonin) receptor 2B/cholinergic receptor inhibitor; dopamine receptor antagonist |
| Paroxetine Hydrochloride Hemihydrate | 0.820 | 9.3 | Solute carrier family 6 (neurotransmitter transporter, serotonin), member 4 inhibibitor |
| Sertraline Hydrochloride | 0.418 | | Solute carrier family 6 (neurotransmitter transporter, serotonin), member 4 inhibibitor |
| Clomipramine Hydrochloride | 0.585 | 6.3 | Solute carrier family 6 (neurotransmitter transporter, serotonin), member 4/member 2 inhibitor; glutathione transferase inhibitor |
| Fenretinide | 0.426 | | Nuclear, retinoic acid receptor binder |
| Ciclesonide | 0.512 | 16.0 | Nuclear receptor subfamily 3, group C, member 1 (glucocorticoid receptor) activator |
| Brefeldin A | 0.900 | <1.6 | ADP-ribosylation factor 1 binder |
| Carbobenzoxy-valinyl-phenylalaninal | 0.607 | 2.9 | Calpain inhibitor |
| BML-248 | 0.554 | 0.2 | Cysteine Protease inhibitor |
| Leupeptin HCl | 0.865 | 3.2 | Cysteine Protease inhibitor |
| Tunicamycin | 0.800 | <0.28 | P-MurNAc penapeptide synthase; glycosyltransferase inhibitor |
| MG115 | 0.693 | 0.9 | Proteasome 26S inhibitor |
| MG-132 | 0.900 | <0.6 | Proteasome 26S inhibitor |
| Epoxomicin | 0.466 | | Proteasome inhibitor |
| Cycloheximide | 0.900 | <1.6 | Ribosome ribosomal peptidyl transferase inhibitor |
| Anisomycin | 0.900 | <1.6 | Ribosome ribosomal peptidyl transferase inhibitor |
| CGS 15943 | 0.449 | | Adenosine receptor inhibitor |
| Pimozide | 0.685 | 4.8 | Receptor_Dopamine receptor antagonist; Delta-type opioid receptor binder; Calcium channel alpha-1G blocker |
| Guanethidine Monosulfate | 0.793 | 8.7 | Receptor_adrenergic, Adrenergic receptor antagonist; solute carrier family 6 (neurotransmitter transporter, serotonin), member 4 inhibitor |
| Flupentixol Dihydrochloride | 0.660 | 3.8 | Adrenergic receptor 1A antagonist |
| Perphenazine | 0.793 | 5.8 | Adrenergic receptor 1A inhibitor; Dopaminergic 2A receptor antagonist |
| Trifluoperazine Hydrochloride | 0.955 | 5.0 | Adrenergic receptor 1A inhibitor; Dopaminergic antagonist |
| EGFR Inhibitor | 0.659 | 0.6 | Epidermal growth factor receptor inhibitor |
| Sunitinib Malate | 0.788 | 4.4 | Vascular endothelial growth factor recptor 2 inhibitor |
| Chlorcyclizine Hydrochloride | 0.456 | | Histamine receptor inhibitor |
| Astemizole | 0.835 | 4.3 | Histamine receptor 1 inhibitor |
| Clemastine Fumarate | 0.850 | 4.0 | Histamine receptor 1 inhibitor |
| Terfenadine | 0.914 | 6.1 | Histamine receptor 1 inhibitor |
| Chlorphenoxamine Hydrochloride | 0.789 | 5.0 | Histamine receptor 1 inhibitor |
| Oxatomide | 0.622 | 2.1 | Histamine receptor 1 inhibitor |
| Azelastine | 0.648 | 121.6 | Histamine receptor 1 inhibitor |
| Clemastine | 0.525 | 2.9 | Histamine receptor 1 inhibitor |
| Methdilazine Hydrochloride | 0.519 | 7.1 | Histamine receptor 1 inhibitor |
| Homochlorcyclizine dihydrochloride | 0.508 | 8.7 | Histamine receptor 1 inhibitor |
| Desloratadine | 0.430 | | Histamine receptor 1 inhibitor |
| Flunarizine Hydrochloride | 0.402 | | Histamine receptor 1 inhibitor |
| Loratadine | 0.371 | | Histamine receptor 1 inhibitor |
| Doxylamine Succinate | 0.731 | 5.2 | Receptor_histamine, histamine receptor H1/cholinergic receptor 1 inhibitor |
| Propoxyphene Hydrochloride | 0.422 | | Receptor_neural, opiate receptor binder |
| Benztropine Mesylate | 0.633 | 3.7 | Receptor_neural, cholinergic receptor 1 inhibitor |
| Dicyclomine Hydrochloride | 0.596 | 5.7 | Receptor_neural, cholinergic receptor 1 inhibitor |
| Piperacetazine | 0.641 | 6.6 | Dopamine receptor antagonist |
| Vanoxerine | 0.564 | 5.8 | Dopamine receptor antagonist |
| Pergolide Mesylate | 0.383 | | Dopamine receptor 1 and 2 agonist |
| Acetophenazine Maleate | 0.478 | | Dopamine receptor 1 and 2 antagonist |
| Bromocriptine Mesylate | 0.422 | | dopamine receptor 2 agonist |
| Fluphenazine Hydrochloride | 0.988 | 4.2 | Dopamine receptor 2 antagonist |
| N-(4-Aminobenzoyl)-L-glutamic acid | 0.855 | 9.7 | GABA receptor A inhibitor |

TABLE 6-continued

| Agent | Max Effect | IC50 (μM) | Previously described activity |
|---|---|---|---|
| Aripiprazole | 0.807 | 7.5 | Histamine receptor inhibitor; dopaminergic receptor 2 antagonist |
| Drotaverine Hydrochloride | 0.367 | | Opioid receptor, mu 1/K1 antagonist |
| Maprotiline Hydrochloride | 0.795 | 7.6 | Solute carrier family 6 (neurotransmitter transporter, noradrenalin), member/histamine receptor H1 inhibitor; adrenergic receptor 1A antagonist |
| CKI7 | 0.565 | 10.7 | Signal, casein kinase inhibitor |
| Triptolide | 0.850 | <0.1 | DEVD cleaving caspase activator |
| NSC 625987 | 0.418 | | CDK4-CycD1 inhibitor |
| Bay 41-2272 | 0.900 | <0.5 | Guanylate cyclase activator |
| Alverine Citrate | 0.495 | | Phosphodiesterase inhibitor |
| Tannic Acid | 0.543 | | CXL12 inhibitor |
| IMD-0354 | 0.661 | 3.1 | IKKA inhibitor |
| Arbidol | 0.592 | 6.0 | Immunostimulator |
| Andrographis | 0.523 | 12.9 | Immunostimulator |
| Pyrvinium Pamoate | 0.800 | 3.4 | AKT kinase antagonist |
| Deguelin | 0.418 | 0.5 | AKT kinase antagonist |
| Dasatinib | 0.428 | | BCR-ABL1/Src inhibitor |
| 5-Iodotubercidin | 0.369 | | ERK2/ADK/CK1/CK2/IRK inhibitor |
| SP 600125 | 0.365 | | JNK kinase inhibitor |
| PMA | 0.800 | <0.18 | PKC kinase activator |
| Cepharanthine | 0.652 | 5.6 | PKC kinase inhibitor |
| Sangivamycin Hydrate | 0.900 | <0.2 | PKC kinase inhibitor |
| PKR inhibitor | 0.434 | | PKR kinase inhibitor |
| Okadaic Acid | 0.488 | | Protein phosphatase 1/protein phosphatase 2A inhibitor |
| Sorafenib Tosylate | 0.819 | 3.9 | RAF kinase inhibitor |
| Sodium Vanadate | 0.525 | 13.0 | Tyrosine phosphatase inhibitor |
| Latrunculin B | 0.621 | 0.4 | Actin polymerization antagonist |
| Nocodazole | 0.800 | 0.5 | Tubulin destablizer |
| Mebendazole | 0.500 | 0.7 | Tubulin destablizer |
| TN-16 | 0.800 | 1.8 | Tubulin destablizer |
| Fenbendazole | 0.500 | 5.8 | Tubulin polymerization inhibitor |
| Podofilox | 0.800 | 1.8 | Tubulin polymerization inhibitor |
| Triclabendazole | 0.552 | 9.2 | Tubulin polymerization stabilizer |
| Oxibendazole | 0.472 | | Tubulin polymerization stabilizer |
| Vinorelbine Tartrate Hydrate | 0.472 | 3.2 | Tubulin beta 2 destabilizer |
| Thapsigargin | 0.700 | <0.3 | Sarcoplasmic/endoplasmic reticulum calcium ATPase inhibitor |
| 2,6-Divanillylidenecyclohexanone | 0.932 | 6.4 | Unknown_aliment, choleretic |
| 1,5'-Bis(2-Nitrophenoxy)pentane | 0.531 | 13.0 | Unknown analog, pentamidine |
| (1S,4S)-Desmethyl Sertraline, Hydrochloride | 0.688 | 1.3 | Unknown analog, sertraline metabolite |
| Podophyllum | 0.800 | <1.6 | Unknown, herbal |
| Saponin | 0.558 | 4.8 | Antiseptic |
| Nonoxynol-9 | 0.535 | 8.7 | Antiseptic |
| Domiphen Bromide | 0.715 | 7.5 | Unknown, antiseptic |
| Sodium Bicarbonate | 0.389 | | Unknown_ |

The top 30 agents identified in the initial screen as outlined in Table 6 were re-tested for inhibitory activity in both Vero and HepG2 cells. The results of this analysis are in provided in Table 7. These agents effectively inhibited replication of the Ebola replicon at low to sub micromolar concentrations.

TABLE 7

| Agent Name | Max Effect Vero | IC50 (μM)

TABLE 7-continued

| Agent Name | Max Effect Vero | IC50 (μM) Vero | Max Effect HepG2 | IC50 (μM) HepG2 |
|---|---|---|---|---|
| Clemastine Fumarate | 0.958 | 5.4 | 0.933 | 0.65 |
| Astemizole | 0.965 | 6.2 | 0.914 | 1.4 |
| Benztropine Mesylate | 0.899 | 8.0 | 0.943 | 2.6 |
| Piperacetazine | 0.962 | 12 | 0.954 | 3.3 |
| Fluphenazine Hydrochloride | 0.968 | 5.5 | 0.920 | 3.0 |
| Aripiprazole | 0.530 | 20 | 0.947 | 3.8 |
| Maprotiline Hydrochloride | 0.986 | 9.6 | 0.925 | 2.9 |
| Dasatinib | 0.642 | 16 | 0.941 | 4.2 |
| Vinorelbine Tartrate Hydrate | 0.256 | NA | 0.788 | 0.86 |
| Teicoplanin | 0.846 | 7.3 | 0.770 | 2.4 |
| Hycanthone | 0.968 | 11 | 0.962 | 6.0 |
| Quinacrine Dihydrochloride | 0.923 | 5.7 | 0.862 | 1.0 |
| Efavirenz | 0.639 | 10 | 0.860 | 14 |

Example 2

Identification of Synergistic Combination Therapies using the Ebola Replicon Assay The screening method described in Example 1 was used to identify combinations of agents that synergistically inhibit viral replication. For each combination of agents, a synergy score was calculated by the formula S=log $f_X$ log $f_Y$ $\Sigma$ $I_{data}$ ($I_{data}$−$I_{Loewe}$), summed over all non-single-agent concentration pairs, and where log $f_{X,Y}$ are the natural logarithm of the dilution factors used for each single agent. This effectively calculates a volume between the measured and Loewe additive response surfaces, weighted towards high inhibition and corrected for varying dilution factors. In general, the magnitude of the synergy score indicates the strength of the synergistic interaction. For the Ebola screening described in Example 2, synergy scores >1.0 indicate a synergistic effect of Agent 1 and Agent 2 and synergy scores between 0.3 and 1.0 indicate an additive effect of Agent 1 and Agent 2.

Potency shifting was scored using a combination index (CI) (Chou et al., *Adv. Enzyme Regul.,* 22:27-55 (1984)). For a chosen iso-effect level $I_{cut}$, $CI_I=(C_X/EC_X)_I+(C_Y/EC_Y)_I$, where $(C_X/EC_X)_I$ for a particular data point is the ratio of the X compound's measured concentration to its effective concentration at the chosen inhibition level. The CI is a rough estimate of how much less drug was needed in combination relative to the single agent doses required to achieve the chosen effect level. CI values around 1.0 are dose additive interactions. CI values <1 are synergistic. CI values in the range of 0.5-0.7 are typical for in vitro measurements of current clinical combinations (Greco et al., *Pharmacol. Rev.,* 47:331-85 (1995)). The choice of effect levels for the CI calculations were selected by using an algorithm that finds the observed $I_{data}$ with the largest $I_{data}$−$I_{Loewe}$, excluding those points with $I_{data}$ exceeding the lesser single agent's $I_{max}$. This exclusion is applied to ensure that the CI reflects the best synergy at levels covered by both single agents. The chosen iso-level is then floored at a 20% inhibition level, beneath which inhibitions often are unreliable, and rounded to the nearest 5%. The synergy scores and CI for the agent pairs identified in our screen are listed in Table 8.

TABLE 8

| Agent A | Agent B | Synergy Score | CI (Std. Error) |
|---|---|---|---|
| Lomerizine | Vinorelbine | 2.42 | 0.209 (0.007) |
| Pimozide | Vinorelbine | 2.24 | 0.236 (0.01) |
| Aripiprazole | Vinorelbine | 3.55 | 0.210 (0.005) |
| Aripiprazole | Dasatinib | 4.08 | 0.298 (0.05) |
| Dasatinib | Lomerizine | 2.85 | 0.400 (0.09) |
| Aripiprazole | Piperacetazine | 4.43 | 0.257 (0.04) |
| Pimozide | Thioridazine | 1.04 | 0.769 (0.1) |
| Aripiprazole | Astemizole | 0.34 | 0.911 (0.02) |
| Clemastine | Sertraline | 1.07 | 0.578 (0.04) |
| Bepridil | Clomiphene | 0.385 | 1.05 (0.02) |
| Bepridil | Toremifene | 1.18 | 0.864 (0.06) |
| Clomiphene | Sertraline | 1.77 | 0.537 (0.02) |
| Toremifene | Sertraline | 1.11 | 0.684 (0.05) |
| Sertraline | Vinorelbine | 1.24 | 0.506 (0.05) |
| Aripiprazole | Paroxetine | 0.994 | 0.869 (0.03) |

Example 3

In Vivo Efficacy of Single Agents in a Mouse Model of Ebola Infection

A mouse model of Ebola infection developed by Bray et al. (*J. Infect. Dis.,* 179:5248-58 (1999)) was used to show in vivo efficacy of single agents. C57BL/6 mice (n=10 mice per group) were challenged with 100 pfu of a mouse adapted Ebola virus by IP injection. One hour after challenge, the animals were treated with the single agents in Table 9 at the indicated dose and frequency for a total of 10 days. Animals were monitored for survival for a total of 28 days following infection and the mean time to death determined for all cases where there was a sufficient number of non-survivors. In cases where all animals survived, the mean time to death was not determined and is greater than 28 days.

TABLE 9

| Compound | Study | Dose | Dosing frequency | Survival day 28 | MTD |
|---|---|---|---|---|---|
| Clomiphene citrate | 1 | 60 mg/kg | QID | 90% | 12.00 |
| Clomiphene citrate | 2 | 60 mg/kg | QID | 100% | — |
| Clomiphene citrate | 3 | 60 mg/kg | QID male | 60% | 9.83 |
| Clomiphene citrate | 3 | 60 mg/kg | QID female | 70% | 9.00 |
| Toremifene | 1 | 60 mg/kg | QID | 50% | 9.80 |
| Toremifene | 2 | 60 mg/kg | QID | 60% | 10.25 |
| Toremifene | 2 | 60 mg/kg | SID | 60% | 8.75 |
| Toremifene | 3 | 60 mg/kg | SID | 80% | 8.00 |
| Toremifene | 3 | 60 mg/kg | BID | 10% | 10.22 |
| Toremifene | 3 | 80 mg/kg | SID | 60% | 8.75 |
| Bepridil | 1 | 12 mg/kg | BID | 100% | — |
| Bepridil +1 BID+ | 2 | 12 mg/kg | BID | 100% | — |
| Bepridil | 2 | 12 mg/kg | QID | 60% | 8.25 |
| Bepridil | 2 | 12 mg/kg | SID | 100% | — |
| Bepridil | 2 | 12 mg/kg | BID | 100% | — |
| Bepridil +1 BID+ | 3 | 12 mg/kg | BID | 90% | 7.00 |
| Bepridil +2 BID+ | 3 | 12 mg/kg | BID | 30% | 7.14 |
| Bepridil +3 BID+ | 3 | 12 mg/kg | BID | 10% | 7.00 |
| Bepridil +4 BID+ | 3 | 12 mg/kg | BID | 30% | 7.43 |

TABLE 9-continued

| Compound | Study | Dose | Dosing frequency | Survival day 28 | MTD |
|---|---|---|---|---|---|
| Clomipramine | 1 | 45 mg/kg | SID | 80% | 8.83 |
| Clomipramine | 2 | 45 mg/kg | BID | 50% | 9.40 |
| Lomerizine | 1 | 22 mg/kg | SID | 30% | 8.14 |
| Sertraline | 1 | 12 mg/kg | BID | 20% | 8.63 |

QID - every other day
SID - once daily
BID - twice daily
"+" Dosing x day after viral infection
"/" mice compared to female/male control animals Other Embodiments All publications, patent applications, and patents mentioned in this specification are herein incorporated by reference.

Various modifications and variations of the described compositions, methods, and kits of the invention will be apparent to those skilled in the art without departing from the scope and spirit of the invention. Although the invention has been described in connection with specific embodiments, it will be understood that the invention as claimed should not be unduly limited to such specific embodiments. Indeed, various modifications of the described modes for carrying out the invention that are obvious to those skilled in the fields of molecular biology, medicine, immunology, pharmacology, virology, or related fields are intended to be within the scope of the invention.

What is claimed is:

1. A composition comprising clomiphene citrate and sertraline HCl wherein clomiphene and sertraline HCl are present in amounts that, when administered together to a patient with a filovirus-mediated disease, are effective to treat said patient.

2. The composition of claim 1, wherein said filovirus is Ebola virus or Marburg virus.

3. A method for treating a patient having filovirus-mediated disease, said method comprising administering to said patient a composition of claim 1 in an amount that is effective to treat said patient.

4. The method of claim 3, wherein said filovirus is Ebola virus or Marburg virus.

* * * * *